US012778585B2

(12) United States Patent
Buck

(10) Patent No.: US 12,778,585 B2
(45) Date of Patent: Nov. 3, 2026

(54) ANASTOMOTIC COUPLER

(71) Applicant: Buck Surgical, Inc., St. Louis, MO (US)

(72) Inventor: Donald W. Buck, St. Louis, MO (US)

(73) Assignee: Buck Surgical, Inc., St. Louis, MO (US)

( * ) Notice: Subject to any disclaimer, the term of this patent is extended or adjusted under 35 U.S.C. 154(b) by 19 days.

(21) Appl. No.: 18/918,200

(22) Filed: Oct. 17, 2024

(65) Prior Publication Data

US 2025/0032117 A1 Jan. 30, 2025

Related U.S. Application Data

(63) Continuation-in-part of application No. 18/200,714, filed on May 23, 2023, now Pat. No. 12,496,068, which is a continuation-in-part of application No. 17/932,027, filed on Sep. 14, 2022, now Pat. No. 12,201,298, which is a continuation-in-part of application No. 17/536,439, filed on Nov. 29, 2021, now Pat. No. 12,329,383, which is a continuation-in-part of application No. 17/365,484, filed on Jul. 1, 2021, now Pat. No. 12,303,131, which (Continued)

(51) Int. Cl.
*A61B 17/11* (2006.01)

(52) U.S. Cl.
CPC ....... *A61B 17/11* (2013.01); *A61B 2017/1107* (2013.01); *A61B 17/1114* (2013.01); *A61B 2017/1132* (2013.01); *A61B 2017/1139* (2013.01)

(58) Field of Classification Search
CPC ............ A61B 17/11; A61B 2017/1132; A61B 2017/1135; A61B 2017/1139; A61B 17/1155
See application file for complete search history.

(56) References Cited

U.S. PATENT DOCUMENTS 3,316,914 A 5/1967 Collito
3,357,432 A 12/1967 Sparks (Continued)

FOREIGN PATENT DOCUMENTS

CN 101043851 A 9/2007
CN 103750875 A 4/2014

(Continued)

OTHER PUBLICATIONS

International Search Report (ISR) of PCT/US2024/053172, dated Jan. 8, 2024.

(Continued)

*Primary Examiner* — Mohamed G Gabr
*Assistant Examiner* — Khoa Tan Le
(74) *Attorney, Agent, or Firm* — POLSINELLI PC

(57) ABSTRACT

An anastomotic coupler is provided. A cartridge can include a frame extending along a longitudinal axis, one or more fasteners extending from the frame at an angle from the longitudinal axis, and one or more frictional elements extending from the frame at an angle from the longitudinal axis. The fasteners are operable to at least partially puncture a wall of a tubular structure. The frictional elements are operable to abut against the wall of the tubular structure without puncturing the wall.

20 Claims, 40 Drawing Sheets

Related U.S. Application Data is a continuation-in-part of application No. 17/181,440, filed on Feb. 22, 2021, now Pat. No. 11,998,208, which is a continuation of application No. 16/950,209, filed on Nov. 17, 2020, now Pat. No. 10,939,913.

(60) Provisional application No. 63/061,303, filed on Aug. 5, 2020, provisional application No. 62/936,868, filed on Nov. 18, 2019.

(56) References Cited

U.S. PATENT DOCUMENTS

| | | | | | |
|---|---|---|---|---|---|
| 5,397,345 | A * | 3/1995 | Lazarus | A61M 25/10 604/103.05 |
| 5,478,353 | A | 12/1995 | Yoon | |
| 5,720,755 | A | 2/1998 | Dakov | |
| 6,152,937 | A * | 11/2000 | Peterson | A61F 2/88 606/153 |
| 6,241,743 | B1 | 6/2001 | Levin et al. | |
| 6,248,117 | B1 | 6/2001 | Blatter | |
| 6,402,767 | B1 | 6/2002 | Nash et al. | |
| 6,524,322 | B1 | 2/2003 | Berreklouw | |
| 6,569,173 | B1 | 5/2003 | Blatter et al. | |
| 10,939,913 | B1 | 3/2021 | Buck | |
| 11,672,539 | B2 | 6/2023 | Agarwal et al. | |
| 11,998,208 | B2 | 6/2024 | Buck | |
| 12,303,131 | B2 | 5/2025 | Buck | |
| 12,329,383 | B2 | 6/2025 | Buck | |
| 2001/0039425 | A1 | 11/2001 | Dakov | |
| 2001/0047180 | A1* | 11/2001 | Grudem | A61B 17/11 606/153 |
| 2002/0082625 | A1 | 6/2002 | Huxel et al. | |
| 2004/0054405 | A1 | 3/2004 | Richard et al. | |
| 2006/0004394 | A1* | 1/2006 | Amarant | A61B 17/11 606/153 |
| 2006/0149349 | A1 | 7/2006 | Garbe | |
| 2008/0114385 | A1 | 5/2008 | Byrum | |
| 2008/0200938 | A1 | 8/2008 | Lui | |
| 2010/0036399 | A1 | 2/2010 | Viola | |
| 2010/0082049 | A1 | 4/2010 | Orban, III | |
| 2011/0106118 | A1 | 5/2011 | Son et al. | |
| 2011/0264121 | A1 | 10/2011 | Liu | |
| 2011/0270287 | A1 | 11/2011 | Borghi | |
| 2011/0306994 | A1 | 12/2011 | Bassan et al. | |
| 2013/0110140 | A1 | 5/2013 | Lin et al. | |
| 2013/0193190 | A1 | 8/2013 | Carter et al. | |
| 2013/0267968 | A1 | 10/2013 | Ferlin | |
| 2016/0095599 | A1 | 4/2016 | Jose et al. | |
| 2019/0150928 | A1 | 5/2019 | Boiman et al. | |
| 2019/0175172 | A1 | 6/2019 | Kollar et al. | |
| 2019/0321046 | A1 | 10/2019 | Williams | |
| 2020/0113567 | A1 | 4/2020 | Bakos et al. | |
| 2020/0337707 | A1 | 10/2020 | Ad-E et al. | |
| 2023/0009775 | A1 | 1/2023 | Buck | |
| 2023/0240681 | A1 | 8/2023 | Higdon et al. | |

FOREIGN PATENT DOCUMENTS

| | | | |
|---|---|---|---|
| EP | 1825821 | A1 | 8/2007 |
| WO | 2009/118719 | A1 | 10/2009 |
| WO | 2013/004263 | A1 | 4/2014 |

OTHER PUBLICATIONS

International Search Report (ISR) of PCT/US2024/050874, dated Dec. 12, 2024.
Non-Final Office Action for U.S. Appl. No. 19/191,088, dated Sep. 16, 2025, 15 pages.
International Preliminary Report on Patentability of PCT/US20/60857 dated Feb. 9, 2021.
Non-Final Office Action for U.S. Appl. No. 18/200,714, issued Jun. 3, 2025 (11 pages).
Non-Final Office Action for U.S. Appl. No. 19/181,088, issued Jun. 16, 2025 (16 pages).
Notice of Allowance for U.S. Appl. No. 17/536,439, dated Apr. 15, 2025, pages.
Notice of Allowance for U.S. Appl. No. 17/365,484, dated Apr. 16, 2025, pages.
Notice of Allowance for U.S. Appl. No. 19/191,088, dated Dec. 23, 2025, 7 pages.
European Search Report (EESR) of European Patent Application No. EP 20890827.7, dated Jul. 24, 2023, 14 pages.
International Search Report of PCT/US2020/060857, dated Jan. 18, 2021, pages.
Office Action for Chinese Application No. 202080069581.8, issued on May 8, 2023, 8 pages (5 pages of Official and 3 pages of English Translation).
Non-Final Office Action for U.S. Appl. No. 17/181,440, issued Oct. 26, 2023, 28 pages.
Vocabulary.com definition for needle a ccessed Oct. 20, 2023, 4 pages [https://www.vocabulary.com/dictionary/needle].
Vocabulary.com definition for "pin" accessed Oct. 20, 2023, 4 pages. [https://www.vocabulary.com/dictionary/pin].
Notice of Preliminary Rejection for Korean Application No. 10-2022-7005161, issued Jun. 23, 2022, 7 pages (3 pages of official and 4 pages of English Translation).
English Translation of Office Action for Chinese Application No. 202080069581.8, issued on Nov. 30, 2022, 3 pages.
English Translation of the Office Action for Brazil Application No. 112022004182.9, issued Nov. 8, 2022, 4 pages.
Office Action for U.S. Appl. No. 17/365,484, dated Jan. 21, 2025 (15 pages).
Office Action for U.S. Appl. No. 17/536,439, dated Jan. 21, 2025 (8 pages).
Non-Final Office Action for U.S. Appl. No. 18/982,317, dated Mar. 25, 2026, 5 pages.
Non-Final Office Action for U.S. Appl. No. 18/647,714, dated Apr. 2, 2026, 12 pages.

* cited by examiner

ANASTOMOTIC COUPLER

CROSS-REFERENCE TO RELATED APPLICATIONS

This application is a continuation-in-part application of U.S. application Ser. No. 18/200,714 filed May 23, 2023, which is a continuation-in-part application of U.S. application Ser. No. 17/932,027 filed Sep. 14, 2022, which is a continuation-in-part application of U.S. application Ser. No. 17/536,439 filed Nov. 29, 2021, which is a continuation-in-part application of U.S. application Ser. No. 17/365,484 filed Jul. 1, 2021, which is a continuation-in-part application of U.S. application Ser. No. 17/181,440 filed Feb. 22, 2021, which is a continuation application of U.S. application Ser. No. 16/950,209 filed Nov. 17, 2020, now U.S. Pat. No. 10,939,913, which claims the benefit of U.S. Provisional Patent Application No. 62/936,868, filed in the U.S. Patent and Trademark Office on Nov. 18, 2019, and U.S. Provisional Patent Application No. 63/061,303, filed in the U.S. Patent and Trademark Office on Aug. 5, 2020, each of which is incorporated herein by reference in its entirety for all purposes.

FIELD

The present disclosure relates generally to an anastomotic coupler. In at least one example, the present disclosure relates to a surgical system and method to utilize an anastomotic coupler to connect two tubular structures such as vessels, esophagus, intestine, lymphatic structure, and/or graft material.

BACKGROUND

An anastomosis is a connection between two luminal structures. Commonly, these connections can occur with blood vessels (for example, vascular anastomosis), or tubular gastrointestinal structures (for example, intestines, stomach, esophagus). Conventional techniques allow the anastomosis to be completed between two ends (referred to as end-to-end anastomosis), or between the end of one structure and the side of another structure (referred to as end-to-side anastomosis). Procedures requiring these anastomoses are carried out thousands of times per day, globally. Likewise, multiple surgical specialties rely upon the creation of reliable, unobstructed anastomoses for successful treatment of their respective patients.

BRIEF DESCRIPTION OF THE DRAWINGS

Implementations of the present technology will now be described, by way of example only, with reference to the attached figures, wherein.

DETAILED DESCRIPTION

Figure 1:
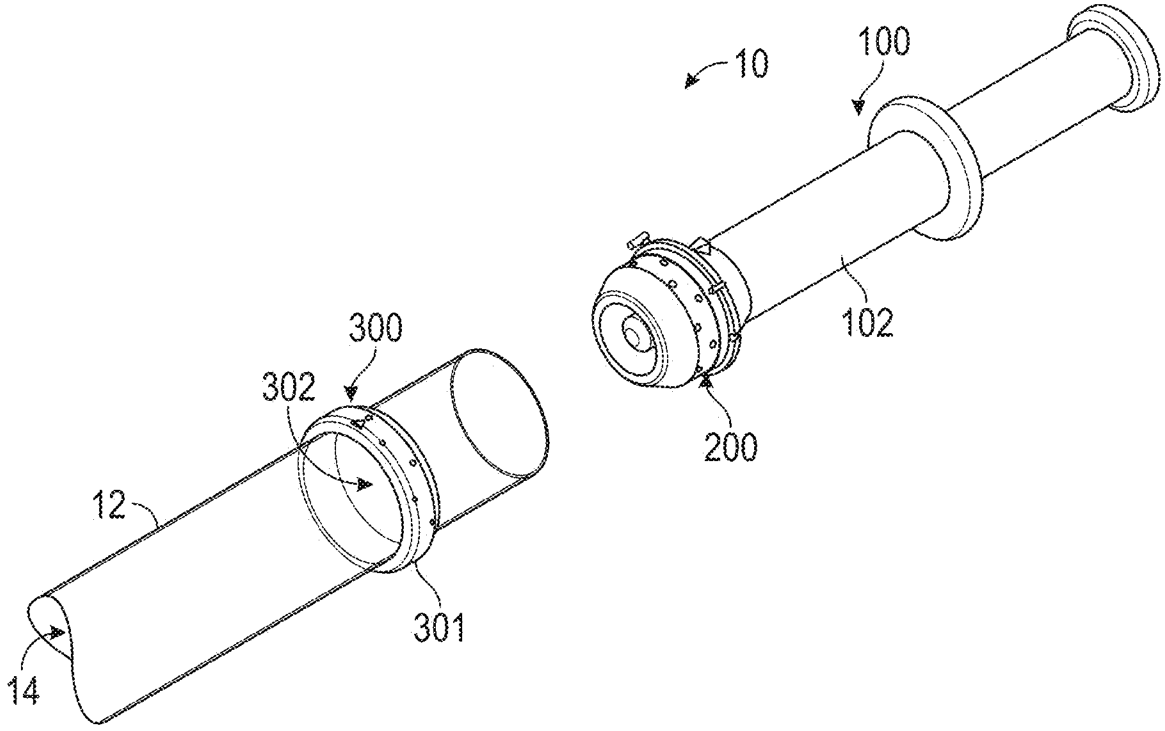
FIG. 1 illustrates a diagram of an anastomotic coupler.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the examples described herein. The drawings are not necessarily to scale and the proportions of certain parts may be exaggerated to better illustrate details and features of the present disclosure.

The original technique for vascular suture anastomoses was created by Alexis Carrel between 1901-1910. This pioneering work resulted in Carrel receiving the Nobel Prize in 1912. Despite 100 years of surgical evolution and innovation since that discovery, the majority of vascular anastomoses to this day still employ suture techniques similar to Carrel's initial description in the early 1900s. In the 1970s, gastrointestinal stapling devices were introduced, which quickly replaced primary suture techniques for bowel anastomoses. However, most surgeons still employ circumferential suture techniques in the serosal layer overlying the stapled anastomosis for added support. Although generally successful, these techniques can take long periods of time, often require additional surgical expertise, and if not performed correctly, may result in leakage (blood, stool contents, gastric contents, lymphatic fluid), constriction, stenosis, and/or obstruction at the anastomotic site. In the case of vascular anastomoses, stenosis and/or obstruction can result in catastrophic complications such as heart attack, stroke, peripheral limb ischemia, amputation, death, and reconstructive failure and soft-tissue loss. For example, in the setting of gastrointestinal anastomoses, these complications can result in extra-luminal leak of gastrointestinal contents, infection, sepsis, obstruction, and death.

With the understood importance of reliable, open anastomoses, alternatives to sutures and staples have been used. An example of a vascular anastomotic coupler is described, for instance, in U.S. Patent Pub. No. 2015/0088172 A1 (the '172 Publication). This coupler has two circular ends with spikes or pins. The vessel is brought through the ring and the vessel wall is everted, or rolled over, the pins for securement as shown in FIGS. 2A and 2B of the '172 Publication. This is completed on each vessel end, and the two rings are then brought together with the spikes/pins being forced into the opposite ring to join the ends together as shown in FIG. 1C of the '172 Publication. However, because of the potential for micro-motion of the vessels and size mismatch due to the anastomotic coupler of the '172 Publication, blood leakage may happen, and/or one of the pins may tear through the vessel wall creating a leak and/or site for platelet aggregation and thrombosis (blood clot formation). Likewise, with the anastomotic coupler of the '172 Publication, for thicker walled, less elastic vessels, particularly arteries, everting vessel edges can be quite difficult and may result in trauma to the vessel wall (intima) and/or stenosis at the anastomosis, both of which can create platelet aggregation, turbid flow, and/or thrombosis with subsequent obstruction of flow. Additionally, the technique of the '172 Publication requires additional specialized equipment (surgical microscope, high-powered loupe magnification) to use. For gastrointestinal stapled anastomoses, many procedures are performed either side-to-side which is not a natural pathway for intestinal smooth muscle propulsion of stool contents (for example, non-longitudinal flow along the length of the intestine), or end-to-end, which requires a separate, remote full-thickness bowel access incision for deployment, thereby creating a secondary weak point for potential leak, or adhesion formation.

Referring now to FIG. 1, an anastomotic coupler 10 is provided. The anastomotic coupler 10 is provided to create a connection between adjacent tubular structures 12. The tubular structure 12 can include blood vessels, grafts, prostheses, gastrointestinal structures, esophagus, lymphatics, and/or any other suitable channels of the body or the operation for which the tubular structure 12 is created. The tubular structure 12 forms a lumen 14 through which matter can be passed, for example blood, food, fluids, and/or cells.

The anastomotic coupler 10 includes a ring 300 forming an aperture 302. The ring 300 is operable to receive a tubular structure 12 through the aperture 302. While the ring 300 as illustrated in FIG. 1 has a substantially circular shape, the ring 300 can have any suitable shape such as rectangular, triangular, octagonal, hexagonal, and/or oval. Additionally, the ring 300 as illustrated in FIG. 1 is a singular solid piece, in some examples, for ease of application or manufacturing purposes, the ring 300 can include two semi-circular or arc-type pieces that are joined together around the tubular structure 12.

The size of the lumen 302 of the ring 300 can vary based on the application and the size of the tubular structure 12. For example, the diameter of the lumen 302 can range from about 0.5 millimeters (mm) (for example for lymphatic connections) to about 60 millimeters (for example for gastrointestinal connections). Due to the range of diameters for the ring 300, and the range of diameters for the tubular structure 12, the appropriate ring 300 can be selected by measuring the internal diameter of the tubular structure 12. This can be accomplished, for example, with an intraluminal measurement guide/device. If there is a significant size mismatch (1 mm or greater) between the tubular structure 12 and the ring 300, then a short, cylindrical tube connector with a corresponding male and female end can be used to allow for gradual transition in size in any direction to accommodate the size difference. For example, a cylindric tube can be provided that tapers in size such that one end is 1 mm-2 mm larger/smaller than the other end, which would enable a connection of a 1 mm vessel to a 2.5 mm-3.5 mm vessel during microsurgical procedures without problem and vice versa.

Figure 2:
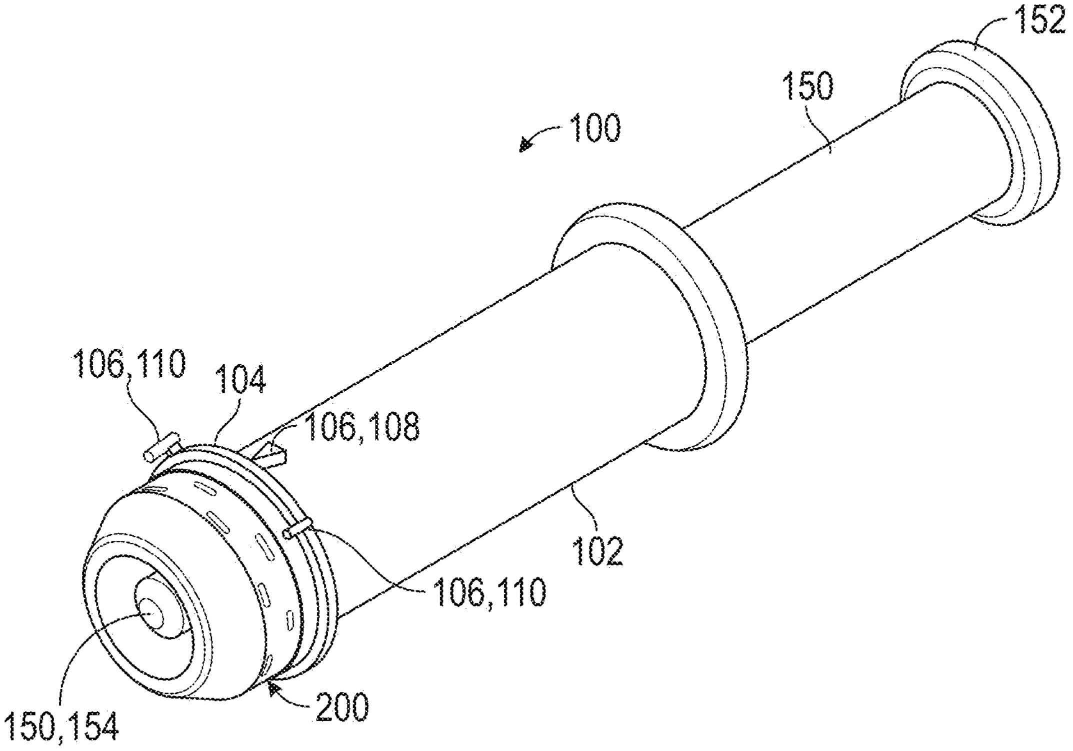
FIG. 2 illustrates a fixation device.

Referring also to FIG. 2, the anastomotic coupler 10 also includes a fixation device 100. The fixation device 100 is operable to couple the tubular structure 12 with the ring 300. The fixation device 100 can include a housing 102 and a cartridge 200. The cartridge 200 includes a plurality of fasteners 206 (as shown in FIGS. 5-10B). The fasteners 206 are operable to puncture the tubular structure 12 and be partially received in the ring 300 to couple the tubular structure 12 with the ring 300. In at least one example, the cartridge 200 can be removably coupled with the housing 102. Accordingly, the cartridge 200 may be replaceable to allow multiple uses of the fixation device 100. In some examples, the cartridge 200 may not be removable such that the fixation device 100 is provided for a one-time use. The fixation device 100 can include a pusher rod 150 operable to actuate the fixation device 100 to drive the fasteners 206 from the cartridge 200. Upon actuation of the fixation device 100, the pusher rod 150 can translate along a longitudinal axis.

Figure 3:
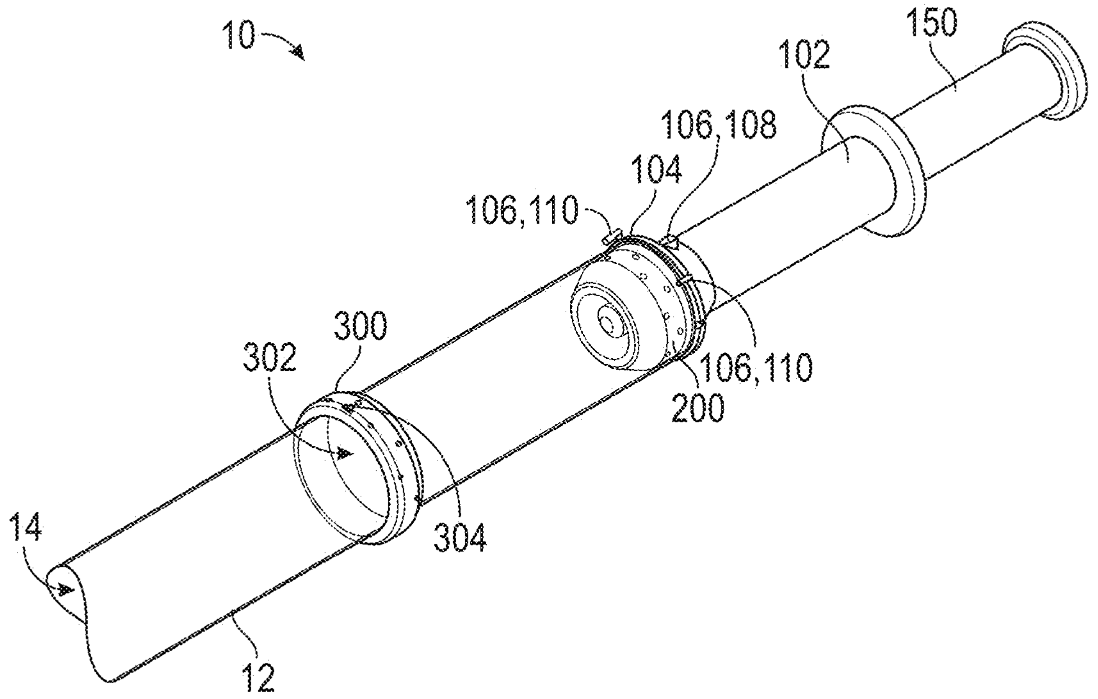
FIG. 3 illustrates a tubular structure being received by a fixation device.

The fixation device 100 includes stop 104 to receive the tubular structure 12. In at least one example, the stop 104 can be formed as a portion of the cartridge 200 to ensure alignment with the cartridge 200. In some examples, the stop 104 can be formed as a portion of the housing 102. The stop 104 extends radially from the housing 104 such that a free end of the tubular structure abuts the stop 104. As illustrated in FIG. 3, the housing 102 receives the free end of the tubular structure 12 such that the cartridge 200 is inserted into the lumen 14 of the tubular structure. When correctly positioned, the free end of the tubular structure 12 abuts the stop 104. The stop 104 ensures the placement and alignment of the ring 300, the cartridge 200, and the free end of the tubular structure 12. The alignment of the ring 300, the cartridge 200, and the free end of the tubular structure 12 is critical to ensure adequate connection between the tubular structure 12 and another tubular structure 12.

Figure 4:
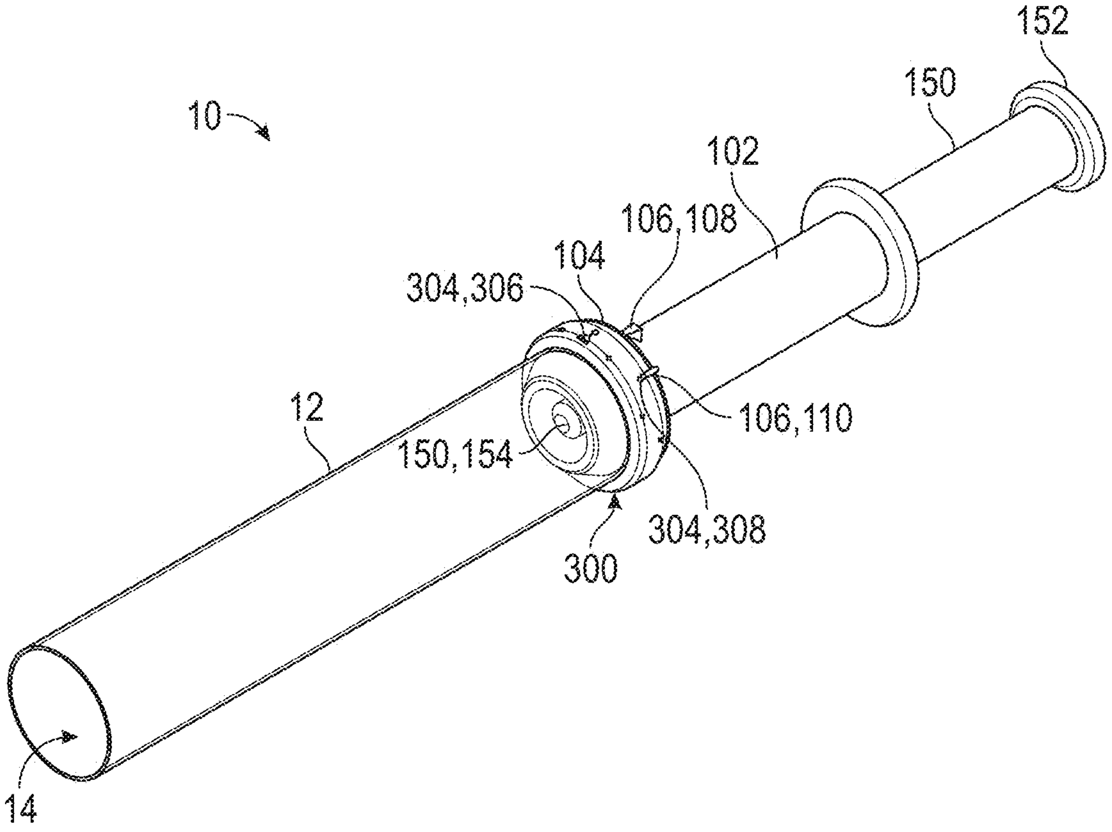
FIG. 4 illustrates a ring being aligned with a cartridge of the fixation device.

As illustrated in FIG. 4, after the tubular structure 12 is received by the fixation device 100 and abuts the stop 104, the ring 300 can be positioned to abut the stop such that the ring 300 is aligned with the free end of the tubular structure 12.

The stop 104 can include a plurality of alignment components 106 which correspond with alignment components 304 of the ring 300. Accordingly, when the ring 300 is aligned and/or correctly positioned, the alignment components 106 of the stop 104 are aligned with the alignment components 304 of the ring 300. In some examples, the alignment components 106, 304 can include one or more alignment markers 108, 304. The alignment markers 108, 304 can be shaped, for example as triangles. Accordingly, to align the ring 300, the tips of the triangles for the alignment markers 108, 304 can point towards one another. In some examples, the alignment components 106, 304 can include one or more alignment pins 110 and corresponding alignment receivers 308. When the ring 300 is aligned, the alignment pins 100 can be received by the alignment receivers 308. While the figures illustrate the alignment pins 100 being disposed on the fixation device 100 and the alignment receivers 308 being disposed on the ring 300, in some examples, the alignment pins 100 may be disposed on the ring 300 and the alignment receivers can be disposed on the fixation device 100.

Figure 5:
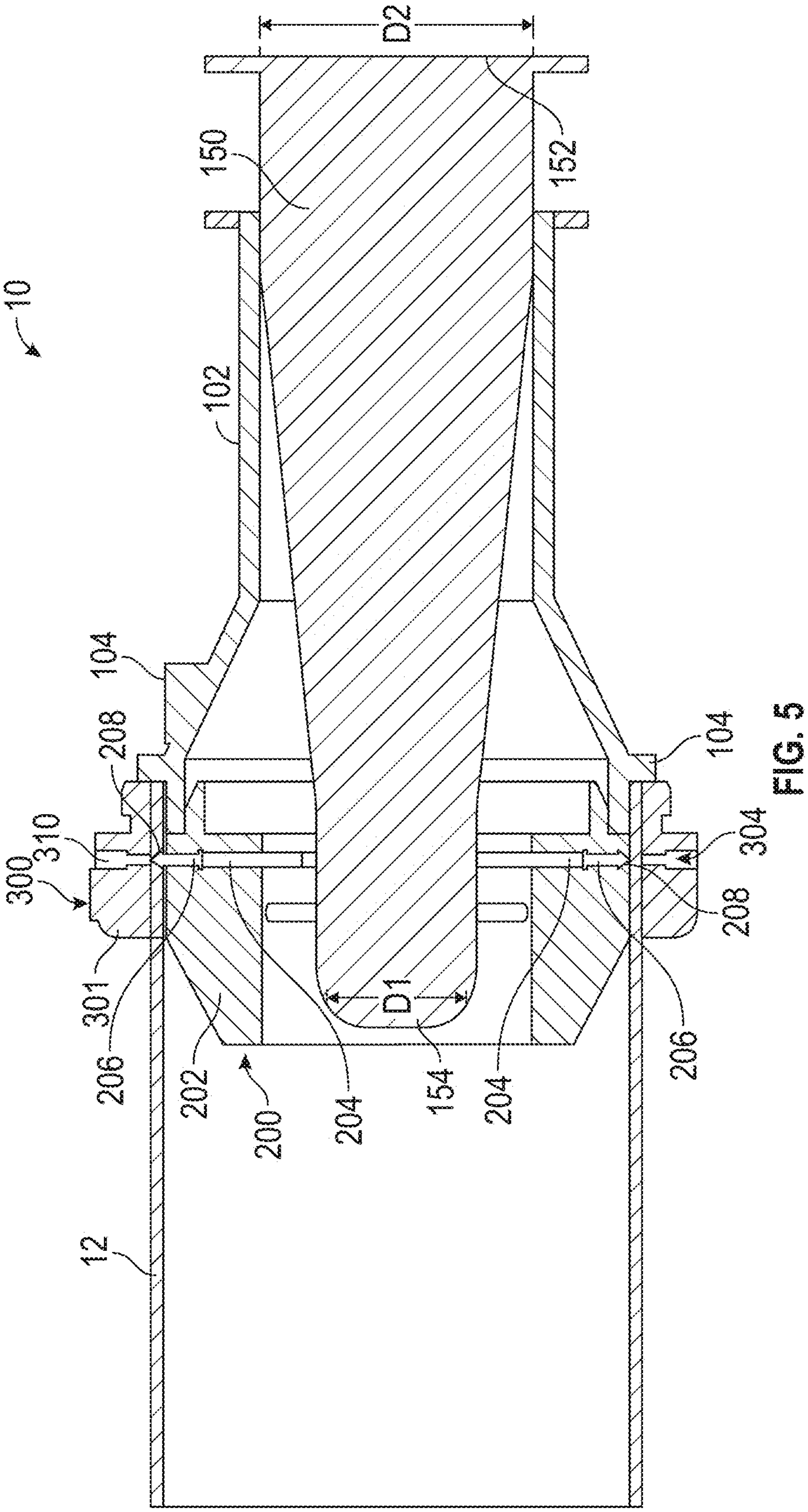
FIG. 5 illustrates a cross-sectional view of FIG. 4.

FIG. 5 illustrates a cross-sectional view of the tubular structure 12, the ring 300, and the cartridge 200 aligned. In addition to ensuring the ring 300 aligns with the free end of the tubular structure 12, the ring 300 is aligned with the cartridge 200. When the ring 300 is properly aligned with the cartridge 200, a plurality of receiving portions 310 of the ring 300 are aligned with the plurality of fasteners 206 of the cartridge 200.

The fasteners 206 can be any suitable fastener 206 to couple the ring 300 with the tubular structure 12 and prevent movement between the ring 300 and the tubular structure 12. For example, the fasteners 206 can include tacks 600, 700 (as shown in FIGS. 6 and 7), staples 800 (as shown in FIG. 8), pins, adhesive, internal ring, internal mesh, wire, clamp, coil, stent, and/or suture.

Figure 6:
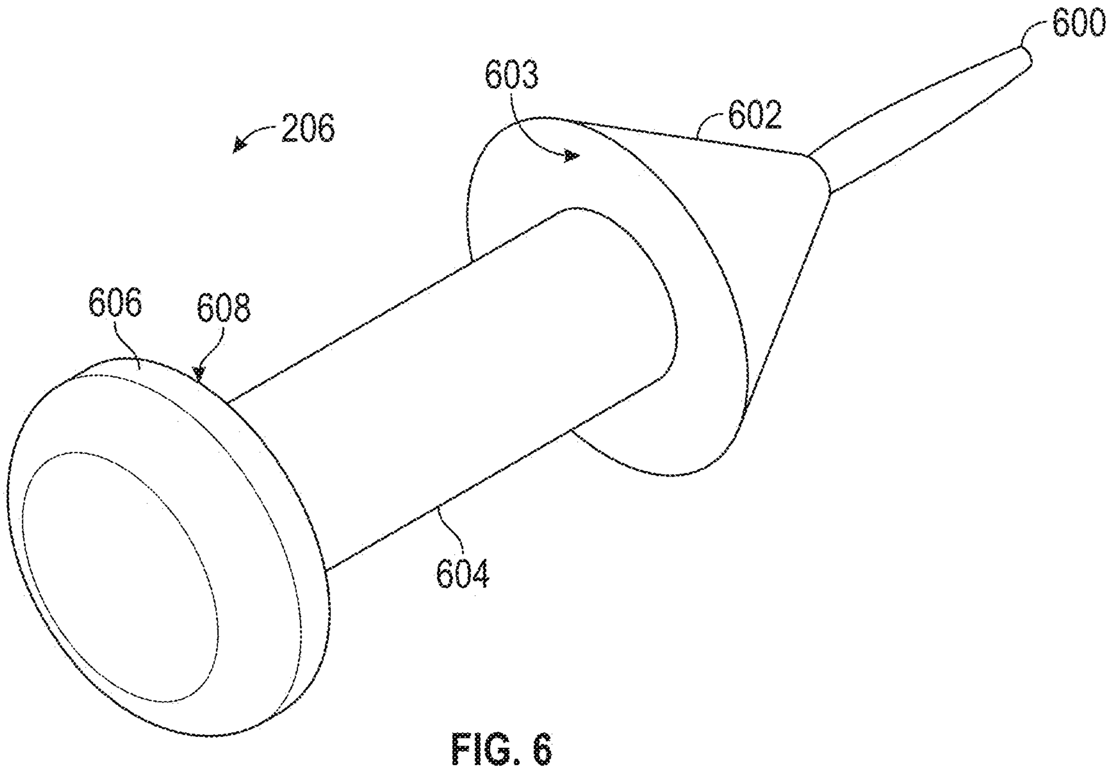
FIG. 6 illustrates an exemplary fastener.

As illustrated in FIG. 6, the tack 600 can include a puncturing portion 602 which is operable to puncture the tubular structure 12. An abutment surface 603 abuts against a surface of the corresponding receiving portion 310 of the ring 300. A body 604 spans the thickness of the wall of the tubular structure 12, and an end 606 includes an abutment surface 608 which abuts against the inner surface of the tubular structure 12. The abutment surfaces 603, 608 prevent the fastener 206 from being removed from the tubular structure 12 and the ring 300.

Figure 7:
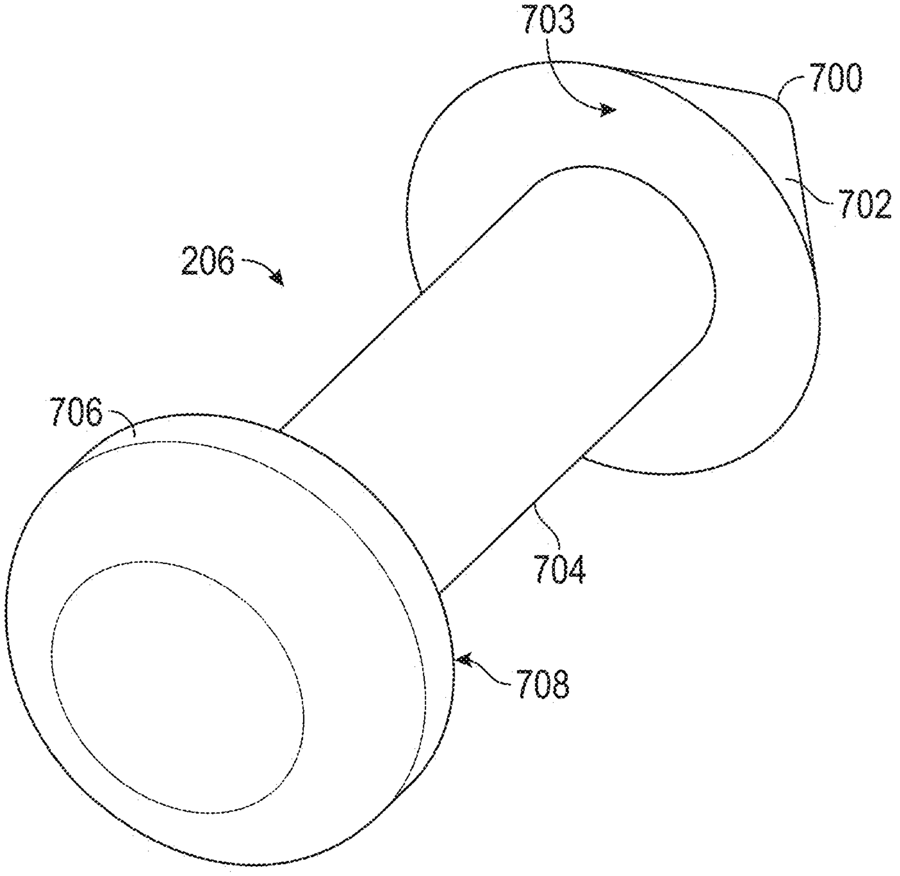
FIG. 7 illustrates another example of a fastener.

As illustrated in FIG. 7, the tack 700 can include a puncturing portion 702 which is operable to puncture the tubular structure 12. The exemplary tack 700 does not include as long of a puncturing portion 702 as the puncturing portion 602 as illustrated in FIG. 6. An abutment surface 703 abuts against a surface of the corresponding receiving portion 310 of the ring 300. A body 704 spans the thickness of the wall of the tubular structure 12, and an end 706 includes an abutment surface 708 which abuts against the inner surface of the tubular structure 12. The abutment surfaces 703, 708 prevent the fastener 206 from being removed from the tubular structure 12 and the ring 300.

Figure 8:
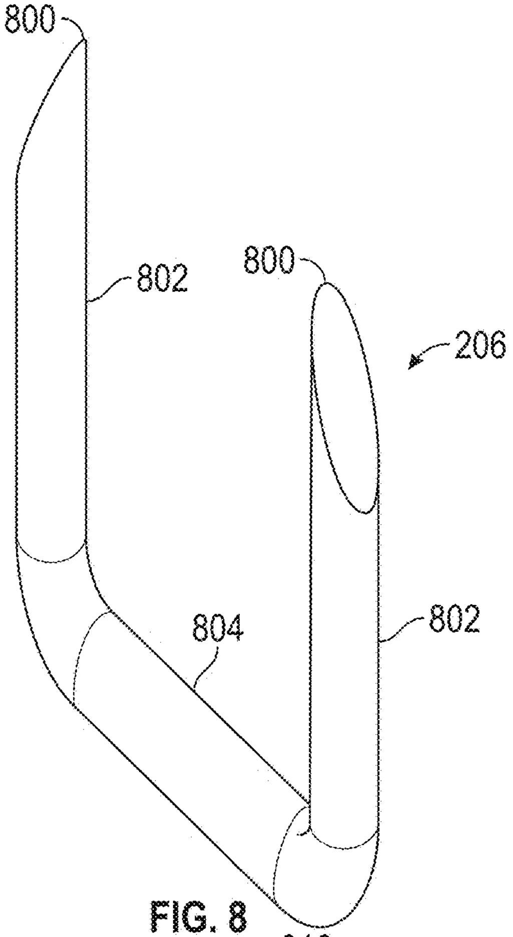
FIG. 8 illustrates another example of a fastener.

As illustrated in FIG. 8, the staple 800 can include two puncturing portions 802 which are operable to puncture through the tubular structure 12 and be received in the corresponding receiving portion 310 of the ring 300. A body 804 spans between the puncturing portions 802 and is operable to abut the inner surface of the tubular structure 12 to prevent the fastener 206 from being removed from the tubular structure 12. In at least one example, the puncturing portions 802 may be operable to bend or deform when received in the receiving portion 310 to prevent the puncturing portions 802 from being removed from the ring 300, ensuring coupling of the tubular structure 12 with the ring 300.

Figure 9:
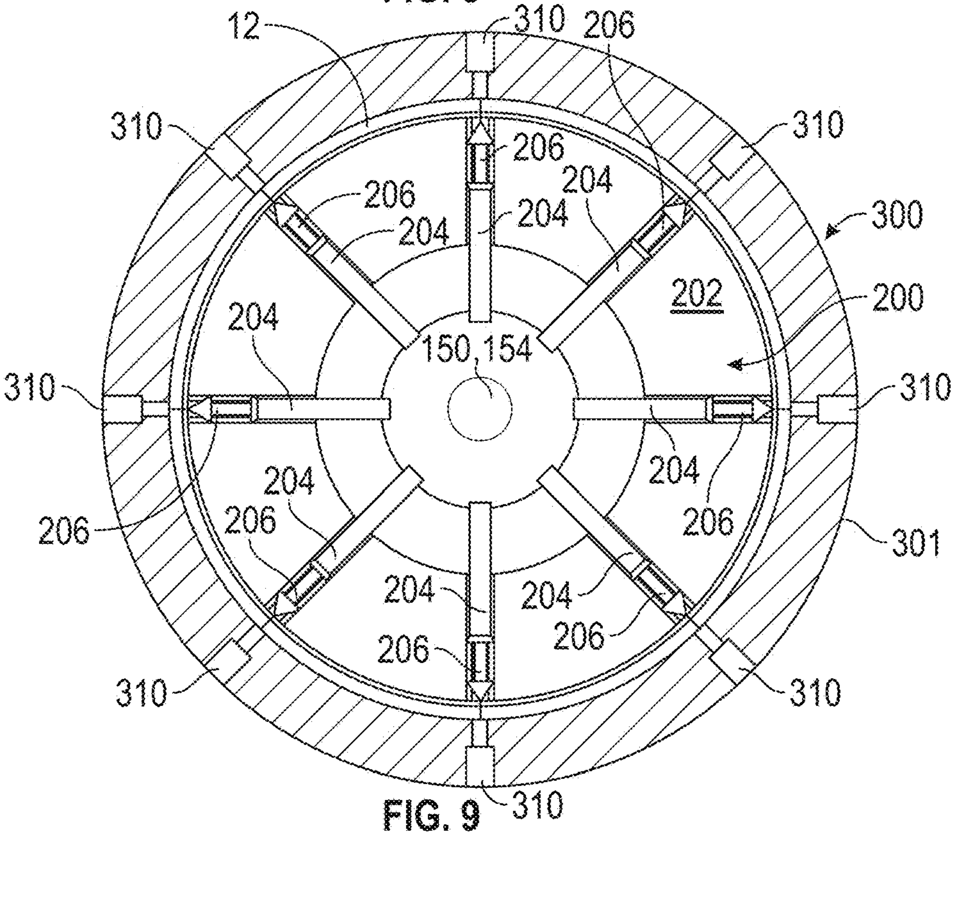
FIG. 9 illustrates a cross-sectional view of the cartridge aligned with the ring.

Referring to FIGS. 5 and 9, the cartridge 200 can include a plurality of drivers 204 corresponding with the plurality of fasteners 206. Upon actuation of the fixation device 100, the drivers 204 activate to push the corresponding fasteners 206 radially outward from the cartridge 200. The drivers 204 may include rods which abut the fasteners 206 and towards the center of the body 202 of the cartridge 200. In some examples, the drivers 204 may be spring loaded.

The pusher rod 150, as illustrated in FIG. 5, is tapered from a front portion 154 with a smaller diameter D1 to a rear portion 152 with a larger diameter D2 which is greater than the smaller diameter D1. The drivers 204 may abut the fasteners 206 on one end while extending into the cartridge 200 so that the opposing end of the fasteners 206 abut the pusher rod 150.

Figure 10A:
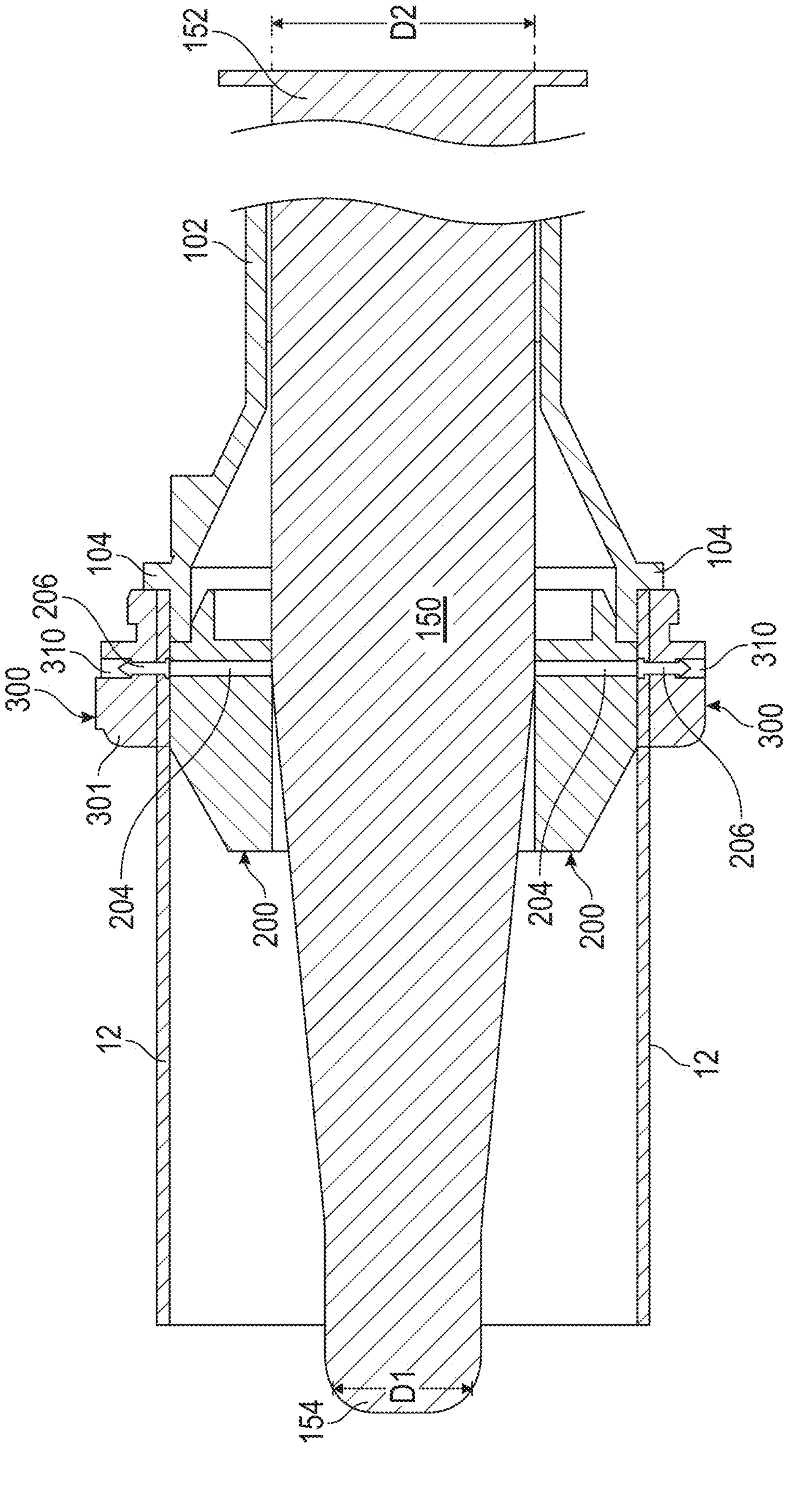
FIG. 10A illustrates actuation of the fixation device.
Figure 10B:
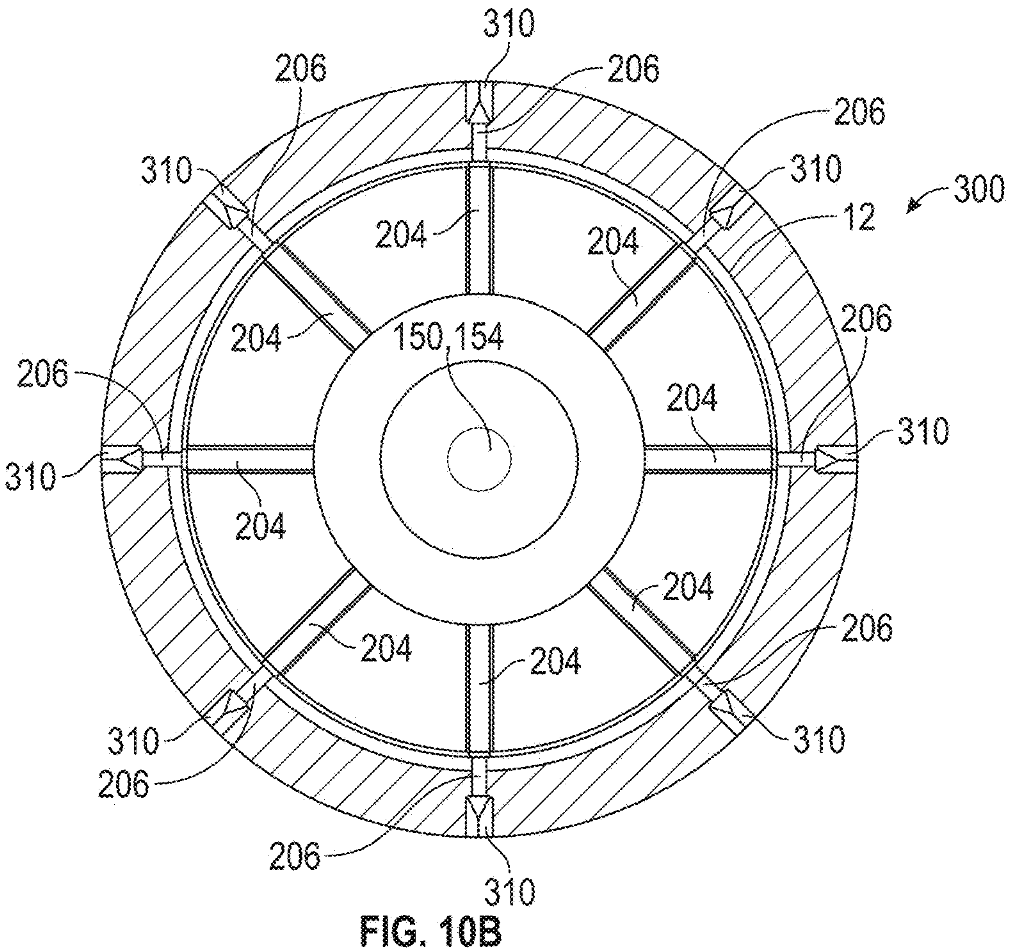
FIG. 10B illustrates a cross-sectional view of FIG. 10A.

Referring to FIGS. 10A and 101B, the fixation device 100 is actuated. Actuation of the fixation device 100 can include translating the pusher rod 150 along the longitudinal axis through the cartridge 200 from the front portion 154 towards the rear portion 152. The pusher rod 150, increasing in thickness, then activates the drivers 204 to drive the fasteners 206 radially outward from the cartridge 200, through the tubular structure 12, and into the receiving portions 310 of the ring 300. Once the ring 300 is coupled with the tubular structure 12, the fixation device 100 can be removed from the tubular structure 12. The ring 300 is then affixed or secured to the end of the tubular structure 12, maintaining the structure of the lumen of the tubular structure 12.

The fixation device 100, the ring 300, and/or the fasteners 206 can be made from mechanically suitable materials that are approved, and have sufficient strength, for use in the human or animal body. For example, the following materials, alone or in any combination, can be used: metals, in particular titanium or stainless steel, including the special alloys used for implants and medical instruments, nitinol, carbon materials, including carbon fiber meshes, soft plastic, for example silicone, hard plastic, for example Teflon, ceramic material, and/or bioresorbable material. The fixation device 100, the ring 300, and/or the fasteners 206 can be provided entirely or partially with a coating and/or structure that prevents or at least reduces the adherence of blood constituents. Such a coating can be composed of a material that smooths the surface. In at least one example, the coating can also contain anti-thrombotic medicaments (e.g. heparin).

Figure 11:
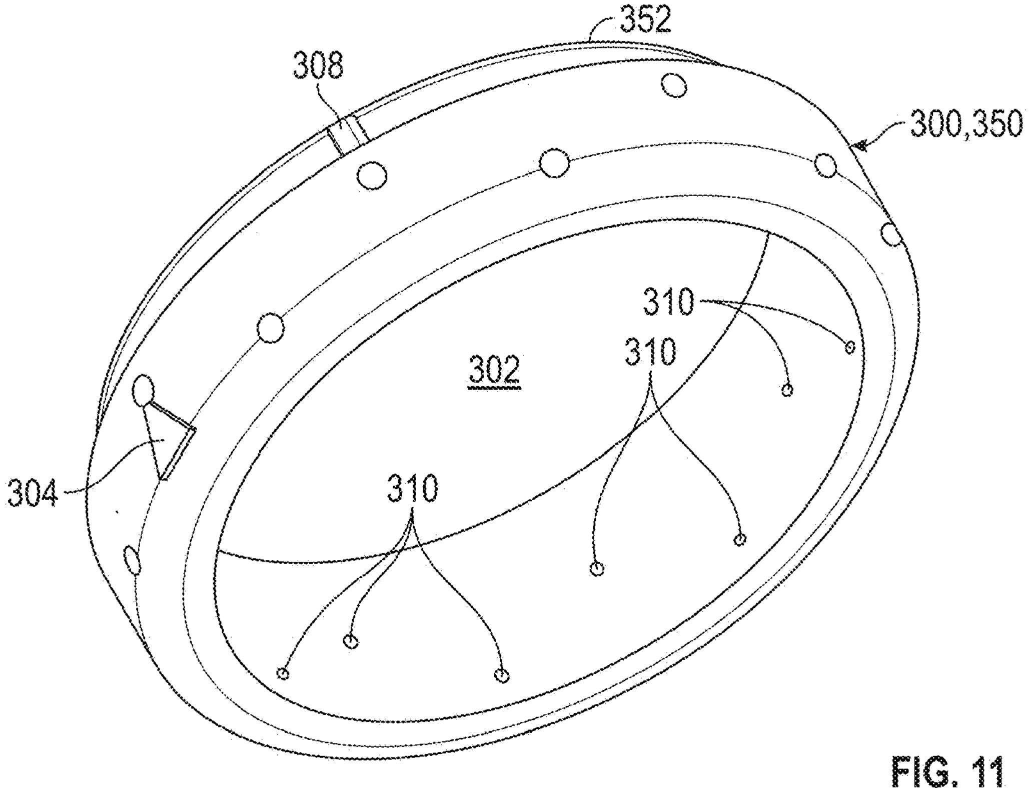
FIG. 11 illustrates an exemplary ring.
Figure 12:
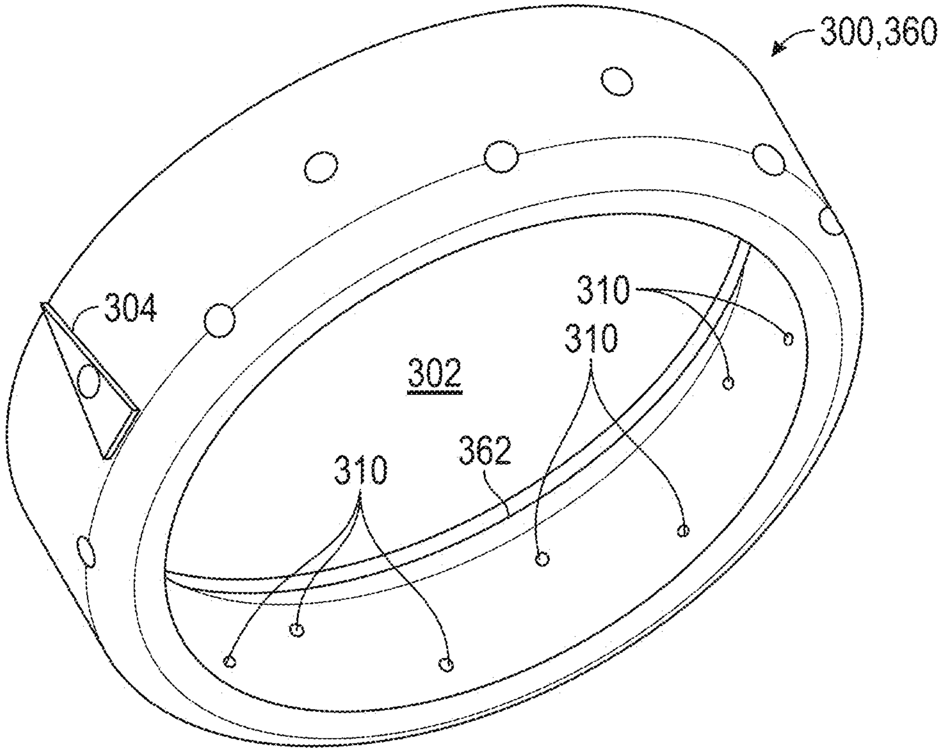
FIG. 12 illustrates an example of another ring.

The above process of coupling the ring 300 with the tubular structure 12 can be repeated for a second tubular structure 12 with a second ring 300. For example, FIG. 11 illustrates an exemplary male ring 350, and FIG. 12 illustrates an exemplary corresponding female ring 350. Similar to the ring 300 discussed above, the male ring 350 and the female ring 360 each include an aperture 302 operable to receive a tubular structure 12, receiving portions 310 operable to receive the fasteners 206, and alignment portions 304, 308. The male ring 350 includes a mating portion 352, and the female ring 360 includes a corresponding mating portion 362. The mating portion 352 is operable to couple with the mating portion 362 to couple the male ring 350 and the female ring 360 with one another. As illustrated in FIGS. 11 and 12, the mating portion 352 of the male ring 350 extends from the ring 350 and is operable to be received by the mating portion 362 of the female ring 360. In some examples, the rings 300 can be coupled with one another by, for example, fastening, snapping, clamping, stenting, tacking, pinning, loop and hook, adhesive, and/or other connecting method so long as the rings 300 are securely coupled with one another.

Figure 13:
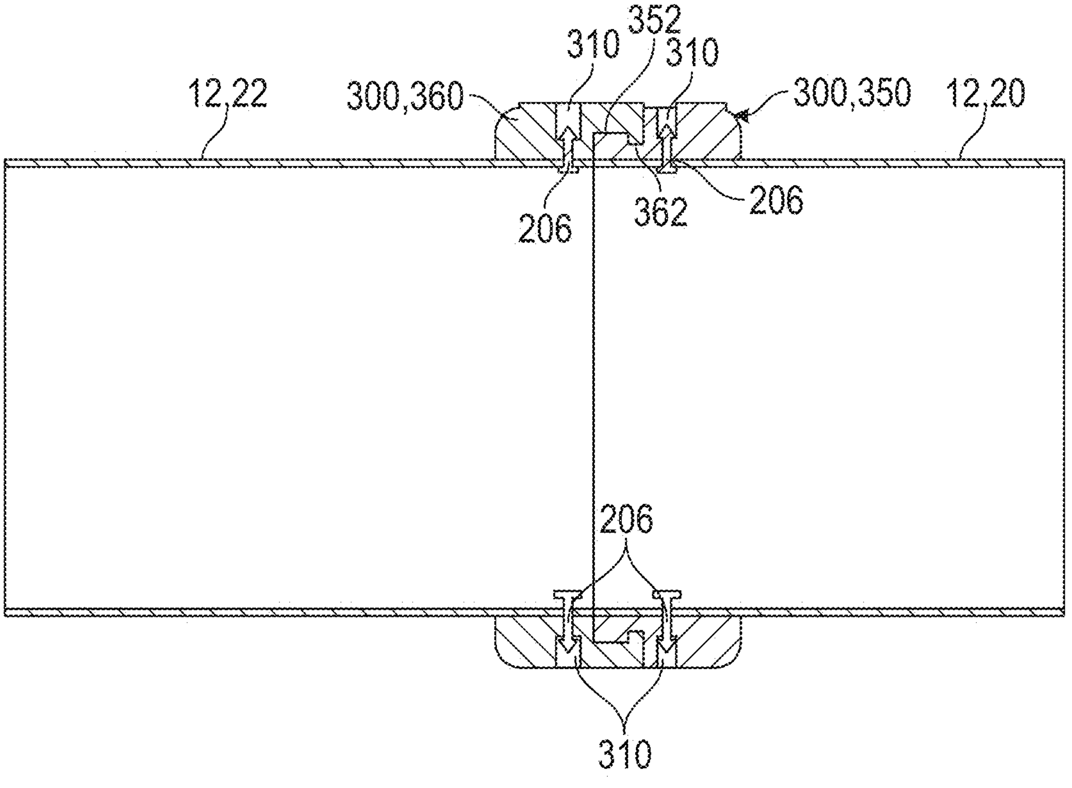
FIG. 13 illustrates a cross-sectional view of two rings coupled with one another to join two tubular structures.

As illustrated in FIG. 13, when the rings 350, 360 are coupled with one another, the lumens 14 of the two tubular structures 20, 22 are aligned in fluid communication with one another. In at least one example, the rings 350, 360 can create a seal to prevent fluid leakage. Accordingly, the anastomotic coupler 10 provides a more reliable, faster, more secure anastomotic coupling device to create a sealed, leak-proof, open connection between the ends of the tubular structures 20, 22 and allow for "stented" unobstructed flow of luminal contents through the connection/anastomosis (e.g. blood, lymph, fluid, stool contents, gastric contents, etc.). This connection can be strong enough to withstand tension, traction, and high flow pressure, which may occur with distal obstruction.

Figure 14:
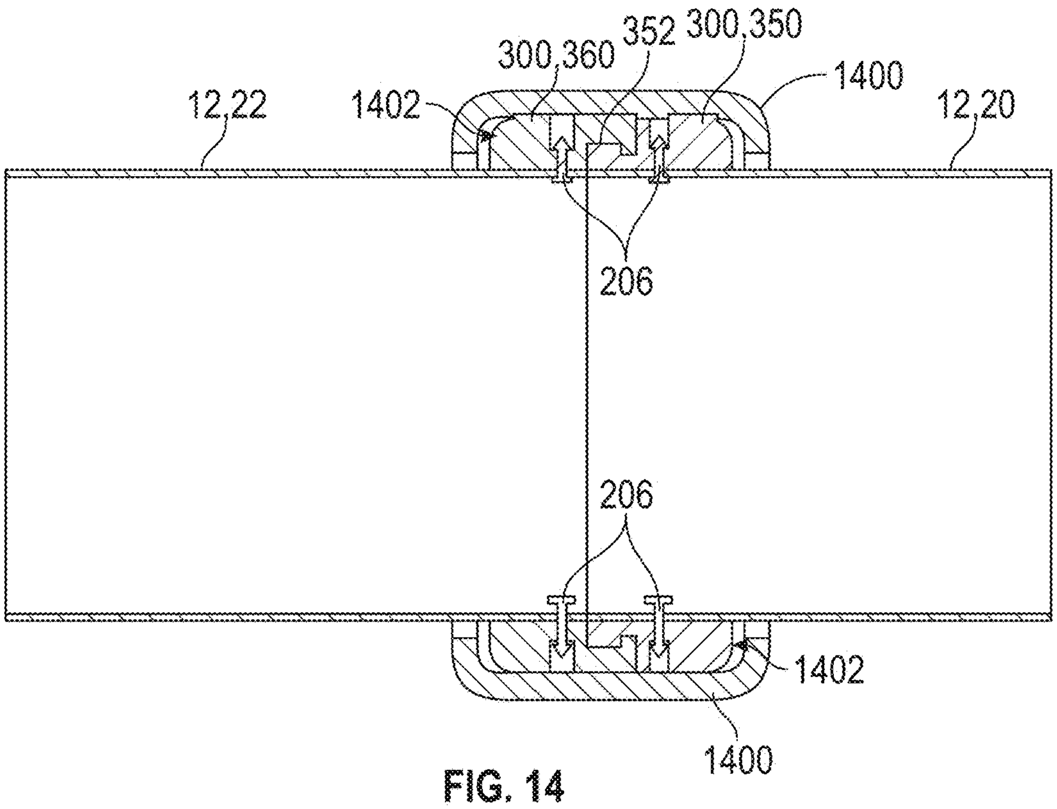
FIG. 14 illustrates a cap disposed over the two rings of FIG. 13.
Figure 15:
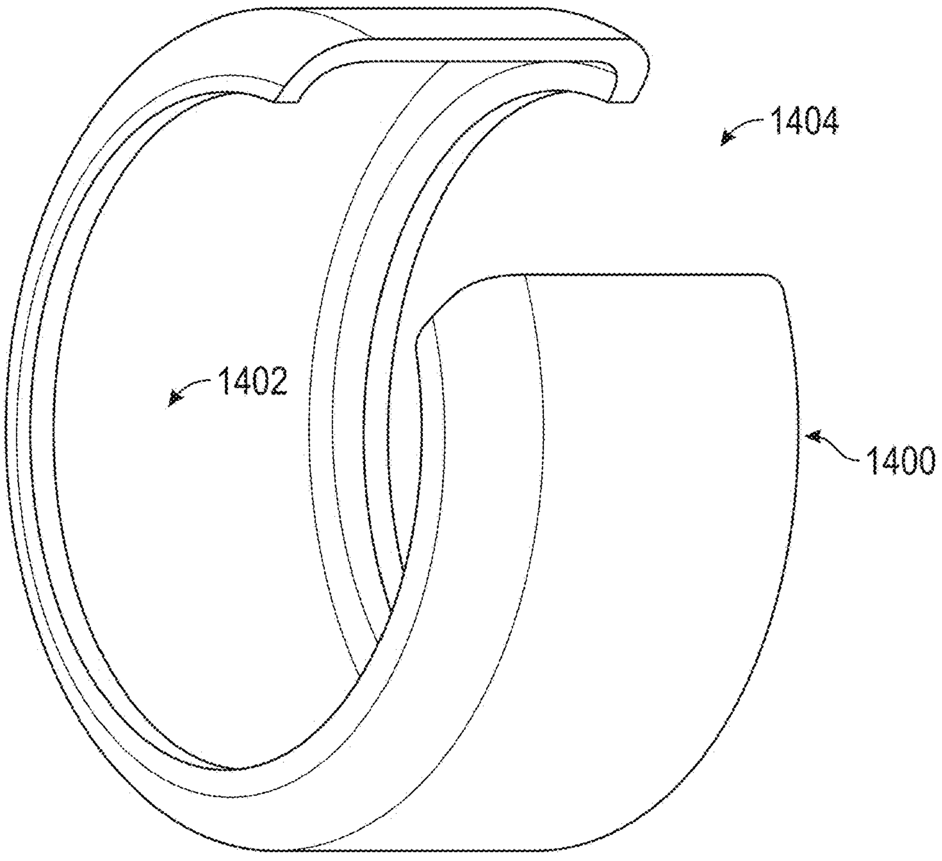
FIG. 15 illustrates an exemplary cap.

As illustrated in FIG. 14, a cap 1400 can be provided over the two rings 350, 360. The cap 1400 can assist in ensuring the connection between the rings 350, 360, as well as protecting the rings 350, 360 from external damage. As illustrated in FIG. 15, the cap 1400 can include a recess 1402 which is operable to receive the two rings 350, 360. An opening 1404 can be formed such that the cap 1400 can be deformed to snap over the two rings 350, 360.

Figure 16:
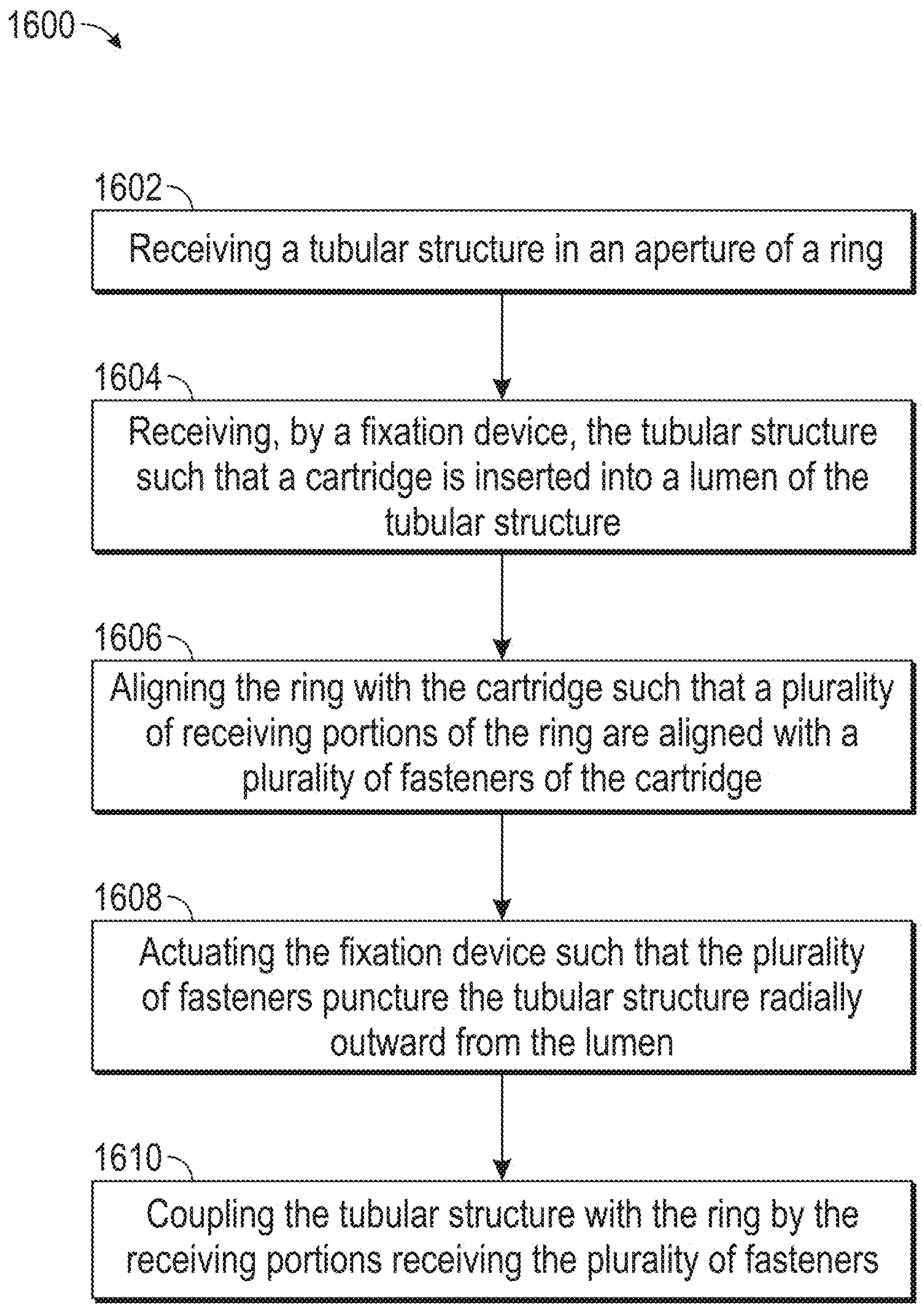
FIG. 16 is a flow chart of a method for utilizing an anastomotic coupler.

Referring to FIG. 16, a flowchart is presented in accordance with an example embodiment. The method 1600 is provided by way of example, as there are a variety of ways to carry out the method. The method 1600 described below can be carried out using the configurations illustrated in FIG. 1-15, for example, and various elements of these figures are referenced in explaining example method 1600. Each block shown in FIG. 16 represents one or more processes, methods or subroutines, carried out in the example method 600. Furthermore, the illustrated order of blocks is illustrative only and the order of the blocks can change according to the present disclosure. Additional blocks may be added or fewer blocks may be utilized, without departing from this disclosure. The example method 1600 can begin at block 1602.

At block 1602, a first tubular structure is received in an aperture of a first ring.

At block 1604, a fixation device receives the first tubular structure such that a first cartridge is inserted into a lumen of the first tubular structure.

At block 1606, the first ring is aligned with the first cartridge such that a plurality of receiving portions of the first ring are aligned with a plurality of fasteners of the first cartridge.

At block 1608, the fixation device is actuated such that the plurality of fasteners puncture the first tubular structure radially outward from the lumen. The cartridge can include a plurality of drivers corresponding with the plurality of fasteners. Upon actuation of the fixation device, the drivers activate to push the corresponding fasteners radially outward from the cartridge. In at least one example, the fixation device can include a pusher rod. The pusher rod can be tapered from a front portion with a smaller diameter to rear portion with a larger diameter. Upon actuation of the fixation device, the pusher rod can translate along a longitudinal axis to activate the drivers. In at least one example, to activate the drivers, the pusher rod translates along the longitudinal axis and passes through the cartridge from the front portion to the rear portion such that the pusher rod abuts and pushes the drivers and the corresponding fasteners radially outward from the cartridge.

At block 1610, the first tubular structure is coupled with the first ring by the receiving portions receiving the plurality of fasteners.

In at least one example, a second tubular structure can be received in an aperture of a second ring. A fixation device can receive the second tubular structure such that a second cartridge is inserted into a lumen of the second tubular structure. In at least one example, the fixation device may be the same fixation device that was utilized for the first ring. In some examples, the fixation device may be the same fixation device utilized for the first ring with a second cartridge that replaced the first cartridge. In some examples, the fixation device may be a second fixation device. The second ring can be aligned with the second cartridge such that a plurality of receiving portions of the second ring are aligned with a plurality of fasteners of the second cartridge. The fixation device can be actuated such that the plurality of fasteners puncture the second tubular structure radially outward from the lumen. The second tubular structure can be coupled with the second ring by the receiving portions receiving the plurality of fasteners.

The first ring can be aligned with the second ring such that the lumen of the first tubular structure and the lumen of the second tubular structure are aligned in fluid communication with one another. The first ring can be coupled with the second ring to join the first tubular structure with the second tubular structure, providing a continuous passage between the first tubular structure and the second tubular structure. In at least one example, a cap can be positioned about the first and the second ring to ensure the connection between the first ring and the second ring.

Figure 17A:
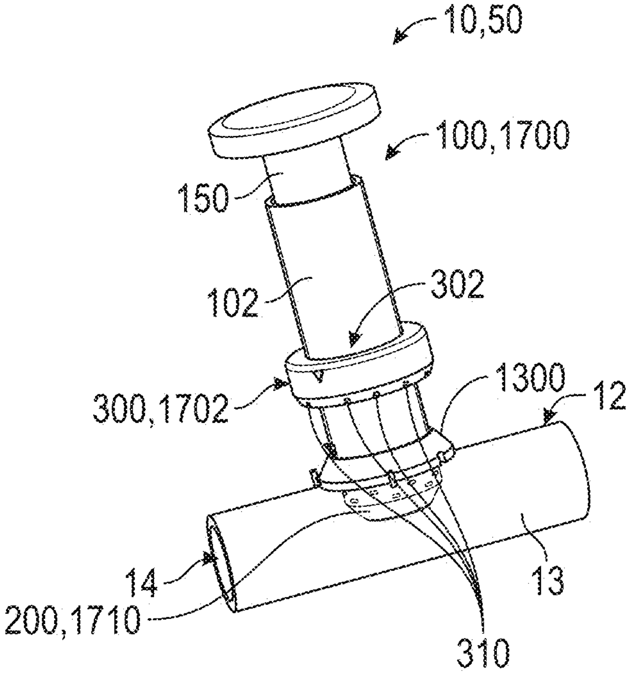
FIG. 17A illustrates a fixation device engaging with a side hole of a tubular structure.

FIGS. 17A-17E illustrate examples of an anastomotic coupler 10 which is operable to couple an end of a tubular structure 12 with a side of a tubular structure 12. Elements described in the system of FIGS. 17A-18 that have similar or the same name and/or the same reference numbers as elements in the disclosure for FIGS. 1-16 may have the same features as discussed above. While the discussion below for FIGS. 17A-17E may highlight some differences in features, the disclosure for the system of FIGS. 17A-18 are not limited to those and may also include any and/or all of the features as discussed above.

FIG. 17A illustrates alignment and positioning of a fixation device 100 and a ring 300 on a tubular structure 12. The fixation device 100 and the ring 300 are positioned such that the ring 300 can be coupled to the tubular structure 12 where an aperture 302 of the ring 300 can be aligned with a hole 1300 formed in a wall 13 of the tubular structure 12. In other words, the tubular structure 12 has a hole 1300 formed in a side wall 13. In at least one example, a cutting mechanism (not shown) can be operable to cut the hole 1300 in the wall 13 of the tubular structure 12. In some examples, the cutting mechanism can be a separate component operable to cut a precise hole 1300 in the wall 13 of the tubular structure 12. In some examples, the cutting mechanism can be part of the fixation device 1700 such that only one component is needed in the fixation device 1700 to cut a hole 1300 and couple the ring 300 to the tubular structure 12. The cutting mechanism can create a symmetrical, controllable-sized opening in the side wall 13 of the tubular structure 12.

In at least one example, the fixation device 1700 can be similar to fixation device 100 as discussed herein. In some examples, fixation device 1700 may be modified to couple the ring 1702 to the wall 13 of the tubular structure 12 to align with the hole 1300 in the wall 13 instead of coupling the ring 1702 to the tubular structure 12 in line with the lumen 14 of the tubular structure. In at least one example, the fixation device 1700 can include a stop which extends radially from the housing 102 such that the wall 13 of the tubular structure 12 abuts the stop. Accordingly, the fixation device 1700 provides guidance to the user for when the fixation device 1700 is in a desired position. In some examples, the stop can include a plurality of alignment components corresponding with alignment components of the ring 1702. As such, when the ring 1702 is aligned, the alignment components of the stop are aligned with the alignment components of the ring 1702.

Figure 17B:
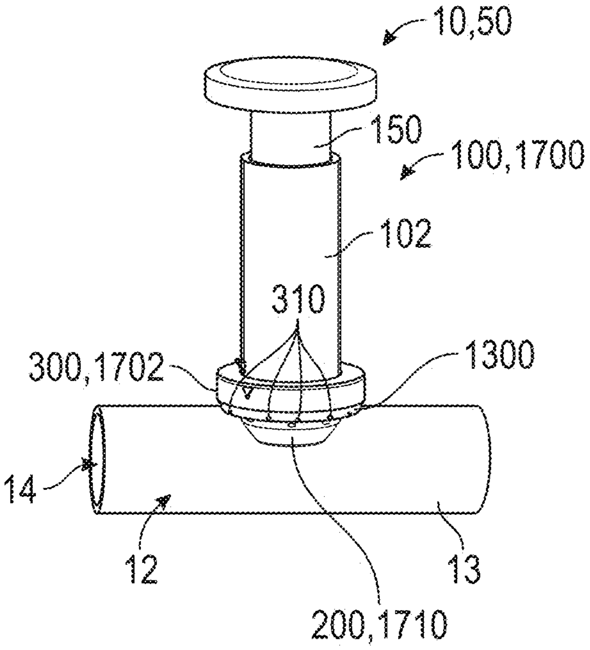
FIG. 17B illustrates a ring being aligned on the tubular structure of FIG. 17A.

As illustrated in FIGS. 17A and 17B, a cartridge 1710 can be disposed within the lumen 14 of the tubular structure 12. The cartridge 1710, similar to cartridge 300, includes a plurality of fasteners 260 (for example shown in 17C-17E) operable to be received in corresponding plurality of receiving portions 310 in the ring 300. The ring 1702, as illustrated in FIGS. 17A-17E has a cylindrical shape. However, in other examples, the ring 1702 can have any suitable shape such that the ring 1702 can be aligned with the hole 1300 and prevent leakage between the tubular structure 12 and the ring 1702. The ring 1702, in some examples, may include a sealing component operable to abut against the wall 13 of the tubular structure 12 to prevent leakage of fluid.

In some examples, the position of the receiving portions 310 in the ring 1702 may be adjusted to better receive the plurality of fasteners 260 and provide a stronger coupling between the ring 1702 and the tubular structure 12. For example, as illustrated in FIGS. 17A-17E, the receiving portions 310 may be disposed towards the bottom of the ring 1702 so that the receiving portions 310 are adjacent to the tubular structure 12.

Similarly, in some examples, the position of the fasteners 260 in the cartridge 1710 may be adjusted towards the top to be adjacent to the wall 13 of the tubular structure 12. Accordingly, the distance between the fasteners 260 in the cartridge 1710 and the receiving portions 310 can be smaller to minimize the chance of error in coupling the ring 1702 with the tubular structure 12.

Figure 17C:
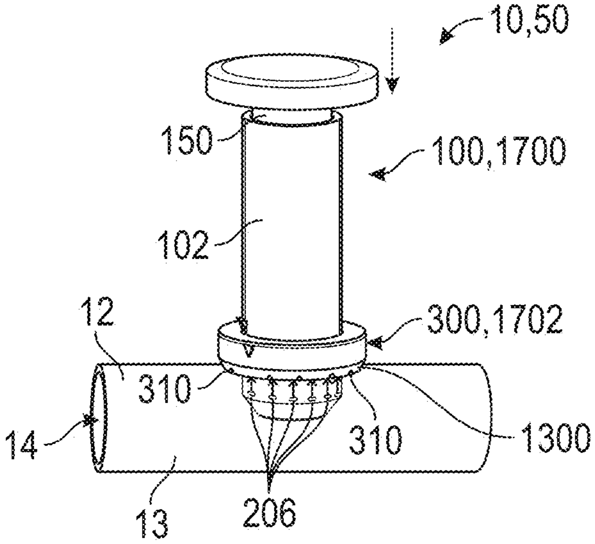
FIG. 17C illustrates actuation of the fixation device.
Figure 18:
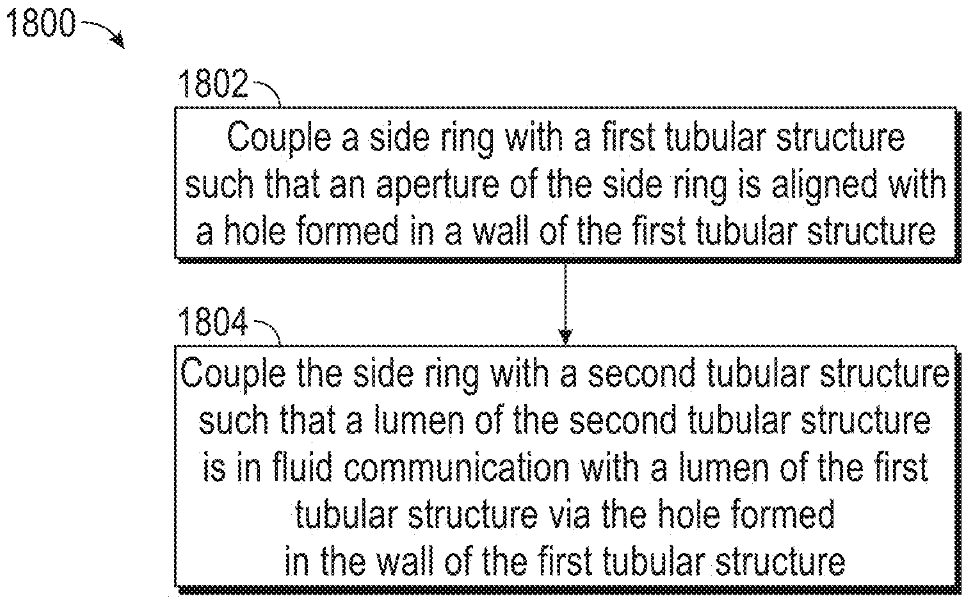
FIG. 18 is a flow chart of a method for coupling an end of a tubular structure with a side of a tubular structure.

As illustrated in FIG. 17A-17C, the ring 1702 can be positioned opposite the cartridge 1710 in relation to the wall 13 of the tubular structure 12. The ring 1702 can be positioned external of the tubular structure 12 so that the ring 1702 does not cause any obstruction in the lumen 14 of the tubular structure 12. The cartridge 1710, as illustrated in FIGS. 17A-17C, can be positioned inside the lumen 14 of the tubular structure 12 to push the fasteners 260 across the wall 13 of the tubular structure 12 into the receiving portions 310 of the ring 1702. In some examples, the cartridge 1710 may also be positioned external of the tubular structure 12, so long as the fasteners 260 can couple the ring 1702 with the tubular structure 12.

As illustrated in FIGS. 17C, the fixation device 1700 can be actuated so that the plurality of fasteners 260 puncture the tubular structure 12 and are received by the receiving portions 310. Accordingly, the tubular structure 12 can be coupled with the ring 1702. In at least one example, as illustrated in FIG. 17C, the fixation device 1700 can include a pusher rod 150. Upon actuation of the fixation device 1700, the pusher rod 150 can translate along a longitudinal axis to activate drivers to push the corresponding fasteners 260 from the cartridge 1710. In some examples, the fixation device 1700 can have any suitable mechanism to activate the drivers to push the fasteners 260 from the cartridge 1710.

Figure 17D:
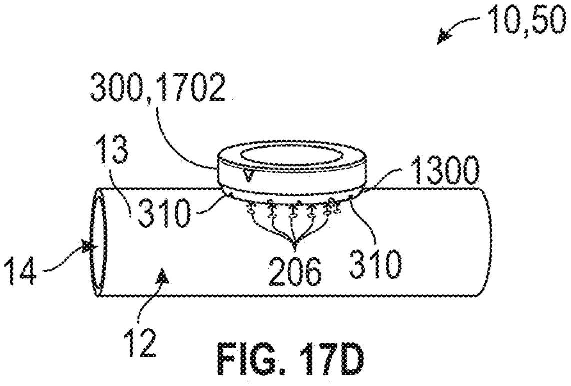
FIG. 17D illustrates the ring being coupled with the side of the tubular structure.

As illustrated in FIG. 17D, after the ring 1702 is coupled with the tubular structure 12, the fixation device 1700, along with the cartridge 1710, can be removed. The ring 1702 remains coupled with the tubular structure 12 such that the aperture 302 of the ring 1702 is aligned with the hole 1300 in the wall 13 of the tubular structure 12.

Figure 17E:
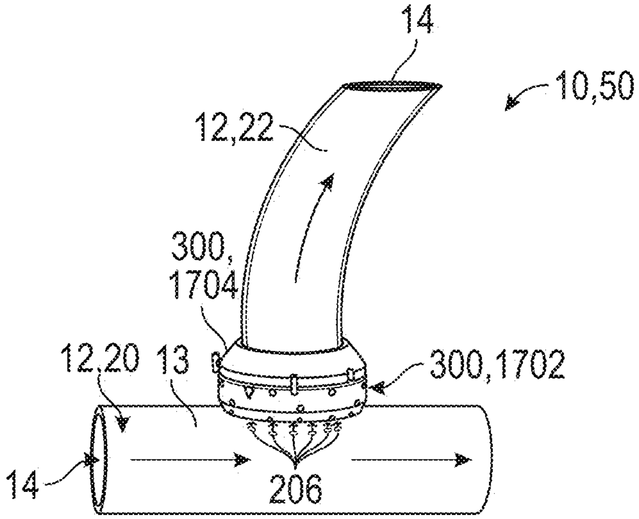
FIG. 17E illustrates a second tubular structure being coupled with the tubular structure.

As illustrated in FIG. 17E, the ring 1702 is operable to be coupled with a second tubular structure 22 such that a lumen 14 of the second tubular structure 22 is in fluid communication with the lumen 14 of the tubular structure 20 via the hole 1300 formed in the wall 13 of the tubular structure 20. The side ring 1702 is operable to be coupled with the first tubular structure 20 such that the aperture 302 of the side ring 1702 is aligned with the hole 1300 formed in the wall 13 of the first tubular structure 12. The end ring 1704, similar to the rings 350, 360 as illustrated in FIGS. 1-14, is operable to be coupled with a second tubular structure 22 such that the aperture 302 of the end ring 1704 is in line with the lumen 14 of the second tubular structure 22. The side ring 1702 is operable to be coupled with the end ring 1704 such that the lumen 14 of the second tubular structure 22 is in fluid communication with the lumen 14 of the first tubular structure 20 via the hole 1300 formed in the wall 13 of the first tubular structure 20. Accordingly, an end-to-side anastomosis is achieved. In some examples, the side ring 1702 and the end ring 1704 create a seal to prevent fluid leakage. The seal can be achieved by any suitable mechanism.

As illustrated in FIG. 17E, fluid may flow through the lumen 14 of the first tubular structure 20 while some fluid may flow into and through the lumen 14 of the second tubular structure 22. In some examples, fluid from the second tubular structure 22 may flow into the first tubular structure 20.

The aforementioned side-to-end anastomotic coupler 50 and system provides users with a better, more reliable alternative to the conventional techniques. The only technique conventionally practiced for side-to-end anastomosis is through hand-sewn suture techniques. Hand-sewn suture techniques are labor intensive and prone to failure. Similarly, the process of creating the side opening in the tubular structure is conventionally completed in an uncontrolled fashion using a scalpel or scissors to haphazardly cut the side of the structure, which can result in an asymmetric opening of variable size.

Referring to FIG. 18, a flowchart is presented in accordance with an example embodiment. The method 1800 is provided by way of example, as there are a variety of ways to carry out the method. The method 1800 described below can be carried out using the configurations illustrated in FIG. 1-17E, for example, and various elements of these figures are referenced in explaining example method 1800. Each block shown in FIG. 18 represents one or more processes, methods or subroutines, carried out in the example method 1800. Furthermore, the illustrated order of blocks is illustrative only and the order of the blocks can change according to the present disclosure. Additional blocks may be added or fewer blocks may be utilized, without departing from this disclosure. The example method 1800 can begin at block 1802.

At block 1802, a side ring is coupled with a first tubular structure such that an aperture of the side ring is aligned with a hole formed in a wall of the first tubular structure.

At block 1804, the side ring is coupled with a second tubular structure such that a lumen of the second tubular structure is in fluid communication with a lumen of the first tubular structure via the hole formed in the wall of the first tubular structure. In at least one example, the second tubular structure can be coupled with an end ring such that an aperture of the end ring is in line with the lumen of the second tubular structure. The side ring can be coupled with the end ring to join the first tubular structure with the second tubular structure. In at least one example, the side ring and the end ring can create a seal to prevent fluid leakage.

FIGS. 19-25C illustrate examples of an anastomotic coupler 10 which is operable to couple two tubular structures 12 with a cartridge 200 having fasteners 206 extending therefrom at an angle 1902A. Elements described in the system of FIGS. 19-25C that have similar or the same name and/or the same reference numbers as elements in the disclosure for FIGS. 1-18 may have the same features and/or functions as discussed above. While the discussion below for FIGS. 19-25C may highlight some differences in features, the disclosure for the system of FIGS. 19-25C are not limited to those and may also include any and/or all of the features as discussed above. Similarly, the examples in FIGS. 1-18 may utilize any and/or all of the features as discussed below for FIGS. 19-25C.

Figure 19:
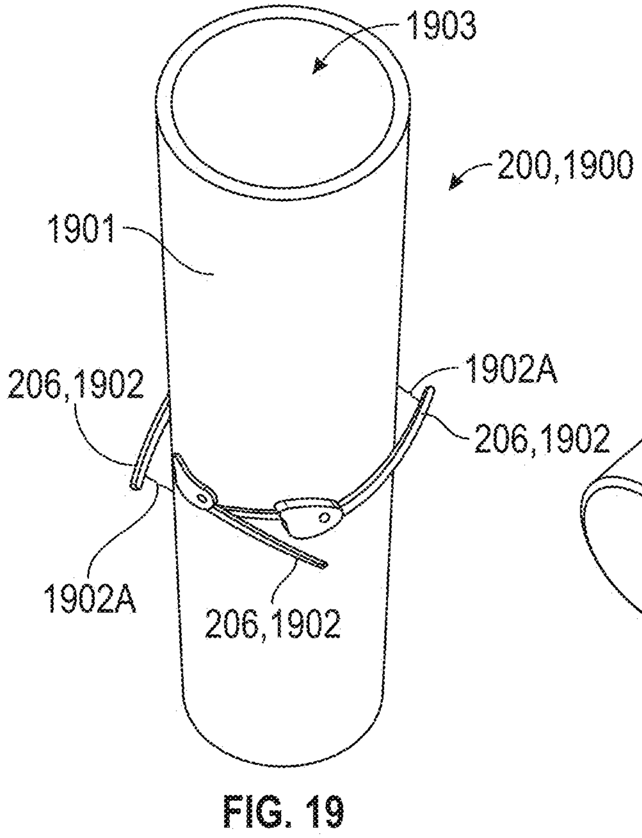
FIG. 19 illustrates an exemplary cartridge.

FIG. 19 illustrates an exemplary cartridge 200, 1900 which includes a body 1901 and fasteners 206, 1902 extending from the body 1901. The body 1901, as illustrated in FIG. 19, can be substantially cylindrical. In other examples, the body 1901 can be in other configurations or shapes such as rectangular, ovoid, or any other suitable shape. In some examples, the body 1901 can include mesh, braided mesh, stent, and may be a solid ring and/or tube, and/or any combination of mesh, stent, and solid material. The body 1901 can form a lumen 1903 which passes through the body 1901. The lumen 1903 is operable to permit fluidic passage across the body 1901 through the lumen 1903. Accordingly, when the cartridge 1900 is disposed within the tubular structure(s) 12, the lumen 1903 is in fluid communication with the lumen 14 of the tubular structure(s) 12 such that fluid can pass through the lumen 1903 between the tubular structure(s) 12.

The fasteners 1902 extend from the body 1901 of the cartridge 1900 at an angle 1902A from the body 1901. For example, the fasteners 1902 may extend at an angle 1902A that is between about 1 degree and about 89 degrees. The fasteners 1902 may extend at an angle 1902 that is greater than 0 degrees and less than 90 degrees. In such an example, the fasteners 1902 may be deployed by rotating the fasteners 1902 in relation to the tubular structure 12. In some examples, the fasteners 1902 may extend at an angle 1902A of 90 degrees (directly radially outward similar to FIGS. 1-18), and may be actuated by expansion of the body 1901 of the cartridge 200. The fasteners 1902 are operable to puncture through a wall of one and/or two tubular structure (s) 12. In some examples, the fasteners 1902 can have a hook design.

In at least one example, as illustrated in FIG. 19, the fasteners 1902 can be coupled to the body 1901 of the cartridge 1900. In some examples, as illustrated in FIGS. 22A-25C, the fasteners 1902 can be formed as a part of the body 1901 such that the fasteners 1902 and the body 1901 are one unitary piece and/or material.

Figure 20:
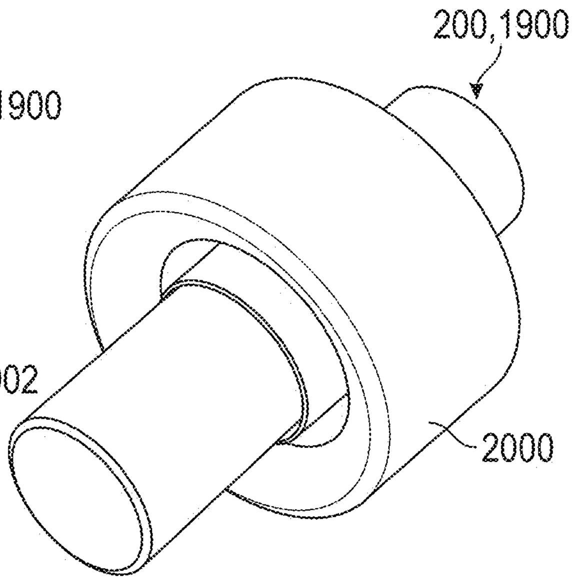
FIG. 20 illustrates the cartridge of FIG. 19 with a sheath covering the fasteners.

FIG. 20 illustrates a sheath 2000 operable to cover the fasteners 1902. Accordingly, upon insertion of the cartridge 1900 into the tubular structure 12, the fasteners 1902 are not inadvertently scratching and/or puncturing the tubular structure 12.

As the fasteners 1902 extend at an angle 1902A from the body 1901, the fasteners 1902 are operable to puncture through the tubular structure 12 when the cartridge 1900 is rotated about a longitudinal axis in relation to the tubular structure 12. Due to the fasteners 1902 puncturing the tubular structure 12 at an angle, the fasteners 1902 couple the cartridge 1900 with the tubular structure 12 so that the fasteners 1902 are not easily removed. For example, the tubular structure 12 or the cartridge 1900 would have to move relative to one another at a specification rotation and distance from one another to de-couple the fasteners 1902 from the tubular structure 1900.

Figure 21A:
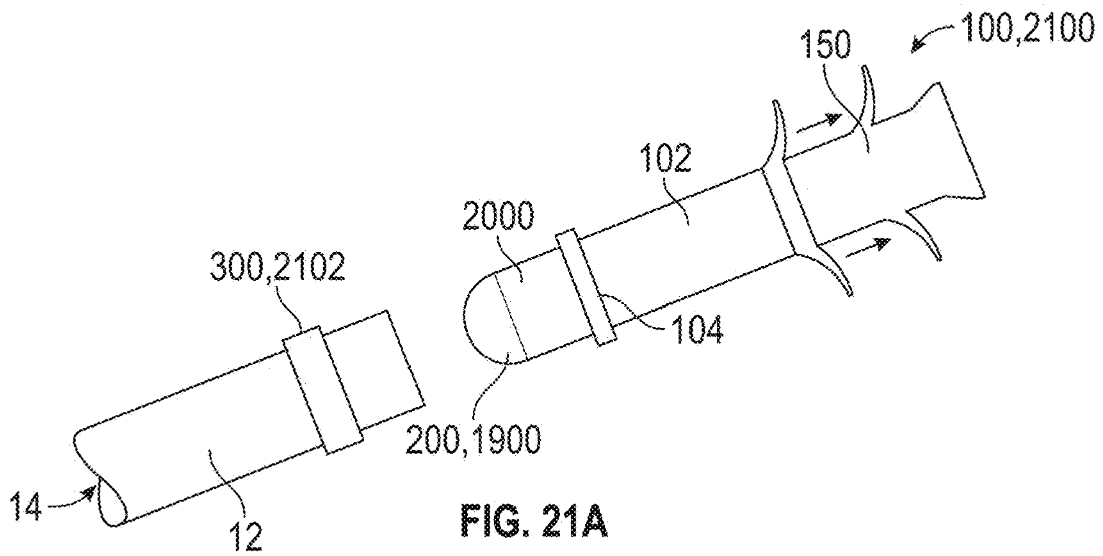
FIGS. 21A, 21B, and 21C illustrate actuation of a fixation device.
Figure 21B:
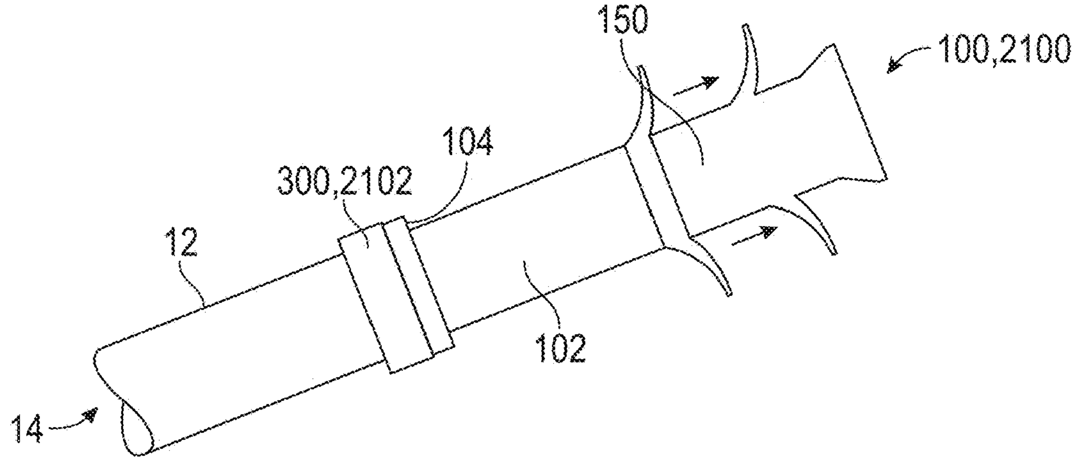
Figure 21C:
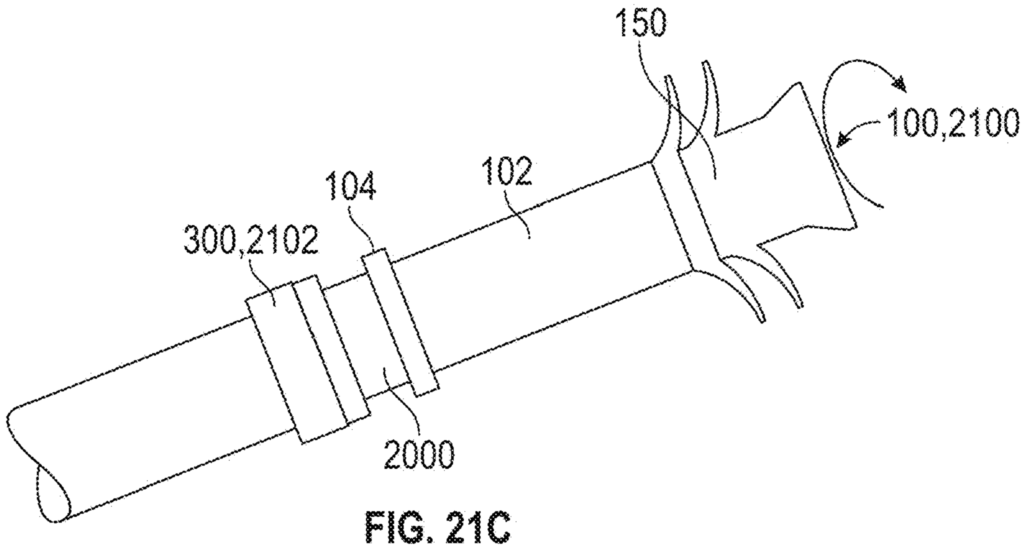

FIGS. 21A-21C illustrate an example of actuation of the cartridge 1900 to couple the cartridge 1900 with a tubular structure 12. The anastomotic coupler 10, in the example illustrated in FIGS. 21A-21C, can include a fixation device 100, 2100. The fixation device 100, 2100 can be similar to the fixation device 100 described above for FIGS. 1-18. A ring 300, 2102 can be provided about the tubular structure 12, external the annulus 14. The fixation device 2100 includes a housing 102 and an actuation mechanism 150, for example a pusher rod, a button, a motor, and/or any other suitable mechanism to actuate the cartridge 1900. The cartridge 1900 can be coupled with the fixation device 2100. A stop 104 can be positioned on the housing 102 adjacent to the cartridge 1900. As shown in FIG. 21B, the stop 104 is operable to abut against the edge of a tubular structure 12 to ensure accurate positioning of the cartridge 1900 within the annulus 14 of the tubular structure 12. As illustrated in FIG. 21B, the cartridge 1900 is inserted into the annulus 14 of the tubular structure 12. In at least one example, the ring 2102 can abut the stop 104 to accurately position the ring 2102 to be aligned with the cartridge 1900.

While the examples illustrated in FIGS. 21A-25C illustrate the cartridge 1900 being disposed within the annulus 14 and the ring 2102 disposed external the tubular structure 12, in other examples the cartridge 1900 can be disposed external the tubular structure 12 while the ring 2102 is disposed within the annulus 14.

As shown in FIG. 21B, the actuation mechanism 150 can be actuated, for example pulled away from the housing 102, to move the sheath 2000 to expose the fasteners 1902. Other mechanisms to remove the sheath 2000 to expose the fasteners 1902 can be utilized, for example pulling a string, cutting apart the sheath 2000, or any other suitable mechanism to expose the fasteners 1902 of the cartridge 1900 after the cartridge 1900 has been disposed within the annulus 104 of the tubular structure 102.

As illustrated in FIG. 21C, the actuation mechanism 150 can be actuated, for example rotated or push a button or any other suitable mechanism, to rotate the cartridge 1900 and puncture the tubular structure 12 with the fasteners 1902. The fasteners 1902 are operable to be rotated to engage the tubular structure 12, as the fasteners 1902 extend at the angle 1902A from the body 1901 of the cartridge 1900.

In some examples, the cartridge 1900 can also expand radially to push the body 1901 of the cartridge 1900 and subsequently the fasteners 1902 against the tubular structure 12. In some examples, the body 1901 of the cartridge 1900 and/or the fasteners 1902 can expand radially by expansion, rotation, balloon expansion, traction, compression, and/or any other suitable mechanism. By pushing the fasteners 1902 against the tubular structure 12, the fasteners 1902 may puncture the tubular structure 12. In some examples, the cartridge 1900 and/or the fasteners 1902 can be rotated after puncturing the tubular structure 12 to secure the coupling of the cartridge 1900 with the tubular structure 12.

The fasteners 1902 are then secured by and/or in the ring 2102 to maintain the position and coupling of the cartridge 1900 with the tubular structure 12. Examples of the mechanism to retain the fasteners 1902 in the ring 2102 and/or configurations of the cartridge 1900 are illustrated in FIGS. 22A-25C. FIGS. 22A-25C illustrate different mechanisms of utilizing gaskets 2200 as receiving portions for the fasteners 1902.

Figure 22A:
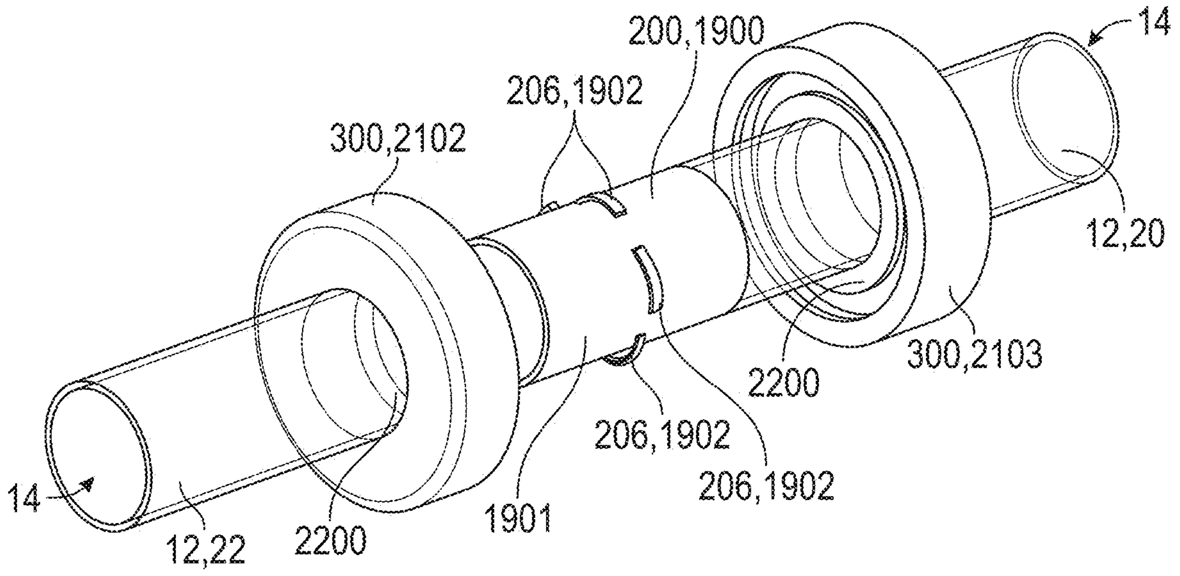
FIGS. 22A, 22B, and 22C illustrate coupling two tubular structures with an exemplary cartridge.
Figure 22B:
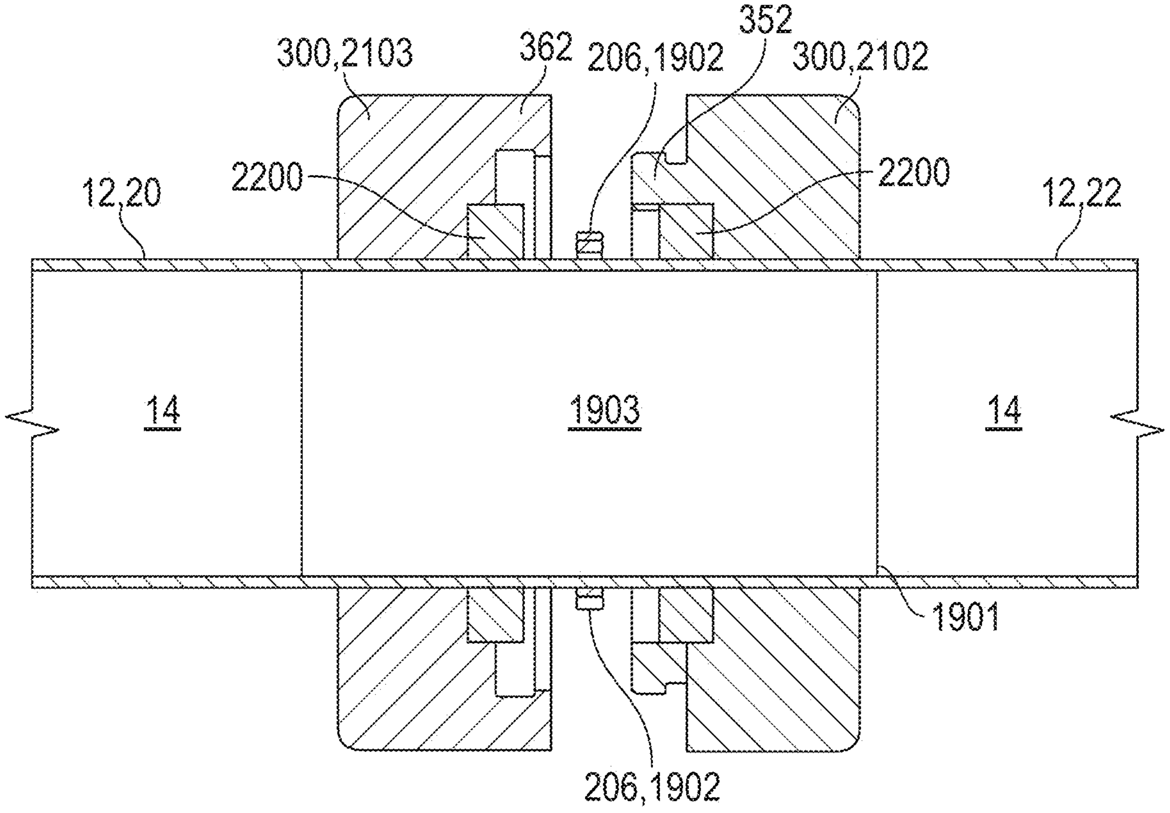
Figure 22C:
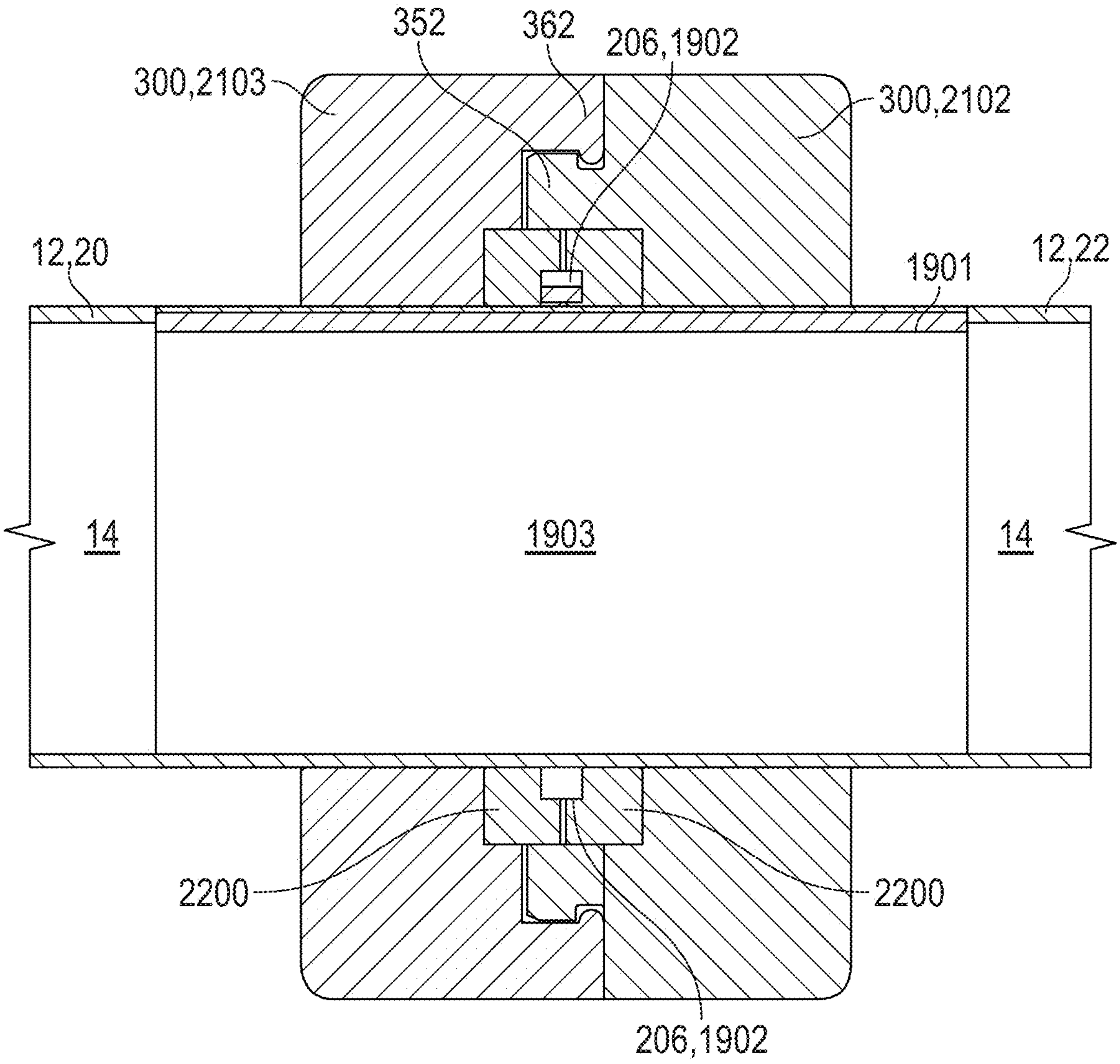

FIGS. 22A-22C illustrate an example of a cartridge 1900 that has one row of fasteners 1902 and rings 300 that secure the fasteners 1902 by compression between two gaskets 2200. To secure two tubular structures 20, 22 to the cartridge 1900, the two tubular structures 20, 22 may overlay one another over the fasteners 1902 of the cartridge 1900. The fasteners 1902 may puncture the two tubular structures 20, 22 to secure the cartridge 1900 against the two tubular structures 20, 22 and align the lumen 14 of each of the tubular structures 20, 22 and the lumen 1903 of the cartridge 1900. Accordingly, fluid can pass through a tubular structure 20, through the cartridge 1900, and to the other tubular structure 22.

As illustrated in FIGS. 22B-22C, the two rings 2102, 2103 can be brought together to couple with one another via mating portions 352, 362 (similar to FIGS. 1-18). Upon coupling of the mating portions 352, 362, gaskets 2200 for each of the rings 2102, 2103 compress against each other, receiving the fasteners 1902 between the two gaskets 2200. In some examples, the compression of the gaskets 2200 against the fasteners 1902 can sufficiently secure the coupling of the rings 2102, 2103 with the cartridge 1900. In some examples, after compression of the gaskets 2200 against the fasteners 1902, the fasteners 1902, the rings 2102, 2103, and/or the gaskets 2200 may be rotated so that the fasteners 1902 puncture into the gaskets 2200. In some examples, the fasteners 1902 may be received by the gaskets 2200 or the ring 2102, 2103. In some examples, the gaskets 2200 can be made of any biocompatible material including silicone, rubber, and other elastomers, including thermoplastic and/or bioresorbable elastomers. In some examples, the gaskets 2200 can be made of polyurethane elastomer, polydiene, poly(vinyl) chloride elastomers, and/or any other suitable material.

Figure 23A:
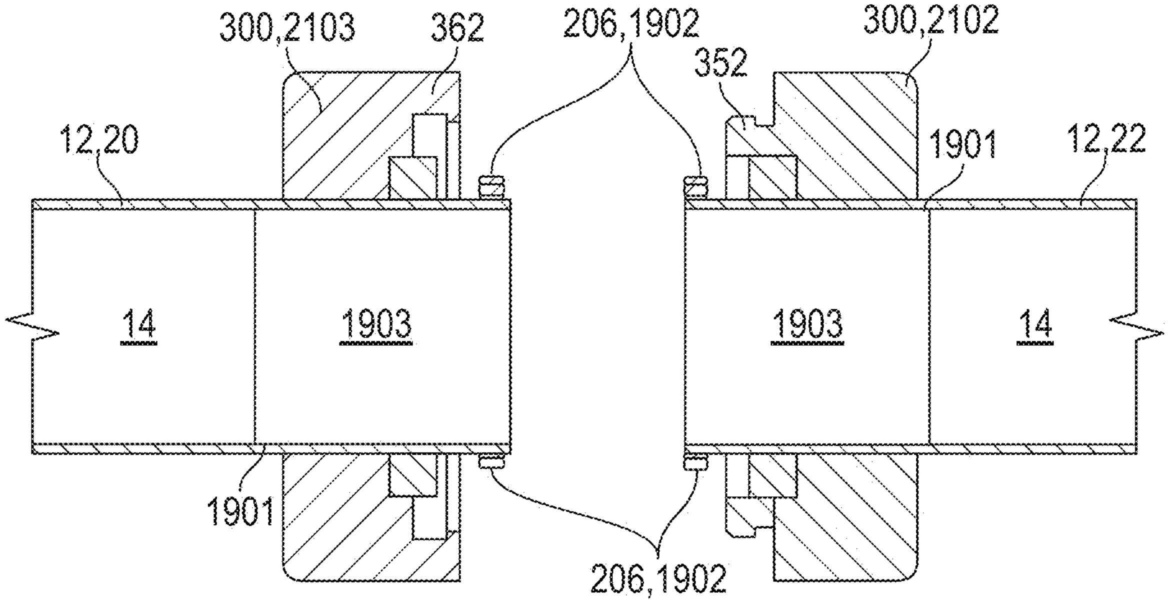
FIGS. 23A, 23B, and 23C illustrate coupling two tubular structures with an exemplary cartridge.
Figure 23B:
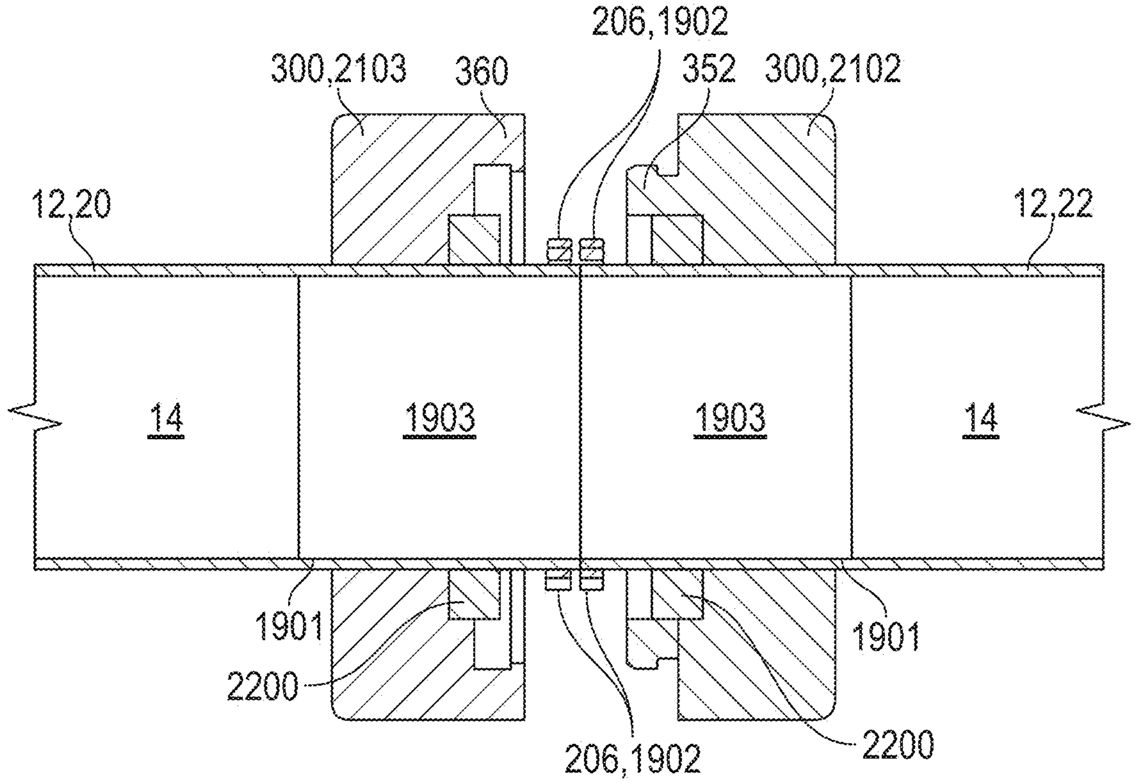
Figure 23C:
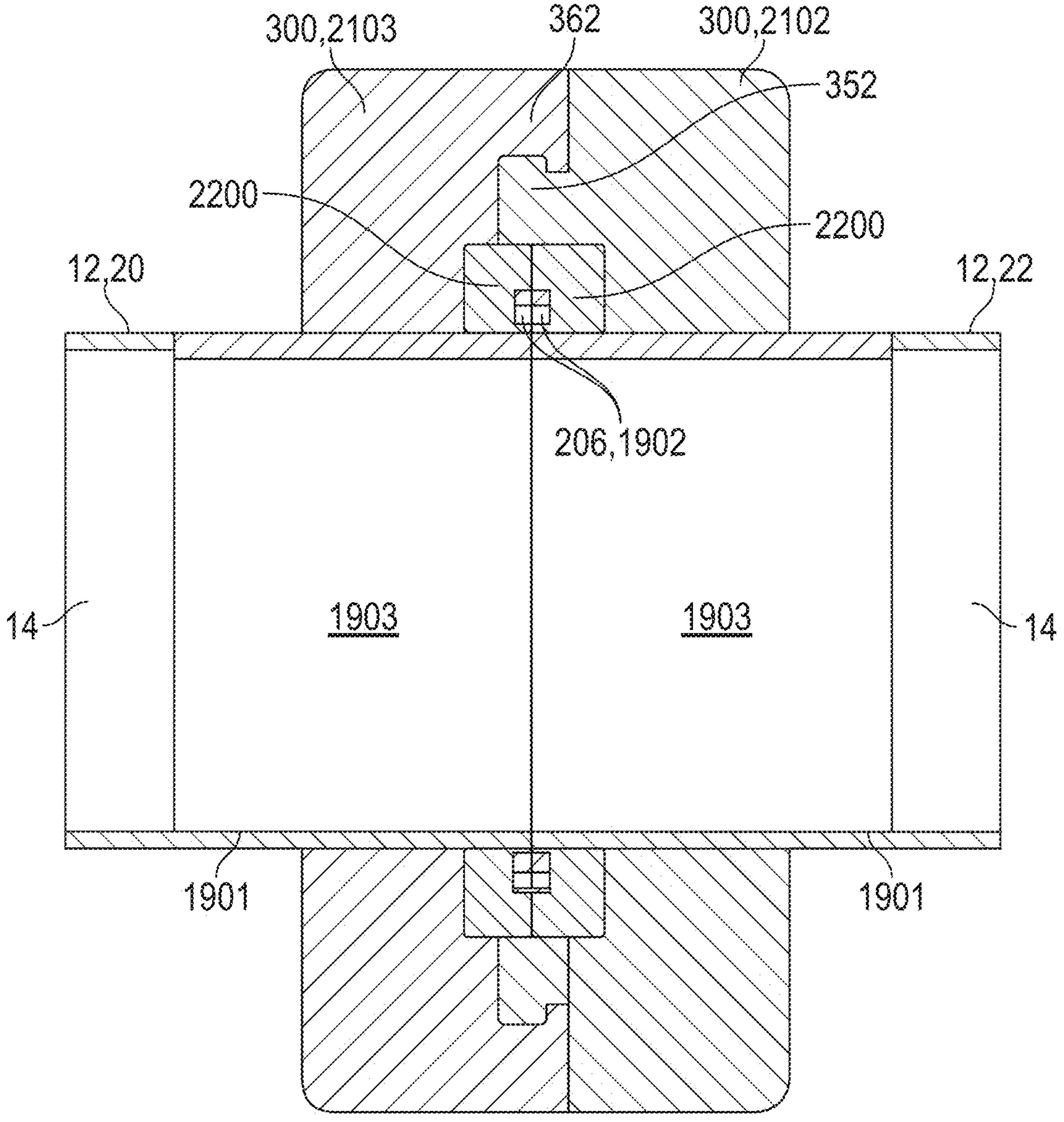

FIGS. 23A-23C illustrate an example of utilizing two separate cartridges 1900 coupled with a corresponding tubular structure 20, 22, and securing the fasteners 1902 by compression between the two gaskets 2200. As illustrated in FIGS. 23A-23C, each of the cartridges 1900 can include at least one row of fasteners 1902. Each of the fasteners 1902 have punctured the corresponding tubular structures 20, 22. The two tubular structures 20, 22, each with cartridges 1900 coupled thereto, are brought together so that the lumens 14 are in fluid communication with one another through the lumens 1903 of the cartridges 1900. Similar to FIGS. 22A-22C, the rings 2102, 2103 are brought together and coupled with one another via mating portions 352, 362. Upon bringing the rings 2102, 2103 together, gaskets 2200 for each of the rings 2102, 2103 compress against each other, receiving the fasteners 1902 for the two cartridges 1900 between the two gaskets 2200. In some examples, the compression of the gaskets 2200 against the fasteners 1902 can sufficiently secure the coupling of the rings 2102, 2103 with the cartridges 1900. In some examples, after compression of the gaskets 2200 against the fasteners 1902, the fasteners 1902, the rings 2102, 2103, and/or the gaskets 2200 may be rotated so that the fasteners 1902 puncture into the gaskets 2200. In some examples, the fasteners 1902 may be received by the gaskets 2200 or the ring 2102, 2103.

Figure 24A:
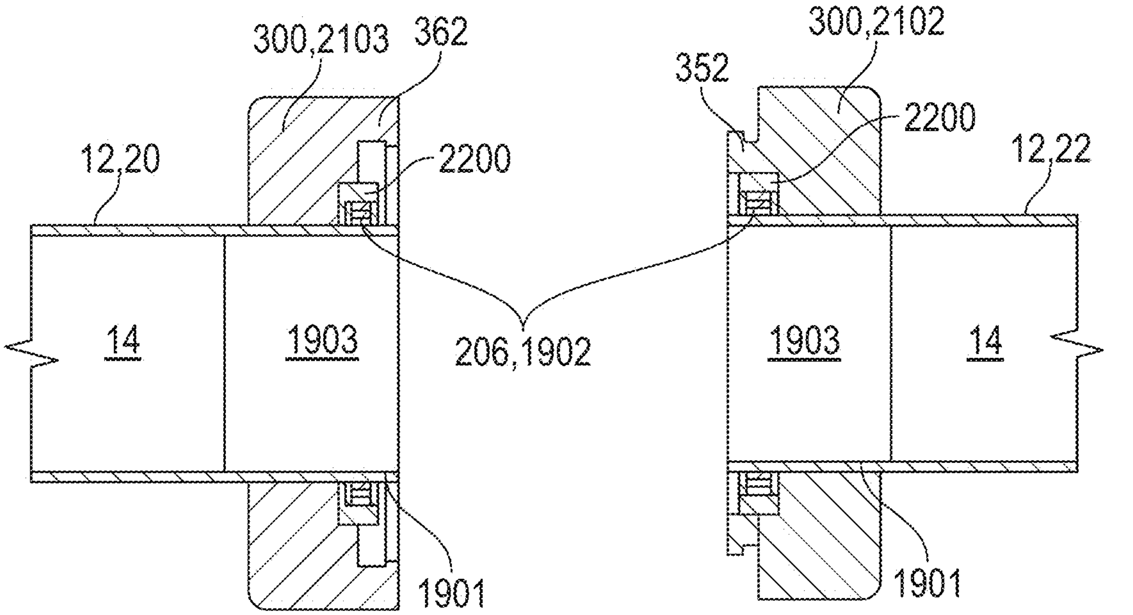
FIGS. 24A, 24B, and 24C illustrate coupling two tubular structures with an exemplary cartridge.
Figure 24B:
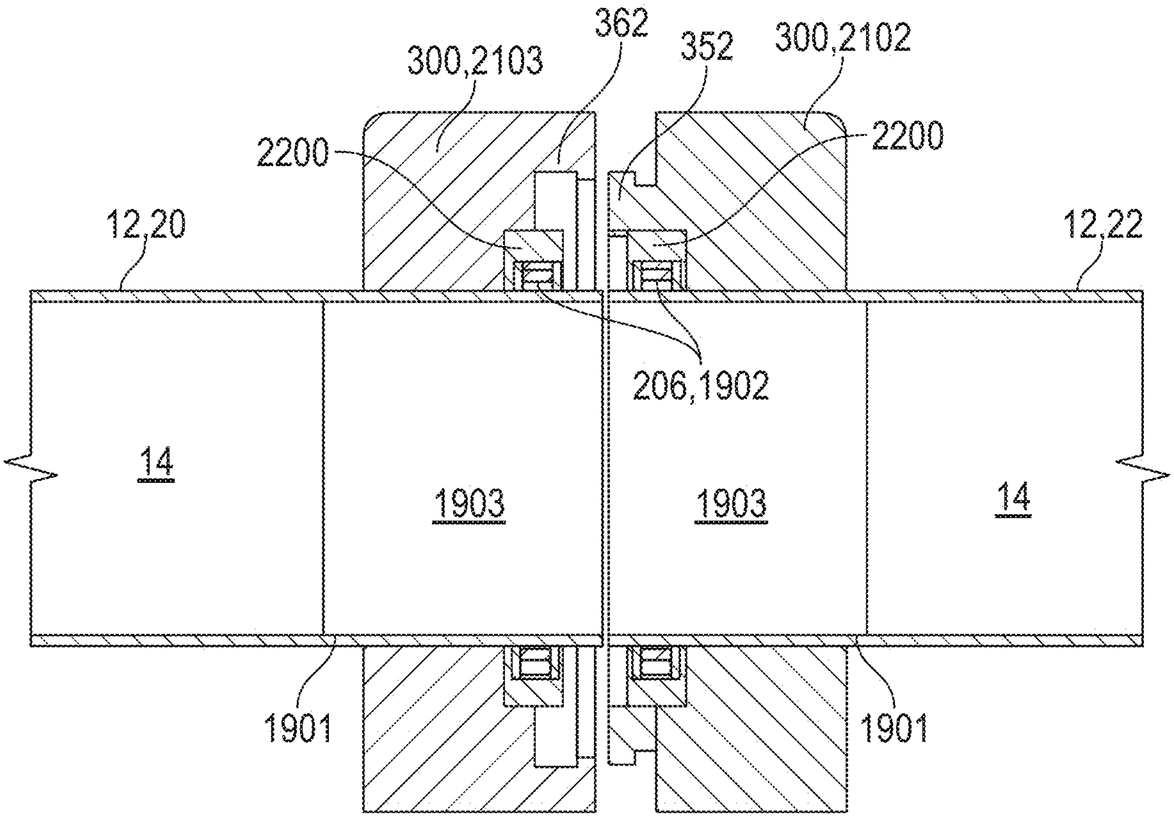
Figure 24C:
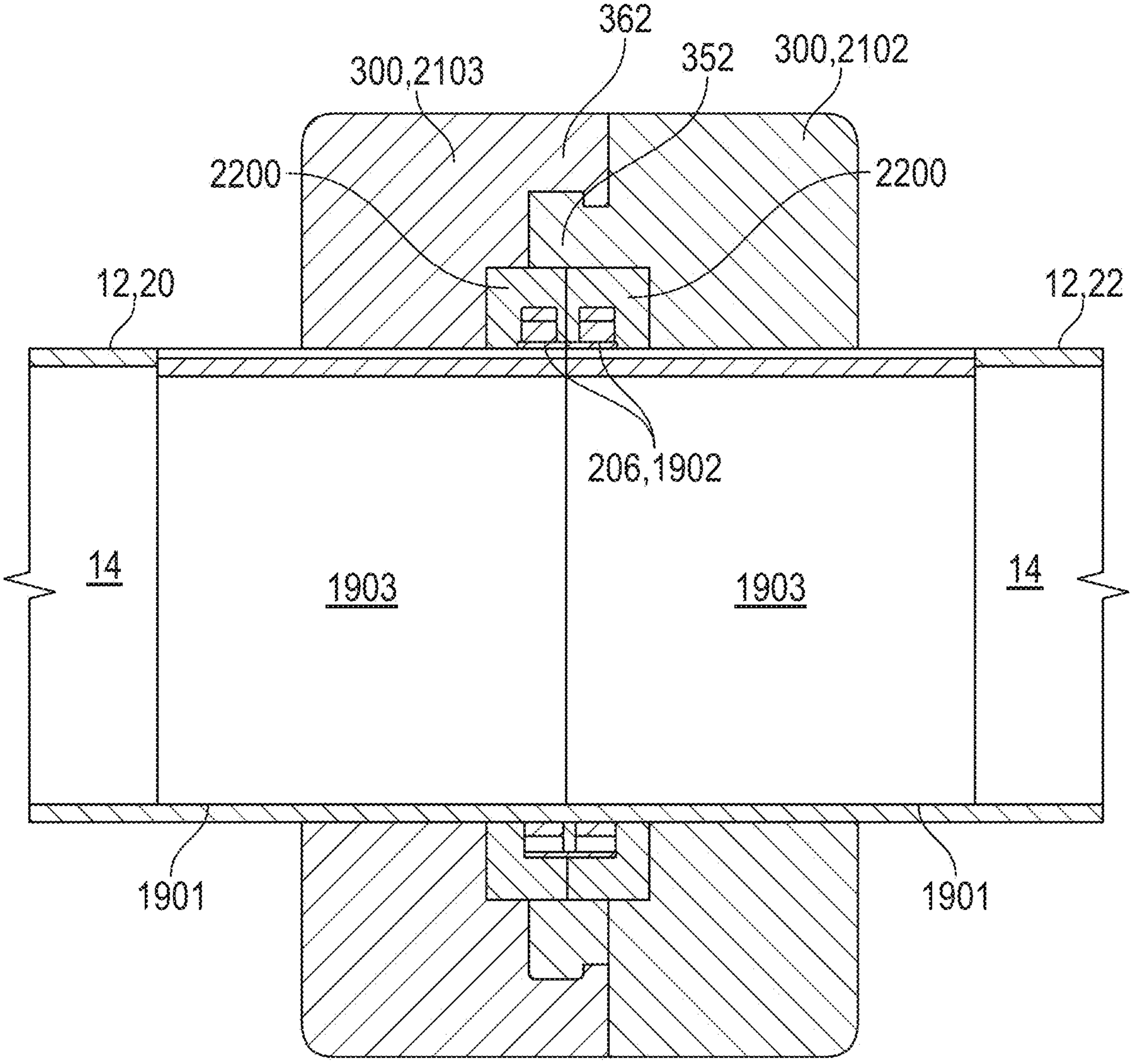

FIGS. 24A-24C illustrate an example of the fasteners 1902 directly puncturing into the gasket 2200 of the corresponding ring 300 while puncturing through the tubular structure 12. The rings 2102, 2103 are then brought together and coupled with one another via mating portions 352, 362. While FIGS. 24A-24C illustrate an example similar to FIGS. 23A-23C where two separate cartridges 1900 are utilized, in some examples, similar to FIGS. 22A-22C, one cartridge 1900 may be utilized. FIGS. 24A-24C illustrate the mechanism of the fasteners 1902 being directly received in and/or puncturing the corresponding gasket 2200. This mechanism can be utilized in addition to and/or in place of compressing the fasteners 1902 with the gaskets 2200.

Figure 25A:
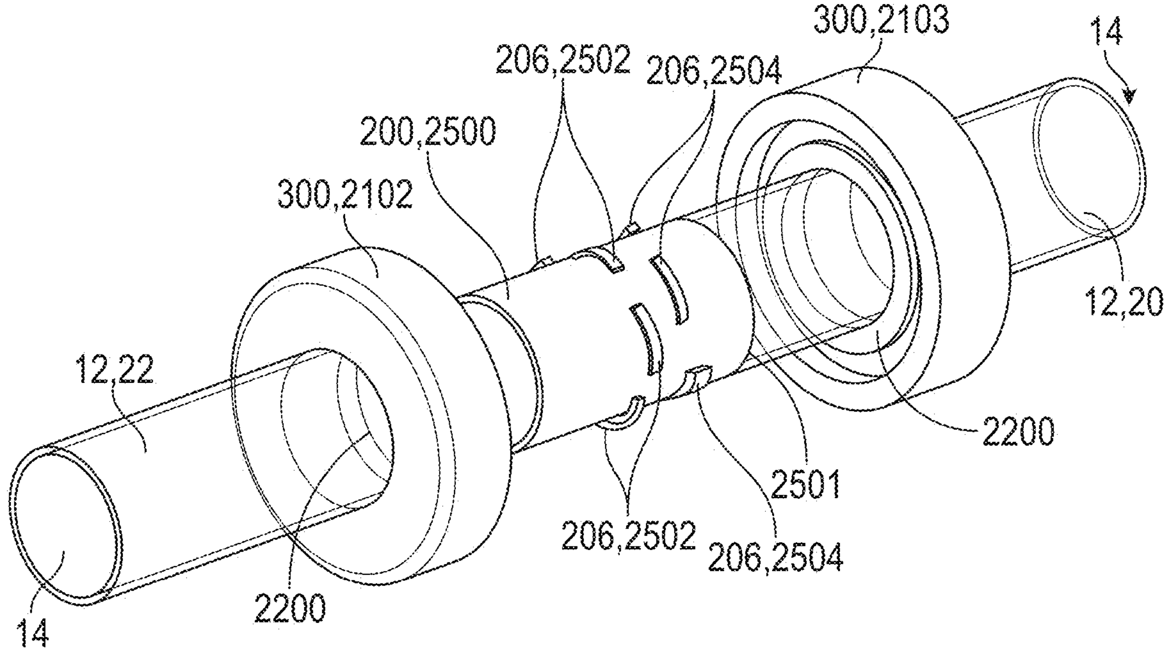
FIGS. 25A, 25B, and 25C illustrate coupling two tubular structures with an exemplary cartridge.
Figure 25B:
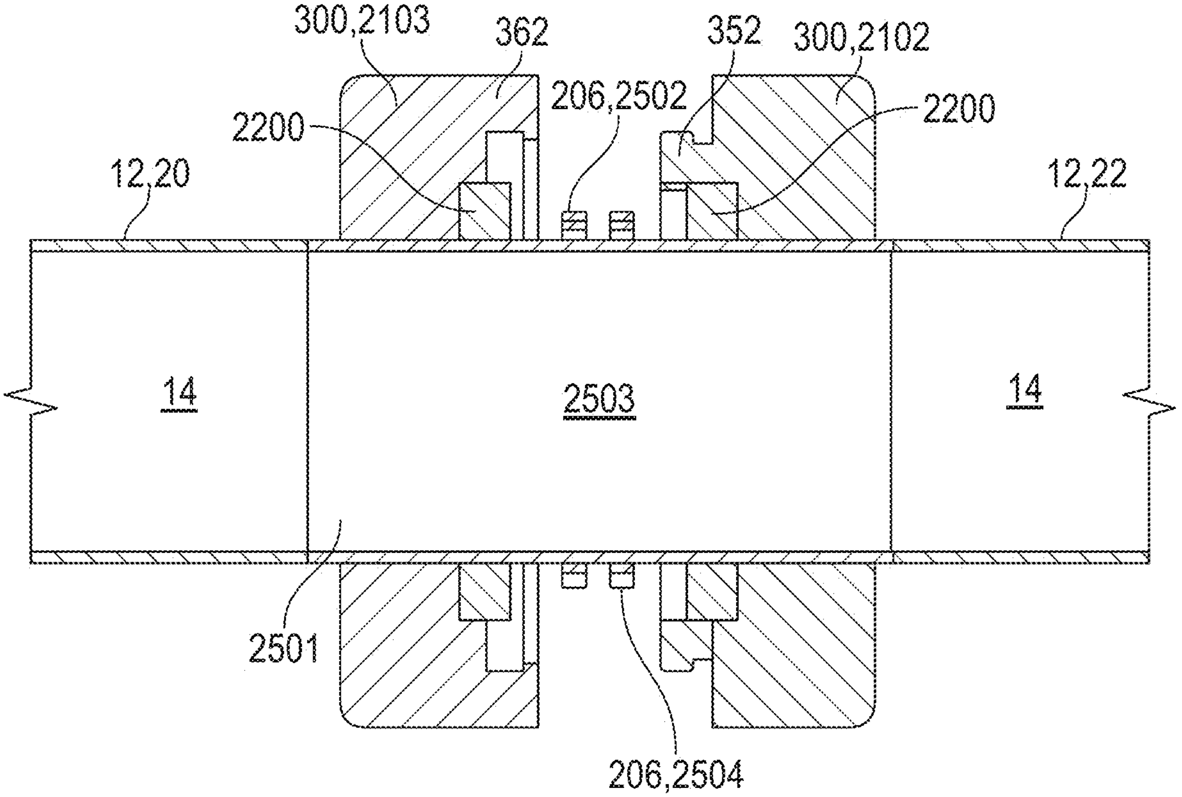
Figure 25C:
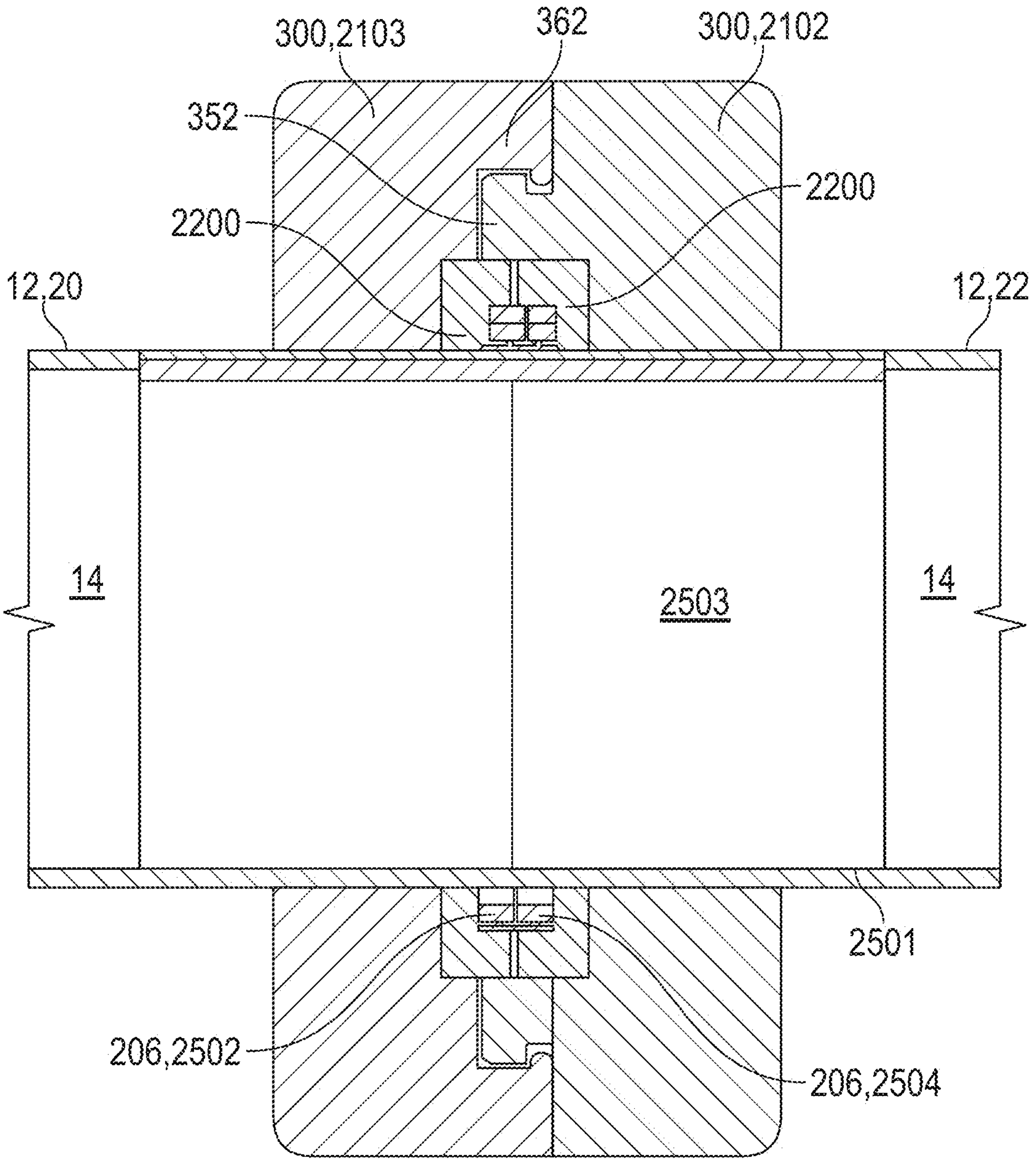

FIGS. 25A-25C illustrate an example of a cartridge 1900 that includes two (or more) rows of fasteners 1902 on one body 1901. Accordingly, instead of overlaying the two tubular structures 20, 22 as in FIGS. 22A-22C, each tubular structure 20, 22 may couple with a corresponding row of fasteners 1902. In some examples, even with multiple rows of fasteners 1902, the tubular structures 20, 22 may still overlap over one or more rows of fasteners 1902. The rings 2102, 2103 are brought together and coupled with one another via mating portions 352, 362. Upon bringing the rings 2102, 2103 together, gaskets 2200 for each of the rings 2102, 2103 compress against each other, receiving the fasteners 1902 for the two cartridges 1900 between the two gaskets 2200. In some examples, the compression of the gaskets 2200 against the fasteners 1902 can sufficiently secure the coupling of the rings 2102, 2103 with the cartridges 1900. In some examples, after compression of the gaskets 2200 against the fasteners 1902, the fasteners 1902, the rings 2102, 2103, and/or the gaskets 2200 may be rotated so that the fasteners 1902 puncture into the gaskets 2200.

FIGS. 26A-27N illustrate examples of an anastomotic coupler 10 which is operable to couple an end of a tubular structure 12 with an end of another tubular structure 12. Elements described in the system of FIGS. 26A-27N that have similar or the same name and/or the same reference numbers as elements in the disclosure for FIGS. 1-25C may have the same features as discussed above. While the discussion below for FIGS. 26A-27N may highlight some differences in features, the disclosure for the system of FIGS. 26A-27N are not limited to those and may also include any and/or all of the features as discussed above.

Figure 26B:
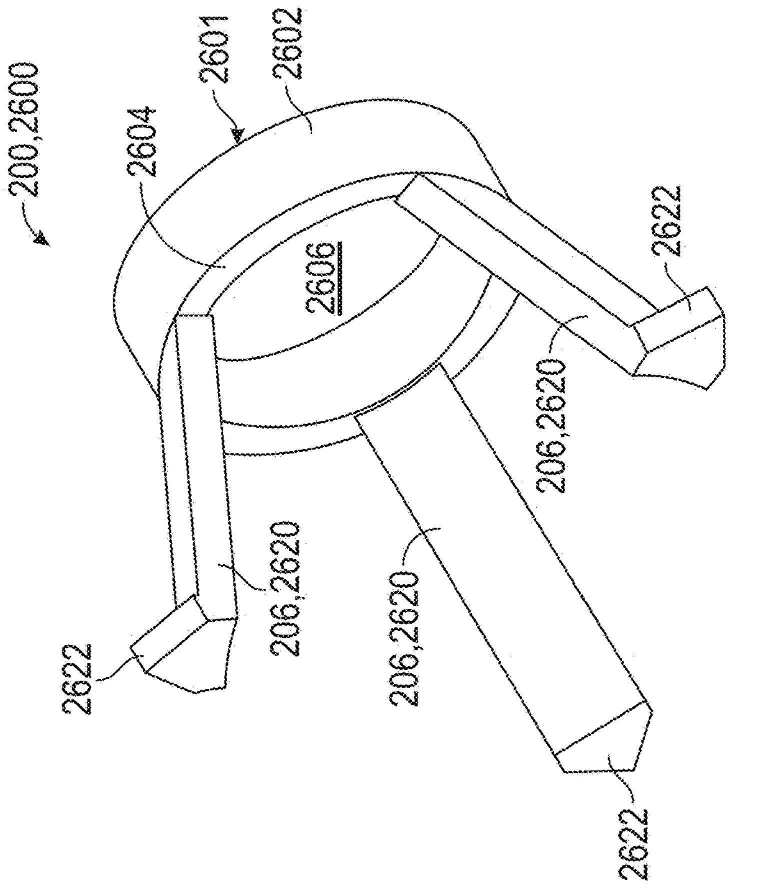
FIGS. 26A and 26B illustrate exemplary cartridges.
Figure 26A:
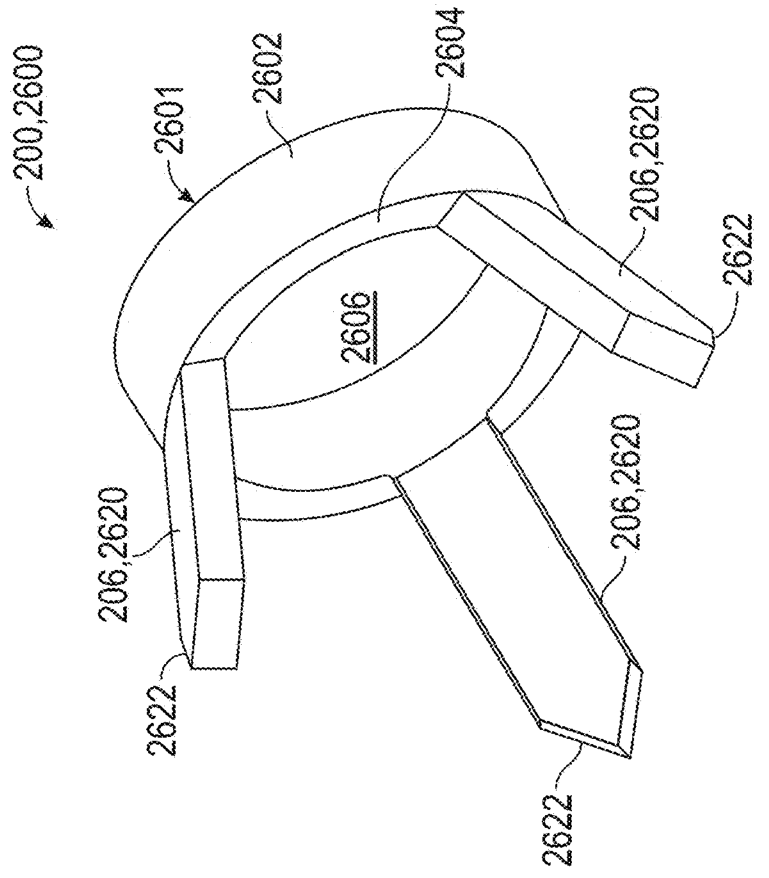

FIGS. 26A and 26B illustrate examples of a cartridge 200, 2600 for an anastomotic coupler 10. As illustrated in FIGS. 26A and 26B, the cartridge 2600 can include a body 2601 which is operable to be received in a tubular structure 12. The body 2601 can have an outer radial surface 2602 and an axial surface 2604. As will be shown below, the outer radial surface 2602 can be operable to abut against and be substantially parallel to a wall 13 of the tubular structure 12. In at least one example, the outer radial surface 2602 can be substantially perpendicular to the radial direction away from the center of the cartridge 2600. In at least one example, the outer radial surface 2602 can extend substantially parallel to the longitudinal axis X-X. The axial surface 2604 can extend at an angle from the outer radial surface 2602. In at least one example, the axial surface 2604 can extend substantially perpendicular to the longitudinal axis X-X. In at least one example, the axial surface 2604 can extend substantially parallel to the radial direction away from the center of the cartridge 2600. In at least one example, when the outer radial surface 2602 is abutting the wall 13 of the tubular structure 12, the axial surface 2604 can extend at an angle in relation to the wall 13 of the tubular structure 12.

The body 2601 of the cartridge 2600 can form a body lumen 2606 to permit fluid to flow across the body 2601. When the cartridge 2600 is positioned within the tubular structure 12, fluid can flow through the lumen 14 of the tubular structure 12 as well as through the body lumen 2606 of the cartridge 2600. Accordingly, the cartridge 2600, when positioned in the tubular structure 12, does not obstruct the flow of the fluid through the tubular structure 12.

One or more fasteners 206, 2620 extend from the axial surface 2604 at an angle from the longitudinal axis X-X. The fasteners 2620 can extend from the axial surface 2604 at any suitable angle in relation to the longitudinal axis X-X. For example, the fasteners 2620 can extend at an angle between 1 degree and 89 degrees in relation to the longitudinal axis X-X, but other angles may be suitable without deviating from the scope of the disclosure. The fasteners 2620 can be operable to puncture the wall 13 of the tubular structure 12. As the fasteners 2620 extend from the axial surface 2604 at an angle from the longitudinal axis X-X, the fasteners 2620 also extend at an angle in relation to the wall 13 of the tubular structure 12 when the cartridge 2600 is positioned in the tubular structure 12. Accordingly, the fasteners 2620 being at an angle in relation to the wall 13 of the tubular structure 12 allow for the fasteners 2620 to puncture through the wall 13 of the tubular structure 12, coupling the cartridge 2600 to the tubular structure 12.

As illustrated in FIG. 26A, an end 2622 of the fasteners 2620 can be substantially linear. As illustrated in FIG. 26B, the end 2622 of the fasteners 2620 can be bent. The ends 2622 of the fasteners 2620 can all be the same or different. For example, the fasteners 2620 can each have an end 2622 that is linear, curved, bent, and/or hooked. The fasteners 2620 can each have an end 2622 that has other shapes and configurations without deviating from the scope of the disclosure so long as the fasteners 2620 can puncture the wall 13 of the tubular structure 12.

While FIGS. 26A-27N illustrate a cartridge 2600 with three fasteners 2620, one, two, four, or more fasteners 2620 can be provided without deviating from the scope of the disclosure. While FIGS. 26A-27N illustrate a cartridge 2600 with fasteners 2620 all having the same lengths, in some examples, the lengths of the fasteners 2620 can vary.

Figure 27A:
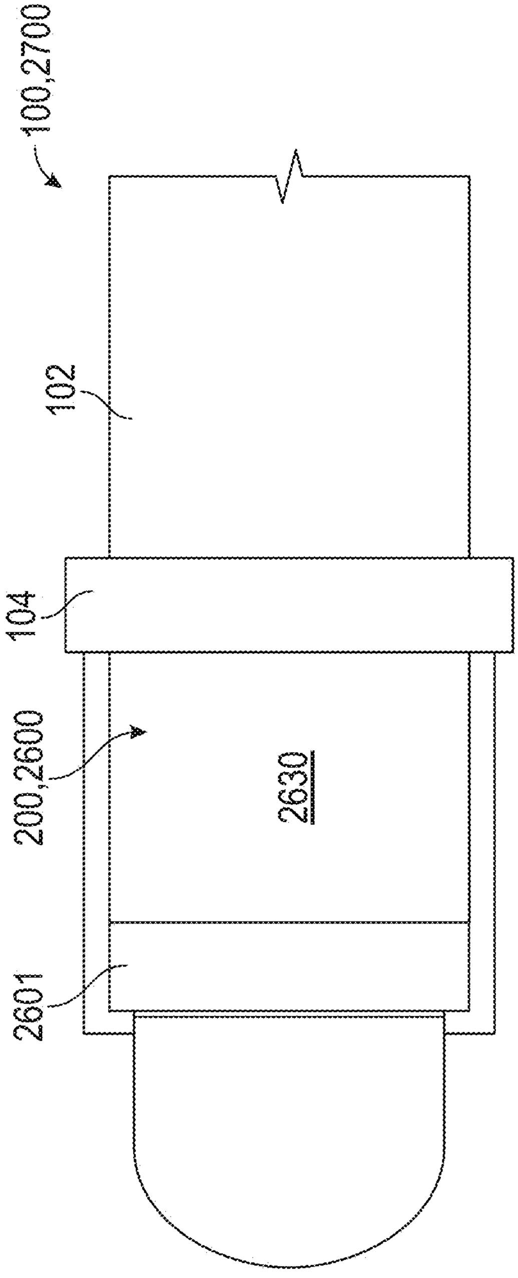
FIGS. 27A-L illustrate deployment of the cartridge.
Figure 27B:
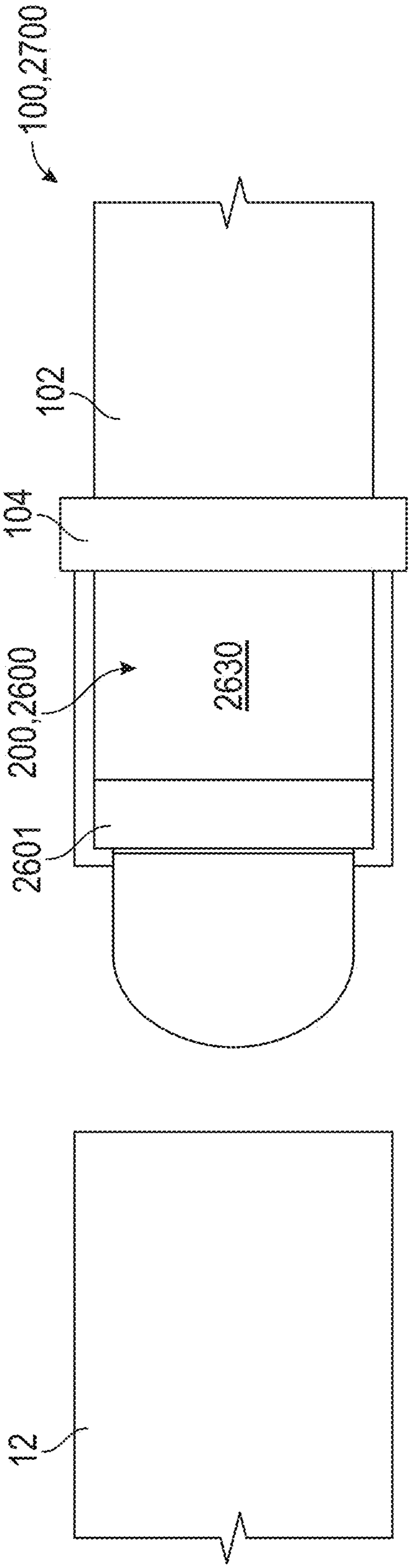
Figure 27C:
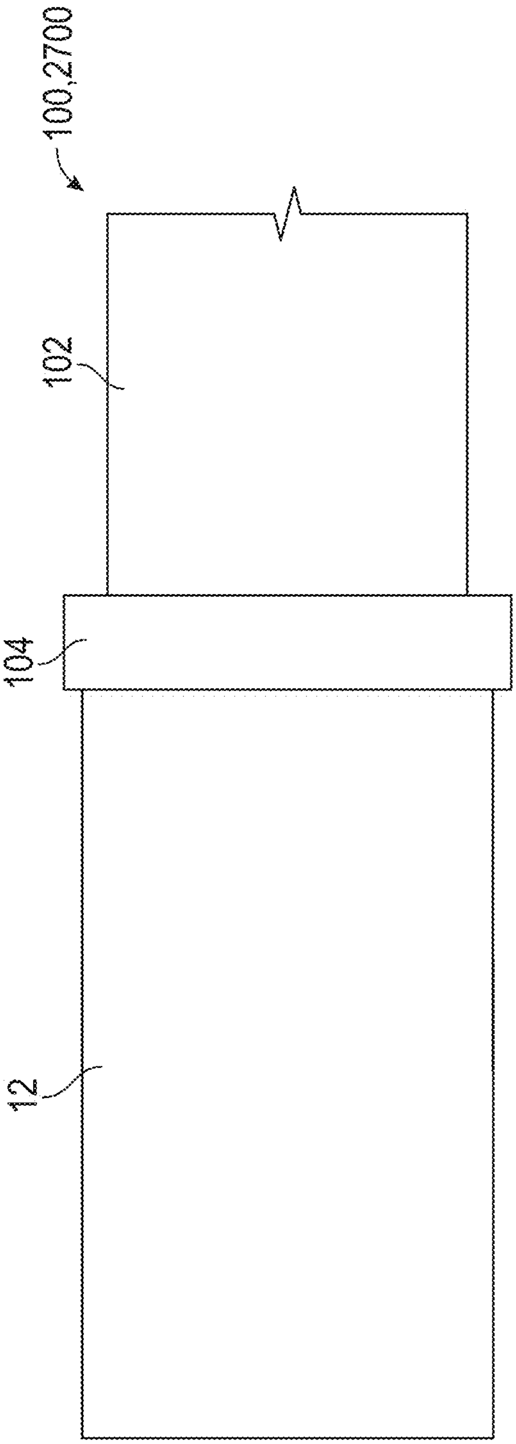
Figure 27D:
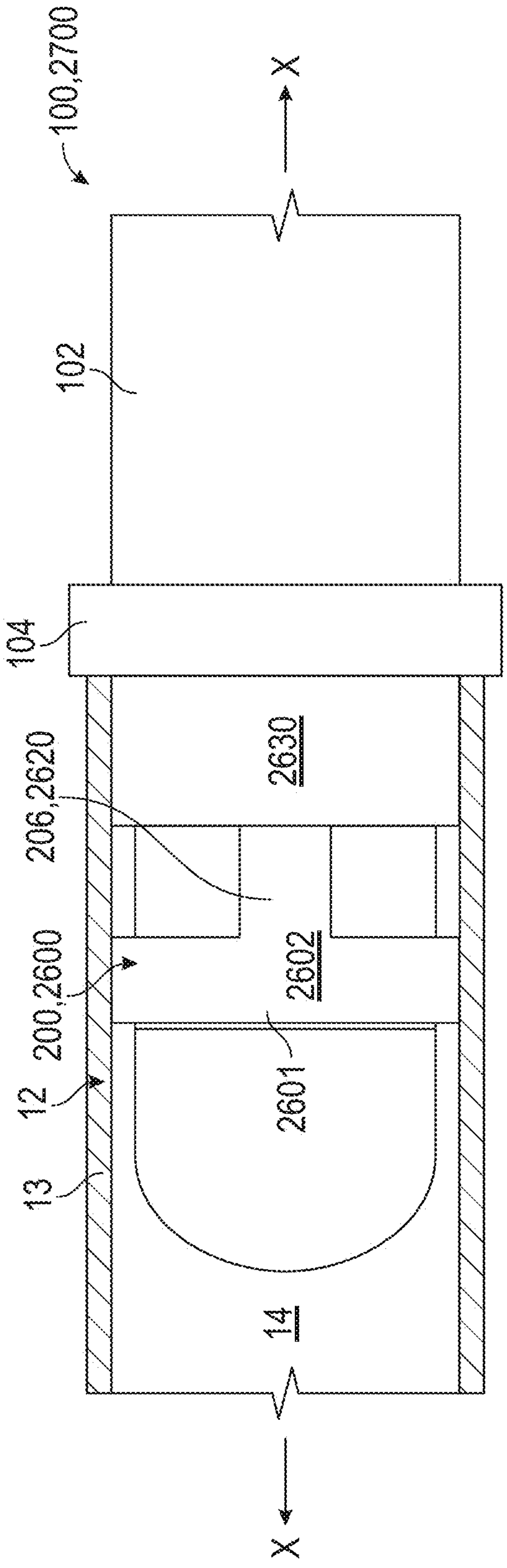
Figure 27E:
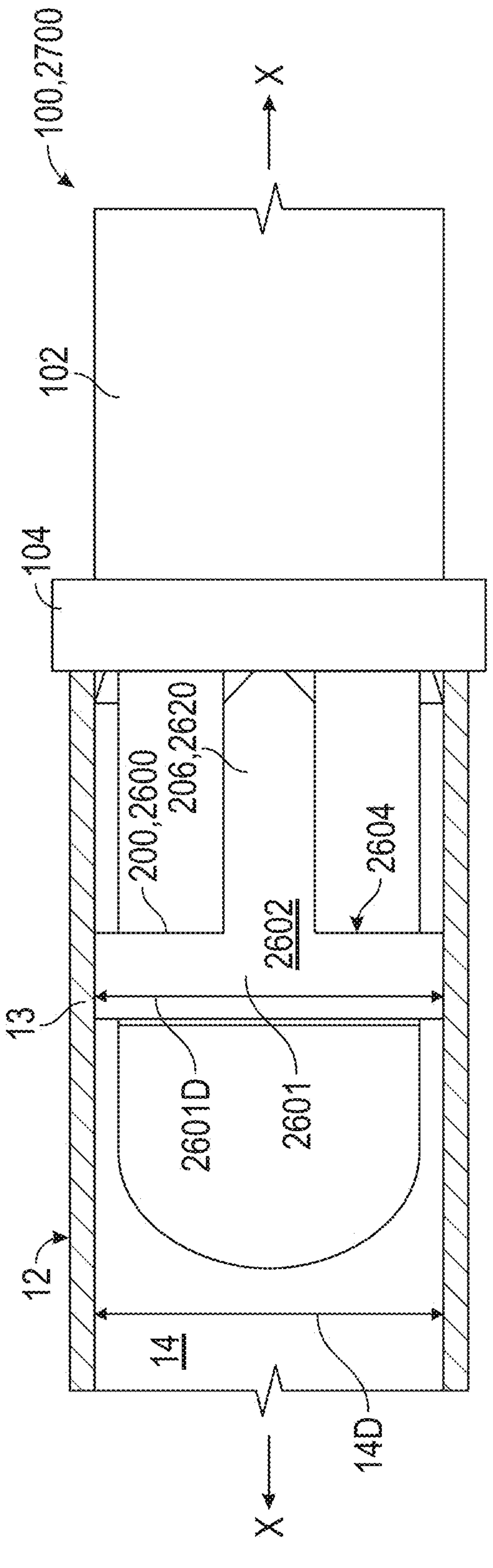
Figure 27F:
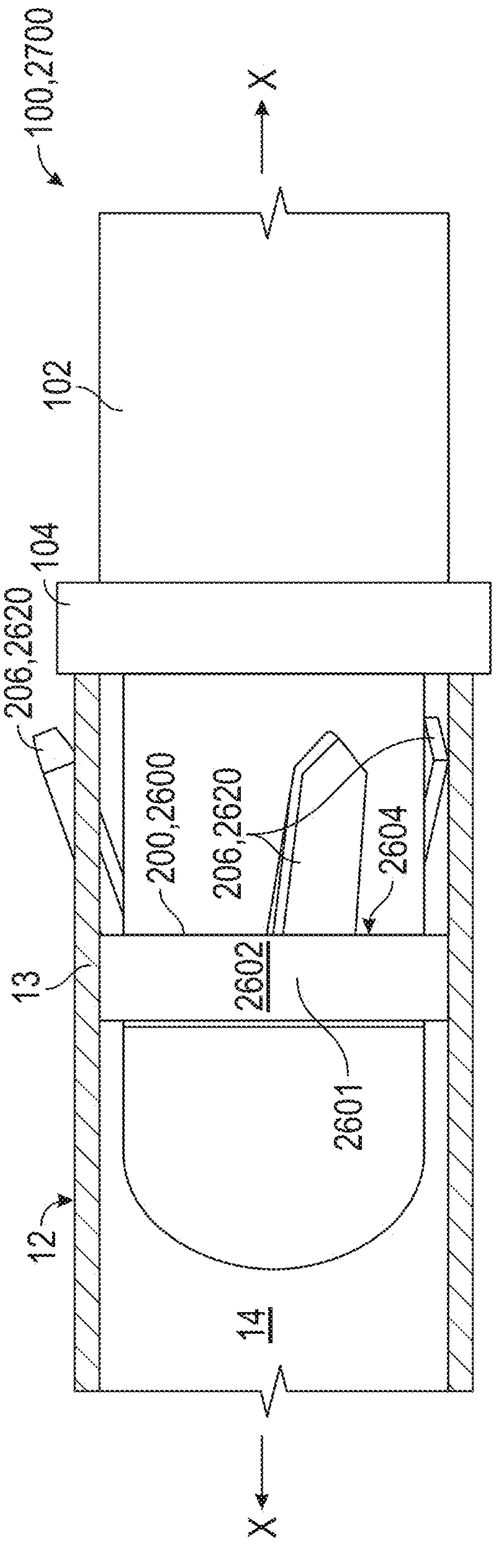
Figure 27G:
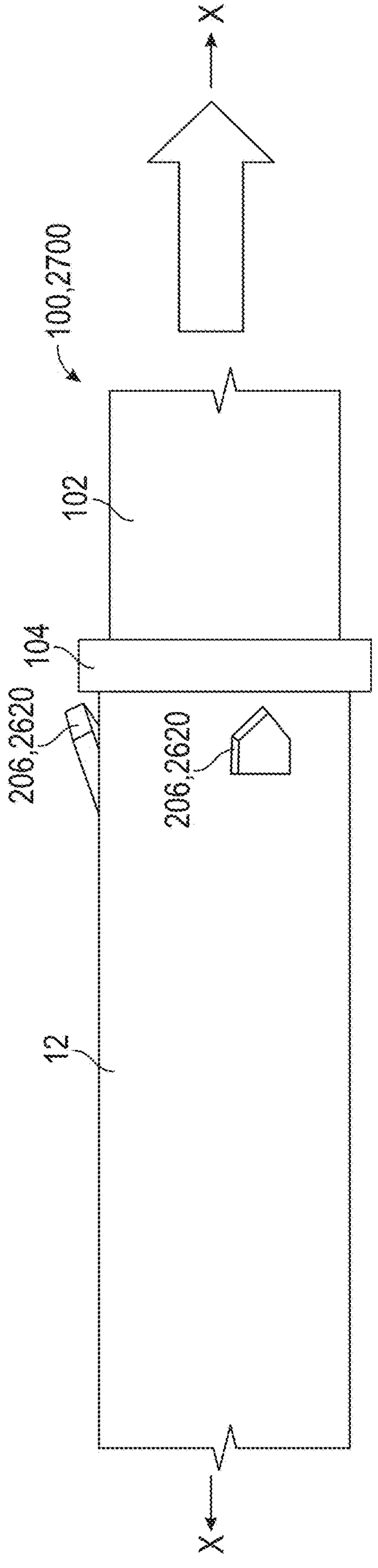
Figure 27H:
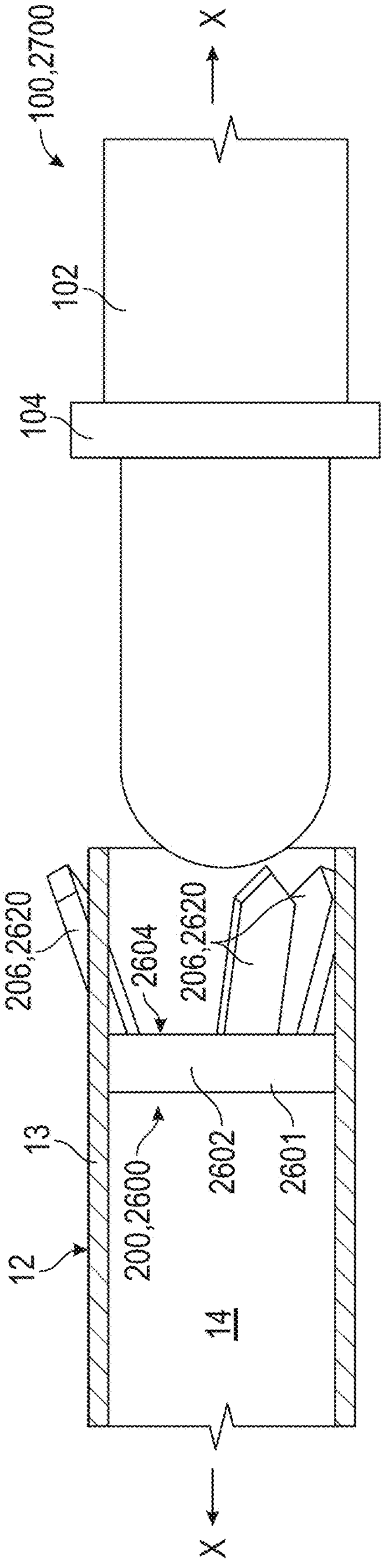
Figure 27I:
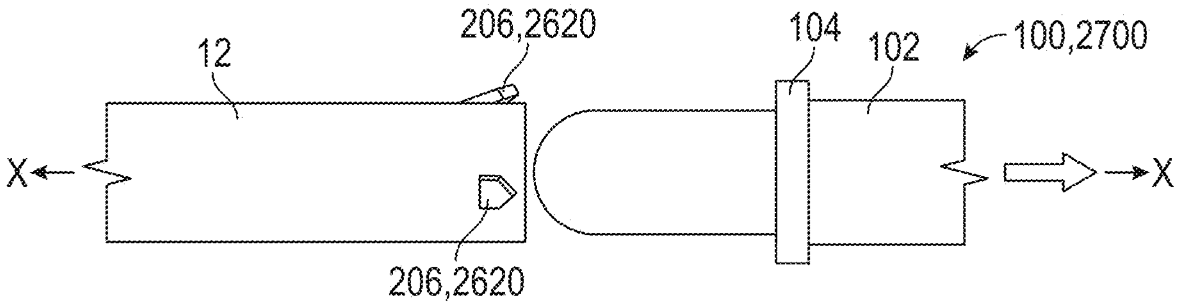
Figure 27J:
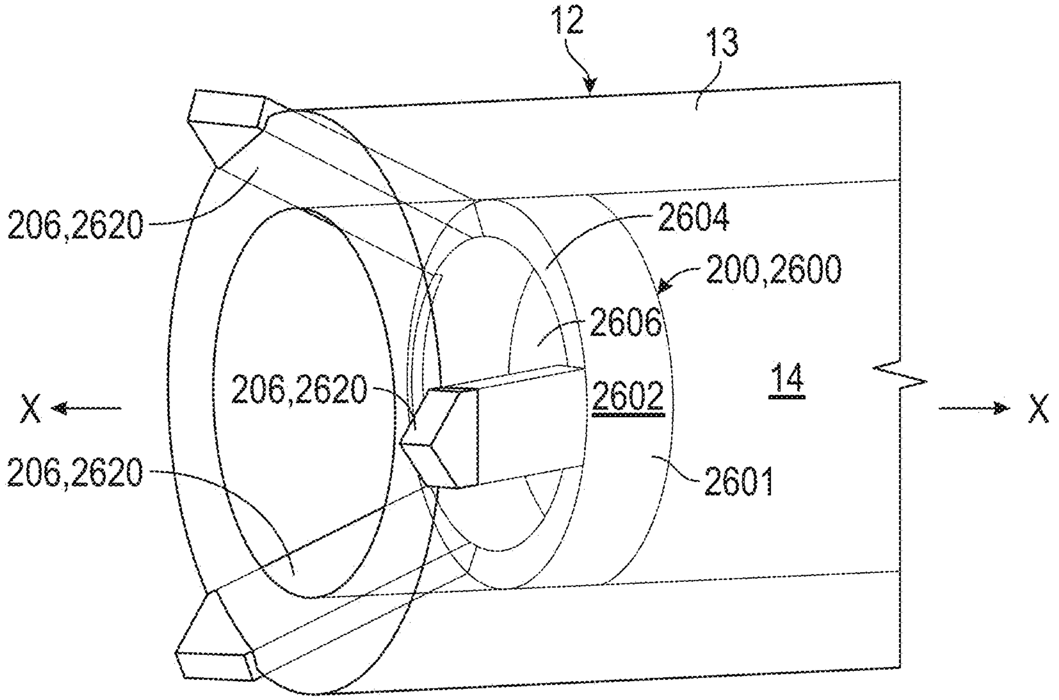
Figure 27K:
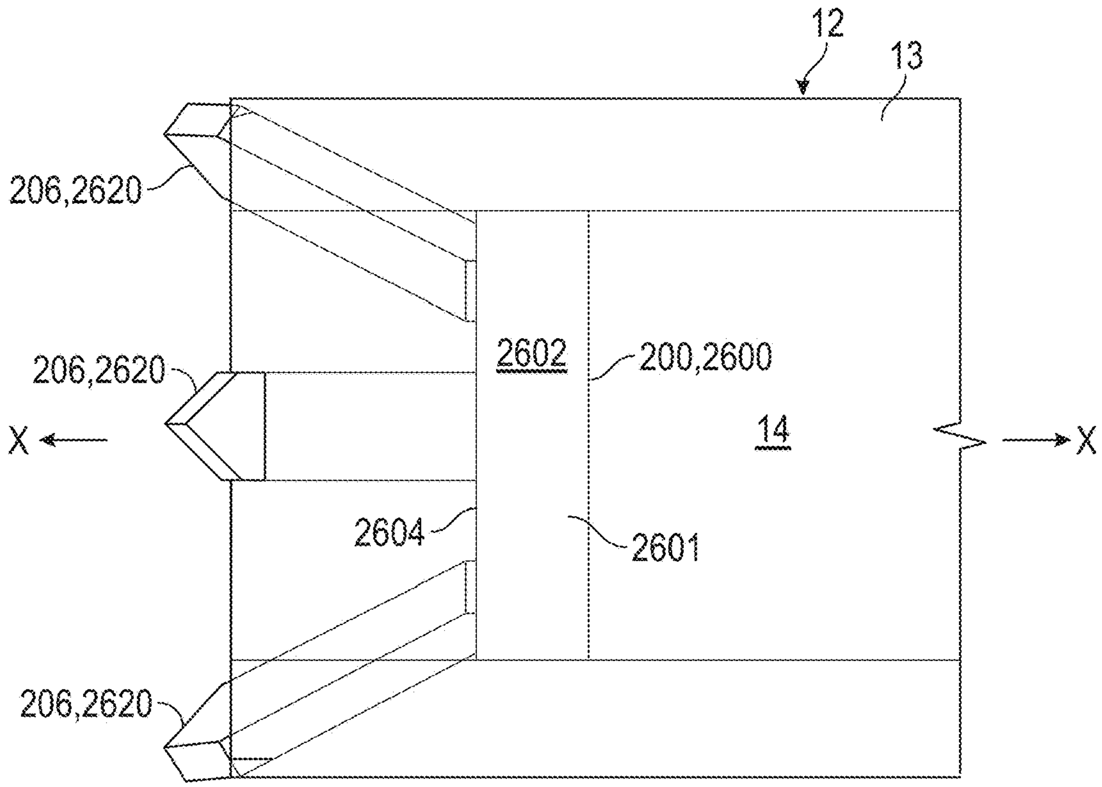
Figure 27L:
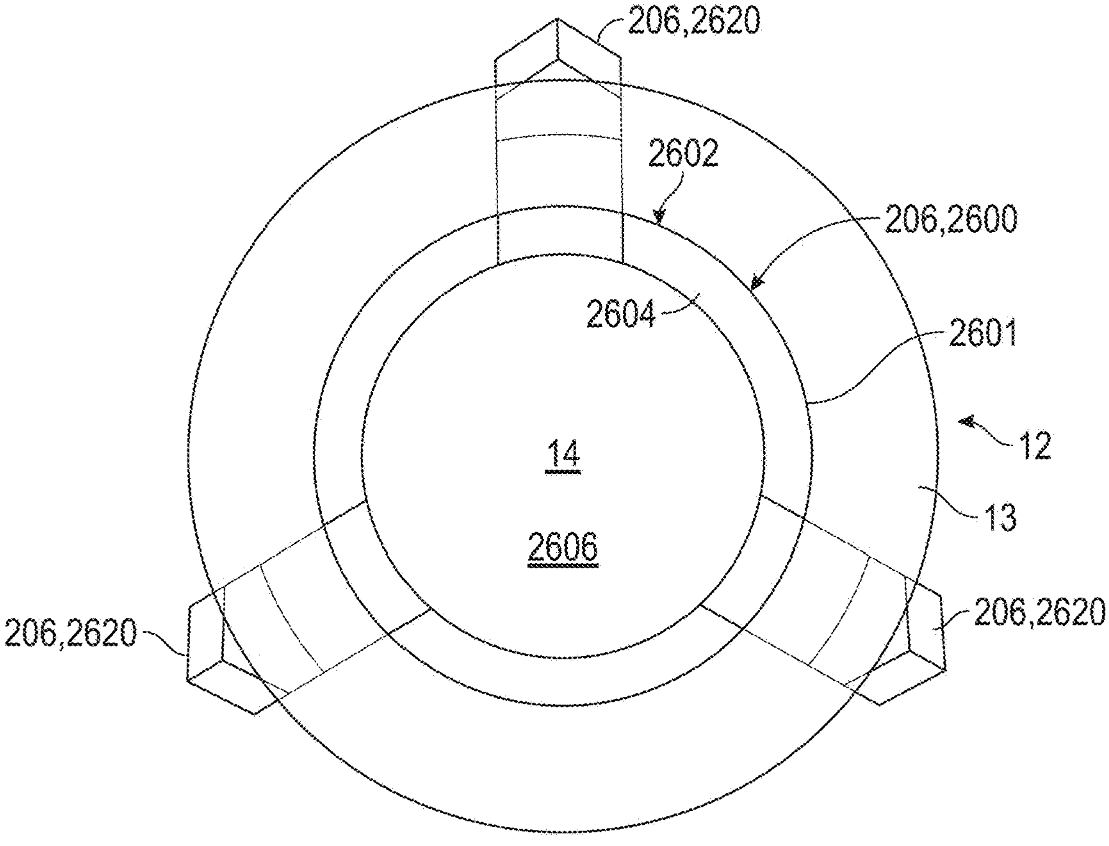
Figure 27M:
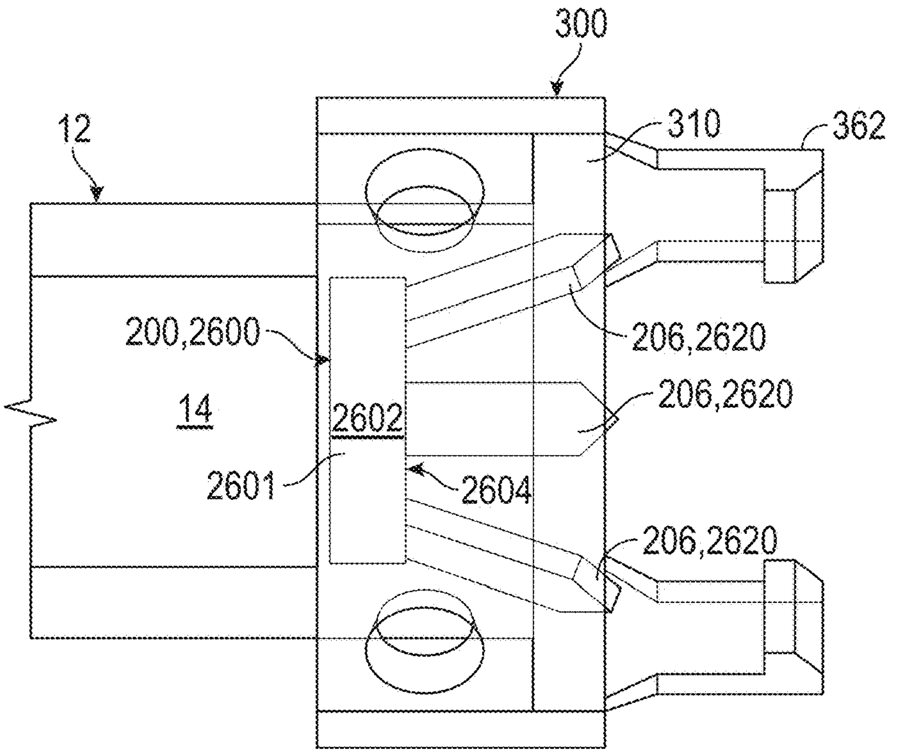
FIG. 27M illustrates coupling of the cartridge with a ring.
Figure 27N:
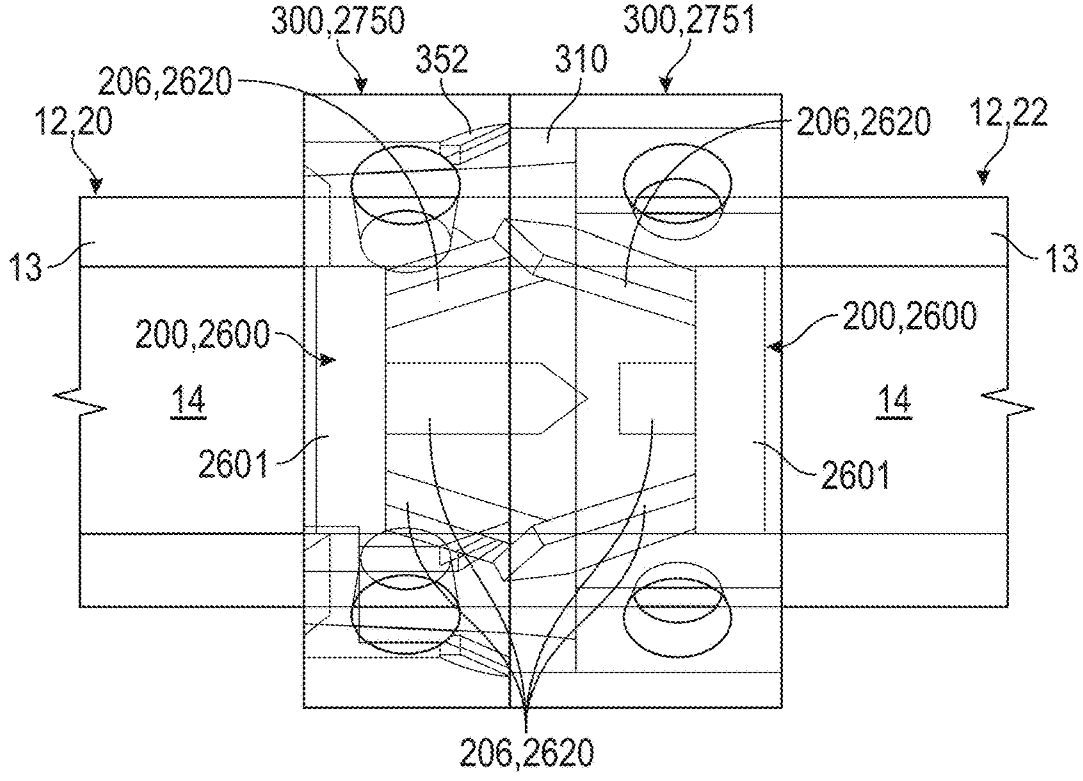
FIG. 27N illustrates coupling two tubular structures with the cartridges and rings.

FIGS. 27A-27N illustrate the application of the anastomotic coupler 10 with the cartridge 200, 2600, for example as illustrated in FIGS. 26A-26B.

FIG. 27A illustrates an example of a fixation device 100, 2700 that is operable to position the cartridge 2600 in the tubular structure 12. In at least one example, the fixation device 2700 can include a body 102 and a stop 104, for example as discussed above. The cartridge 2600 can receive and/or be coupled with the body 102. As illustrated in FIG. 27A, a sheath 2630 can be provided and operable to receive the one or more fasteners 26 such that the fasteners 2620 are covered until the cartridge 2600 is positioned inside the tubular structure 12. In some examples, when the fasteners 2620 are received in the sheath 2630, the fasteners 2620 can extend from the axial surface 2604 substantially parallel to the longitudinal axis X-X. As such, the fasteners 2620 do not prematurely puncture the wall 13 of the tubular structure 12 before the cartridge 2600 is positioned as desired in the tubular structure 12. In some examples, the anastomotic coupler 10 does not include a sheath 2630, and the fasteners 2620 do not puncture the wall 13 of the tubular structure 12 until actuated. For example, the fasteners 2620 can be actuated to puncture the wall 13 of the tubular structure 12 by an inflatable balloon that pushes the fasteners 2620 radially outward, by the user pushing the wall 13 of the tubular structure 12 against the fasteners 2620, by a pusher rod or ball such as a tapered pusher rod 150, by traction, and/or by other suitable mechanisms to radially push the fasteners 2620 against the wall 13 of the tubular structure 12.

As illustrated in FIG. 27B, the fixation device 2700 is moved toward the tubular structure 12 to insert the cartridge 2600 into the lumen 14 of the tubular structure 12. As illustrated in FIGS. 27C and 27D, the cartridge 2600 is positioned inside the tubular structure 12. In at least one example, the stop 104 can control how far the fixation device 2700 is received in the tubular structure 12 so that the cartridge 2600 is positioned in the desired location in the tubular structure 12. As illustrated in FIG. 27D, when the cartridge 2600 is adequately positioned in the tubular structure 12, the fixation device 2700 can be actuated to remove the sheath 2630 to expose the fasteners 2620.

As illustrated in FIG. 27E, the sheath 2630 is fully removed to expose the fasteners 2620. In at least one example, as illustrated in FIG. 27E the body 2601 of the cartridge 2600 can have a diameter 2601D substantially the same as a diameter 14D of the lumen 14 of the tubular structure 12 so that the outer radial surface 2602 abuts against the wall 13 of the tubular structure 12 to maintain the shape of the tubular structure 12. Accordingly, fluid can still sufficiently flow through the tubular structure 12 and the cartridge 2600.

As illustrated in FIG. 27F, when the sheath 2630 is removed 2620 to uncover the fasteners 2620, the fasteners 2620 can be operable to expand radially outward to be at an angle from the longitudinal axis X-X. As such, as illustrated in FIGS. 27F-27L, the fasteners 2620 can puncture the wall 13 of the tubular structure 12.

After the fixation device 2700 is actuated to remove the sheath 2630 and/or actuate the fasteners 2620 to puncture the wall 13 of the tubular structure 12, the fixation device 2700 can be removed and withdrawn from the tubular structure 12, as illustrated in FIGS. 27G, 27H, and 27I.

As illustrated in FIGS. 27J, 27K, and 27L, the fasteners 2620 have punctured the wall 13 of the tubular structure 12, and the fixation device 2700 has been removed. Accordingly, the fasteners 2620 extend through the wall 13 of the tubular structure 12 at an angle from the longitudinal axis X-X.

FIG. 27M illustrates coupling the cartridge 2600 and the tubular structure 12 to a ring 300. The ring 300 can be operable to receive the tubular structure 12. The ring 300 can include a receiving portion 310 operable to receive at least a portion of the fasteners 206, 2620 of the cartridge 200, 2600. In at least one example, as the fasteners 2620 have punctured the wall 13 of the tubular structure 12 at an angle relative to the longitudinal axis X-X, the fasteners 2620 can also puncture and be received in the receiving portion 310 of the ring 300. Accordingly, the tubular structure 12 is coupled with the ring 300 via the fasteners 2620 of the cartridge 2600. In some examples, the fasteners 2620 can be coupled with the ring 300 via compression within the receiving component 310 of the ring 300 and/or between receiving components 310 of two rings 300. Accordingly, the receiving component 310 of the ring 300 receives at least a portion of the fasteners 2620 to couple the ring 300 with the tubular structure 12.

In at least one example, as illustrated in FIG. 27M, the ring 300 can include a mating portion 362 operable to couple with the mating portion 352 of a corresponding ring 300 for another tubular structure 12. For example, as illustrated in 27N, a first tubular structure 20 can be coupled with a first ring 2750 via a cartridge 2600, and a second tubular structure 22 can be coupled with a second ring 2751 via a cartridge 2600.

In at least one example, the fasteners 2620 of the first cartridge 2600 corresponding with the first tubular structure 20 can extend through the receiving portion 310 of the first ring 2750 and be received in the receiving portion 310 of the second ring 2751 such that the first ring 2750 and the second ring 2751 are coupled to one another. In some examples, the fasteners 2620 of the second cartridge 2600 corresponding with the second tubular structure 22 can extend through the receiving portion 310 of the second ring 2751 and be received in the receiving portion 310 of the first ring 2750 such that the first ring 2750 and the second ring 2751 are coupled to one another.

In at least one example, the first ring 2750 includes a mating portion 362, and the second ring 2751 includes a corresponding mating portion 352. The mating portion 352 is operable to couple with the mating portion 362 to couple the first ring 2750 and the second ring 2751 with one another. In some examples, the rings 300 can be coupled with one another by, for example, fastening, snapping, clamping, stenting, tacking, pinning, loop and hook, adhesive, and/or other connecting method so long as the rings 300 are securely coupled with one another.

As illustrated in FIG. 27N, when the rings 2750, 2751 are coupled with one another, the lumens 14 of the two tubular structures 20, 22 are aligned in fluid communication with one another. In at least one example, the rings 2750, 2751 can create a seal to prevent fluid leakage. Accordingly, the anastomotic coupler 10 provides a more reliable, faster, more secure anastomotic coupling device to create a sealed, leak-proof, open connection between the ends of the tubular structures 20, 22 and allow for "stented" unobstructed flow of luminal contents through the connection/anastomosis (e.g. blood, lymph, fluid, stool contents, gastric contents, etc.). This connection can be strong enough to withstand tension, traction, and high flow pressure, which may occur with distal obstruction.

In some examples, a cap 1400 (for example as shown in FIG. 14) can be provided over the two rings 2750, 2751. The cap 1400 can assist in ensuring the connection between the rings 2750, 2751, as well as protecting the rings 2750, 2751 from external damage. In some examples, the cap 1400 can be deformed to snap over the two rings 2750, 2751.

Figure 28:
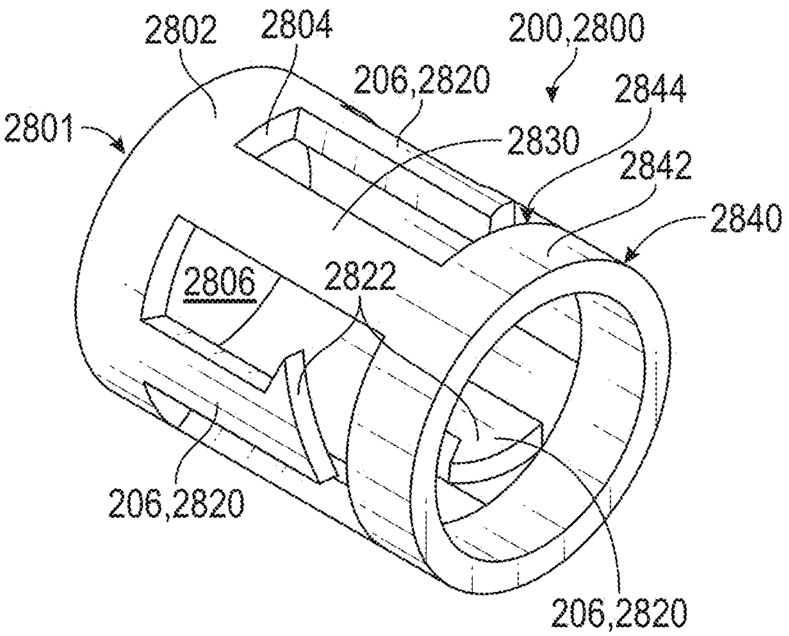
FIG. 28 illustrates an exemplary cartridge.

FIG. 28 illustrates a cartridge 200, 2800 for an anastomotic coupler 10. As illustrated in FIG. 28, the cartridge 2800 can include a body 2801 which is operable to be received in a tubular structure 12. The body 2801 can have an outer radial surface 2802 and an axial surface 2804. As will be shown below, the outer radial surface 2802 can be operable to abut against and be substantially parallel to a wall 13 of the tubular structure 12. In at least one example, the outer radial surface 2802 can be substantially perpendicular to the radial direction away from the center of the cartridge 2800. In at least one example, the outer radial surface 2802 can extend substantially parallel to the longitudinal axis X-X. The axial surface 2804 can extend at an angle from the outer radial surface 2802. In at least one example, the axial surface 2804 can extend substantially perpendicular to the longitudinal axis X-X. In at least one example, the axial surface 2804 can extend substantially parallel to the radial direction away from the center of the cartridge 2800. In at least one example, when the outer radial surface 2802 is abutting the wall 13 of the tubular structure 12, the axial surface 2804 can extend at an angle in relation to the wall 13 of the tubular structure 12.

The body 2801 of the cartridge 2800 can form a body lumen 2806 to permit fluid to flow across the body 2801. When the cartridge 2800 is positioned within the tubular structure 12, fluid can flow through the lumen 14 of the tubular structure 12 as well as through the body lumen 2806 of the cartridge 2800. Accordingly, the cartridge 2800, when positioned in the tubular structure 12, does not obstruct the flow of the fluid through the tubular structure 12.

The cartridge 2800 can also include a support 2840 and one or more columns 2830 that extend between the body 2801 (for example the axial surface 2804) and the support 2840. As illustrated in FIG. 28, the cartridge 2800 can include three columns 2830. In some examples, the cartridge 2800 can include one, two, or more than three columns without deviating from the scope of the disclosure.

In at least one example, the support 2840 has substantially the same shape and/or size as the body 2801. The support 2840 can have a support outer radial surface 2842 and a support axial surface 2844. In at least one example, the support axial surface 2844 can substantially face the axial surface 2804. The support outer radial surface 2842 can be operable to abut against and be substantially parallel to a wall 13 of the tubular structure 12. In at least one example, the support outer radial surface 2842 can be substantially perpendicular to the radial direction away from the center of the cartridge 2800. In at least one example, the support outer radial surface 2842 can extend substantially parallel to the longitudinal axis X-X. The support axial surface 2844 can extend at an angle from the support outer radial surface 2842. In at least one example, the support axial surface 2844 can extend substantially perpendicular to the longitudinal axis X-X. In at least one example, the support axial surface 2844 can extend substantially parallel to the radial direction away from the center of the cartridge 2800. In at least one example, when the support outer radial surface 2842 is abutting the wall 13 of the tubular structure 12, the support axial surface 2844 can extend at an angle in relation to the wall 13 of the tubular structure 12.

The support 2840 of the cartridge 2800 can form a support lumen 2846 to permit fluid to flow across the support 2840. The support lumen 2846 can be in fluid communication with the body lumen 2806 such that fluid can flow across the entire cartridge 2800. When the cartridge 2800 is positioned within the tubular structure 12, fluid can flow through the lumen 14 of the tubular structure 12 as well as through the body lumen 2806 and the support lumen 2846 of the cartridge 2800. Accordingly, the cartridge 2800, when positioned in the tubular structure 12, does not obstruct the flow of the fluid through the tubular structure 12. The support 2840 can provide additional support to the tubular structure 12 in addition to the body 2801.

One or more fasteners 206, 2820 extend from the axial surface 2804. The fasteners 2820 can be operable to puncture the wall 13 of the tubular structure 12, coupling the cartridge 2600 to the tubular structure 12. As illustrated in FIGS. 28A and 28B, in at least one example, the fasteners 206, 2820 can extend substantially perpendicularly from the axial surface 2804. In at least one example, the fasteners 206, 2820 can be shipped, stored, and/or implemented with the fasteners 206, 2820 substantially perpendicular to the axial surface 2804 (for example, substantially parallel to the longitudinal axis X-X). When the fasteners 206, 2820 are received in the tubular structure 12, the fasteners 206, 2820 can be transitioned to extend from the axial surface 2804 at an angle to puncture the walls 13 of the tubular structure 12.

As illustrated in FIG. 28, an end 2822 of the fasteners 2820 can be barbed to include a barb. In some examples, the end 2822 of the fasteners 2820 can be barbed to include two barbs extending in opposite directions. In some examples, the end 2622 of each of the fasteners 2820 can be substantially linear. In some examples, the end 2822 of the fasteners 2820 can be bent. The ends 2822 of the fasteners 2820 can all be the same or different. For example, the fasteners 2820 can each have an end 2822 that is barbed, linear, curved, bent, and/or hooked. The fasteners 2820 can each have an end 2822 that has other shapes and configurations without deviating from the scope of the disclosure so long as the fasteners 2820 can puncture the wall 13 of the tubular structure 12 and maintain coupling with the wall 13.

While FIG. 28 illustrates a cartridge 2800 with three fasteners 2820, one, two, four, or more fasteners 2820 can be provided without deviating from the scope of the disclosure. While FIG. 28 illustrates a cartridge 2800 with fasteners 2820 all having the same lengths, in some examples, the lengths of the fasteners 2820 can vary.

As illustrated in FIG. 28, the cartridge 2800 can include three columns 2830. In some examples, the cartridge 2800 can include one, two, or more than three columns without deviating from the scope of the disclosure.

Figure 29A:
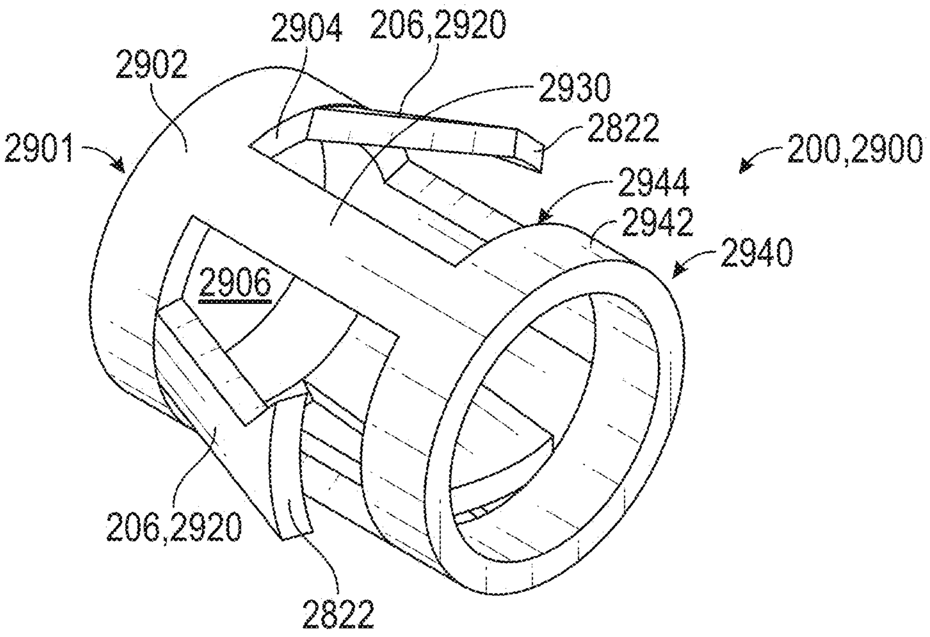
FIGS. 29A, 29B, and 29C illustrate the cartridge with the arms extended at an angle.
Figure 29B:
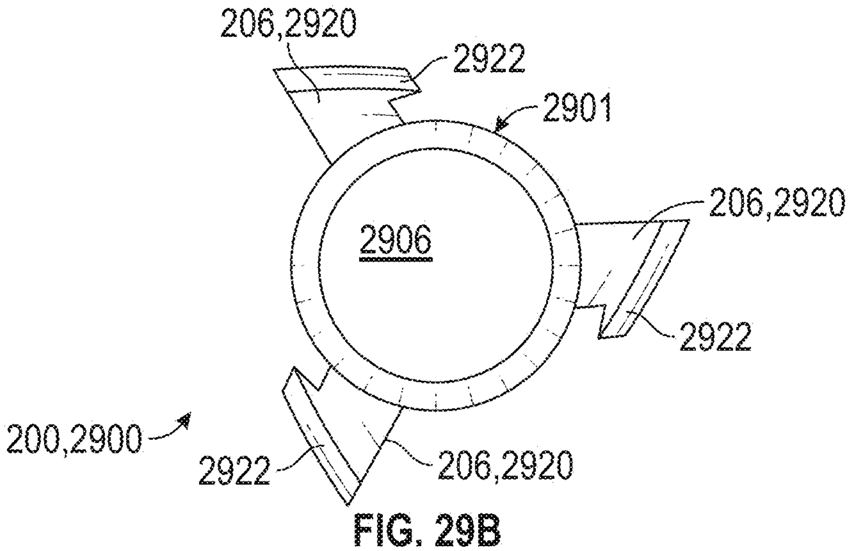
Figure 29C:
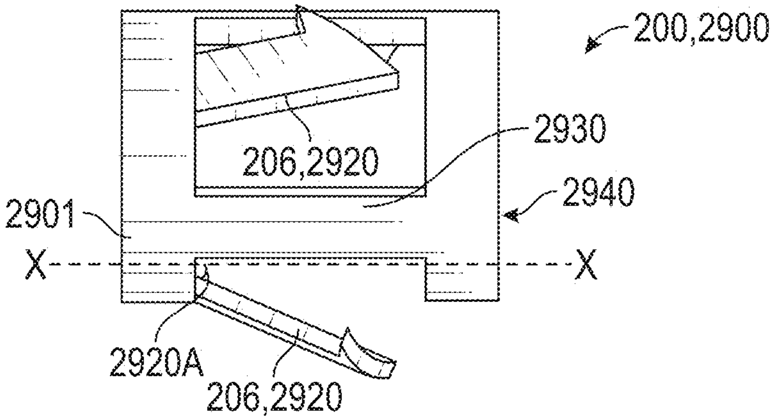

FIGS. 29A, 29B, and 29C illustrate the cartridge 206, 2900 with the fasteners 2920 extended at an angle 2920A from the axial surface 2904 of the body 2901. The features with reference numbers that correspond with the reference numbers for FIG. 28 can correlate with the features in FIG. 28.

As illustrated in FIGS. 29A-C, the cartridge 2900 can include a body 2901 which is operable to be received in a tubular structure 12. The body 2901 can have an outer radial surface 2902 and an axial surface 2904. As will be shown below, the outer radial surface 2902 can be operable to abut against and be substantially parallel to a wall 13 of the tubular structure 12. In at least one example, the outer radial surface 2902 can be substantially perpendicular to the radial direction away from the center of the cartridge 2900. In at least one example, the outer radial surface 2902 can extend substantially parallel to the longitudinal axis X-X. The axial surface 2904 can extend at an angle from the outer radial surface 2902. In at least one example, the axial surface 2904 can extend substantially perpendicular to the longitudinal axis X-X. In at least one example, the axial surface 2904 can extend substantially parallel to the radial direction away from the center of the cartridge 2900. In at least one example, when the outer radial surface 2902 is abutting the wall 13 of the tubular structure 12, the axial surface 2904 can extend at an angle in relation to the wall 13 of the tubular structure 12.

The body 2901 of the cartridge 2900 can form a body lumen 2906 to permit fluid to flow across the body 2901. When the cartridge 2900 is positioned within the tubular structure 12, fluid can flow through the lumen 14 of the tubular structure 12 as well as through the body lumen 2906 of the cartridge 2900. Accordingly, the cartridge 2900, when positioned in the tubular structure 12, does not obstruct the flow of the fluid through the tubular structure 12.

The cartridge 2900 can also include a support 2940 and one or more columns 2930 that extend between the body 2901 (for example the axial surface 2904) and the support 2940. As illustrated in FIGS. 29A-C, the cartridge 2900 can include three columns 2930. In some examples, the cartridge 2900 can include one, two, or more than three columns without deviating from the scope of the disclosure.

In at least one example, the support 2940 has substantially the same shape and/or size as the body 2901. The support 2940 can have a support outer radial surface 2942 and a support axial surface 2944. In at least one example, the support axial surface 2944 can substantially face the axial surface 2904. The support outer radial surface 2942 can be operable to abut against and be substantially parallel to a wall 13 of the tubular structure 12. In at least one example, the support outer radial surface 2942 can be substantially perpendicular to the radial direction away from the center of the cartridge 2900. In at least one example, the support outer radial surface 2942 can extend substantially parallel to the longitudinal axis X-X. The support axial surface 2944 can extend at an angle from the support outer radial surface 2942. In at least one example, the support axial surface 2944 can extend substantially perpendicular to the longitudinal axis X-X. In at least one example, the support axial surface 2944 can extend substantially parallel to the radial direction away from the center of the cartridge 2900. In at least one example, when the support outer radial surface 2942 is abutting the wall 13 of the tubular structure 12, the support axial surface 2944 can extend at an angle in relation to the wall 13 of the tubular structure 12.

The support 2940 of the cartridge 2900 can form a support lumen 2946 to permit fluid to flow across the support 2940. The support lumen 2946 can be in fluid communication with the body lumen 2906 such that fluid can flow across the entire cartridge 2900. When the cartridge 2900 is positioned within the tubular structure 12, fluid can flow through the lumen 14 of the tubular structure 12 as well as through the body lumen 2906 and the support lumen 2946 of the cartridge 2900. Accordingly, the cartridge 2900, when positioned in the tubular structure 12, does not obstruct the flow of the fluid through the tubular structure 12. The support 2940 can provide additional support to the tubular structure 12 in addition to the body 2901.

One or more fasteners 206, 2920 extend from the axial surface 2904 at an angle from the longitudinal axis X-X. In at least one example, the cartridge 200 can be deployed in the tubular structure 12 with the fasteners 2920 already deployed. In at least one example, the fasteners 206 2920 extending at an angle 2920A can abut against and then puncture the walls 13 of the tubular structure 12. In some examples, the tubular structure 12 can be pulled and/or pushed against the fasteners 2920 so that the fasteners 2920 puncture the walls 13 of the tubular structure 12. The fasteners 2920 can extend from the axial surface 2904 at any suitable angle in relation to the longitudinal axis X-X. For example, the fasteners 2920 can extend at an angle 2920A between 1 degree and 89 degrees in relation to the longitudinal axis X-X, but other angles may be suitable without deviating from the scope of the disclosure. In at least one example, the fasteners 2920 can extend at an angle 2920A between about 30 degrees and about 60 degrees. In some examples, the angle 2920A can be between about 40 degrees and about 50 degrees. In some examples, the angle 2920A can be between about 45 degrees. As will be discussed further below, the angle 2920A of the fasteners 2920 can importantly correspond with the taper of the walls of the rings 300 to create a seal, provide the desired tensile strength, and sufficiently couple the anastomotic coupler 10 with the tubular structure 12. The fasteners 2920 can be operable to puncture the wall 13 of the tubular structure 12. As the fasteners 2920 extend from the axial surface 2904 at an angle from the longitudinal axis X-X, the fasteners 2920 also extend at an angle in relation to the wall 13 of the tubular structure 12 when the cartridge 2900 is positioned in the tubular structure 12. Accordingly, the fasteners 2920 being at an angle in relation to the wall 13 of the tubular structure 12 allow for the fasteners 2920 to puncture through the wall 13 of the tubular structure 12, coupling the cartridge 2900 to the tubular structure 12.

As illustrated in FIGS. 29A-C, an end 2922 of the fasteners 2920 can be barbed to include a barb. In some examples, the end 2922 of the fasteners 2920 can be barbed to include two barbs extending in opposite directions. In some examples, the end 2622 of each of the fasteners 2920 can be substantially linear. In some examples, the end 2922 of the fasteners 2920 can be bent. The ends 2922 of the fasteners 2920 can all be the same or different. For example, the fasteners 2920 can each have an end 2922 that is barbed, linear, curved, bent, and/or hooked. The fasteners 2920 can each have an end 2922 that has other shapes and configurations without deviating from the scope of the disclosure so long as the fasteners 2920 can puncture the wall 13 of the tubular structure 12 and maintain coupling with the wall 13.

While FIGS. 29A-C illustrates a cartridge 2900 with three fasteners 2920, one, two, four, or more fasteners 2920 can be provided without deviating from the scope of the disclosure. While FIGS. 29A-C illustrates a cartridge 2900 with fasteners 2920 all having the same lengths, in some examples, the lengths of the fasteners 2920 can vary.

As illustrated in FIGS. 29A-C, the cartridge 2900 can include three columns 2930. In some examples, the cartridge 2900 can include one, two, or more than three columns without deviating from the scope of the disclosure.

Figure 30:
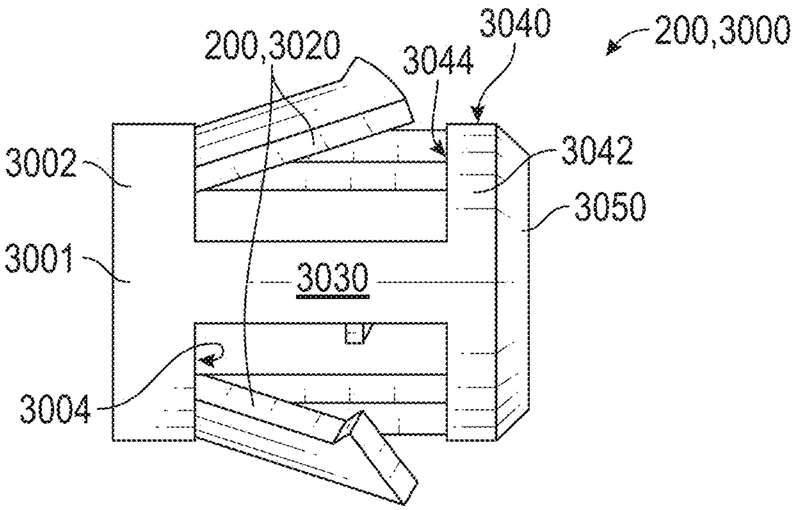
FIG. 30 illustrates the cartridge with the bevel with the arms extended at an angle.

FIG. 30 illustrates a cartridge 200, 3000 substantially similar to the cartridge 2900 of FIGS. 29A-29C. The reference numbers for the cartridge 3000 can correspond with the reference numbers for the cartridge 2900. The cartridge 3000 can include a beveled surface 3050 for the support 3040. In at least one example, the beveled surface 3050 can be opposite the support axial surface 3044 in relation to the support radial surface 3042. The beveled surface 3050 can assist in inserting the cartridge 3000 into the tubular structure 12.

Figure 31A:
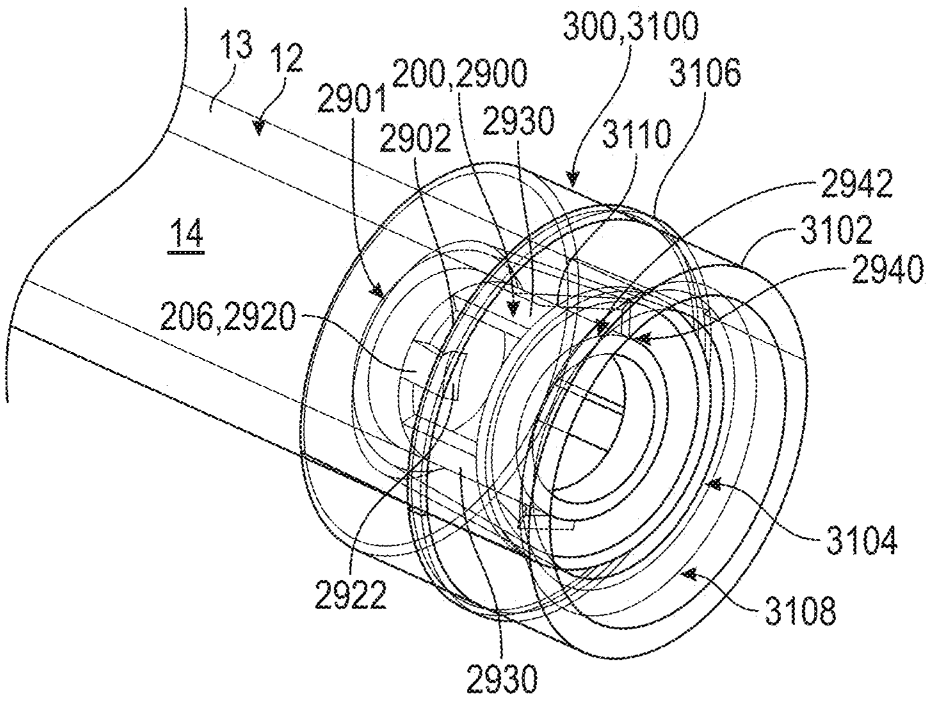
FIGS. 31A and 31B illustrate the cartridge coupling a male ring with a tubular structure.
Figure 31B:
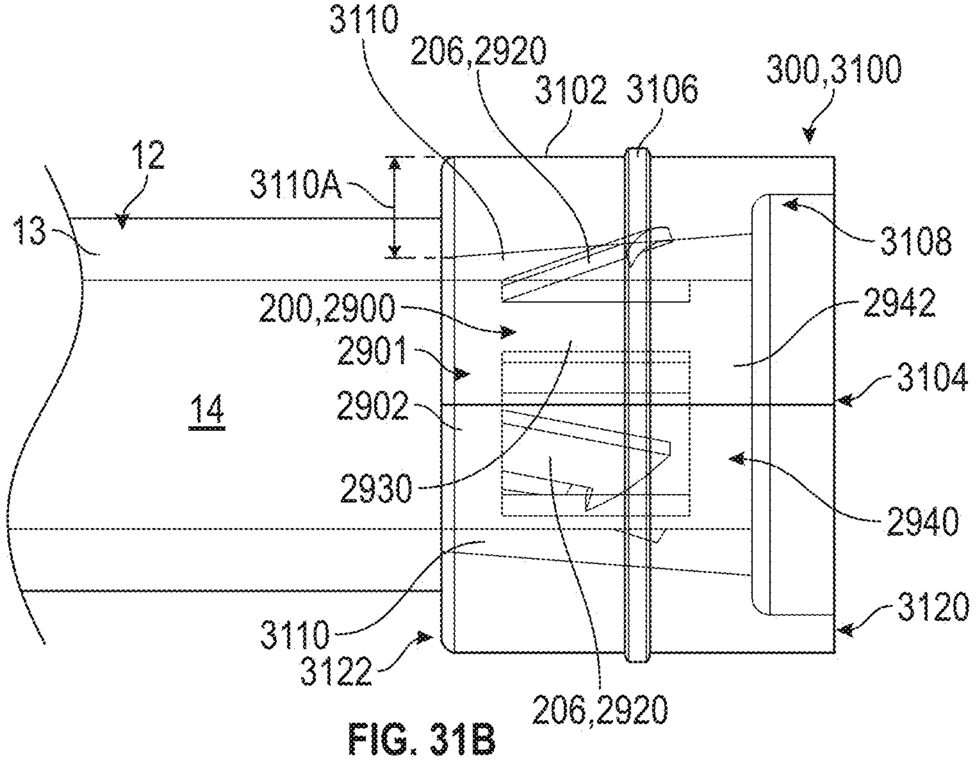
Figure 31C:
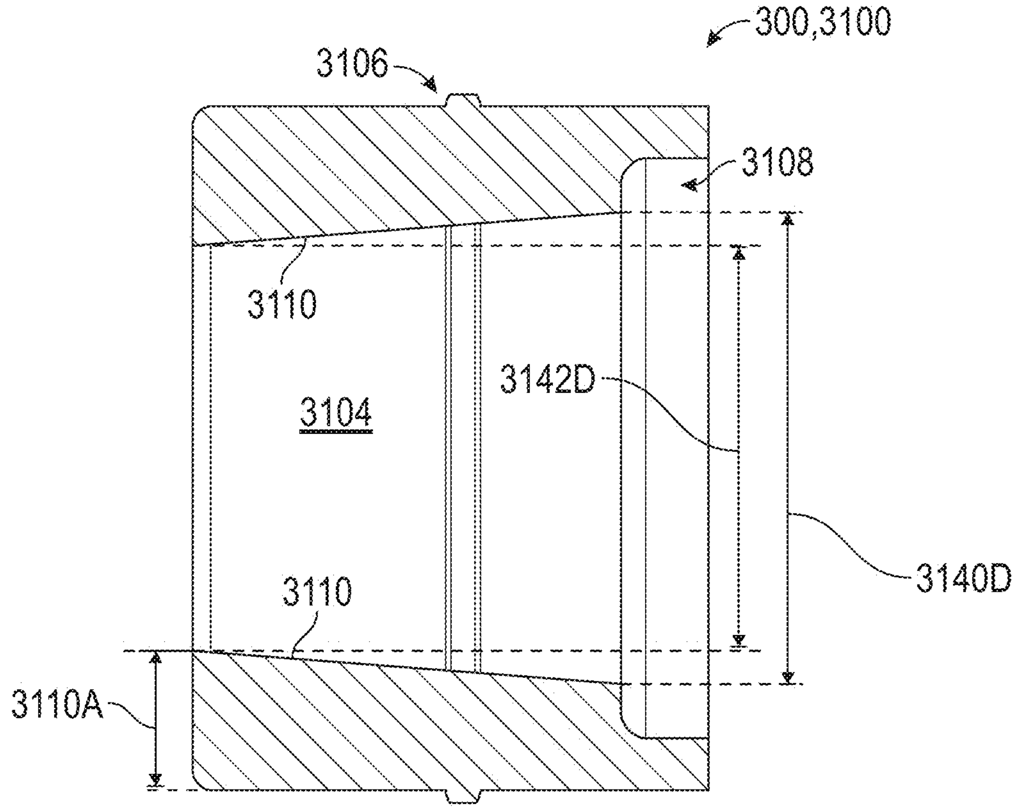
FIG. 31C illustrates the male ring.

FIGS. 31A and 31B illustrate the cartridge 200, 2900 deployed in the tubular structure 12 and coupled with a male ring 300, 3100. FIG. 31C illustrates the male ring 3100.

The male ring 3100 includes a body 3102 that forms an aperture 3104. The male ring 310 is operable to receive a tubular structure 12 through the aperture 3104. While the male ring 3100 as illustrated in FIG. 1A has a substantially circular shape, the male ring 3100 can have any suitable shape such as rectangular, triangular, octagonal, hexagonal, and/or oval. Additionally, the male ring 3100 as illustrated in FIG. 1A is a singular solid piece, in some examples, for ease of application or manufacturing purposes, the male ring 3100 can include two semi-circular or arc-type pieces that are joined together around the tubular structure 12.

Figure 32A:
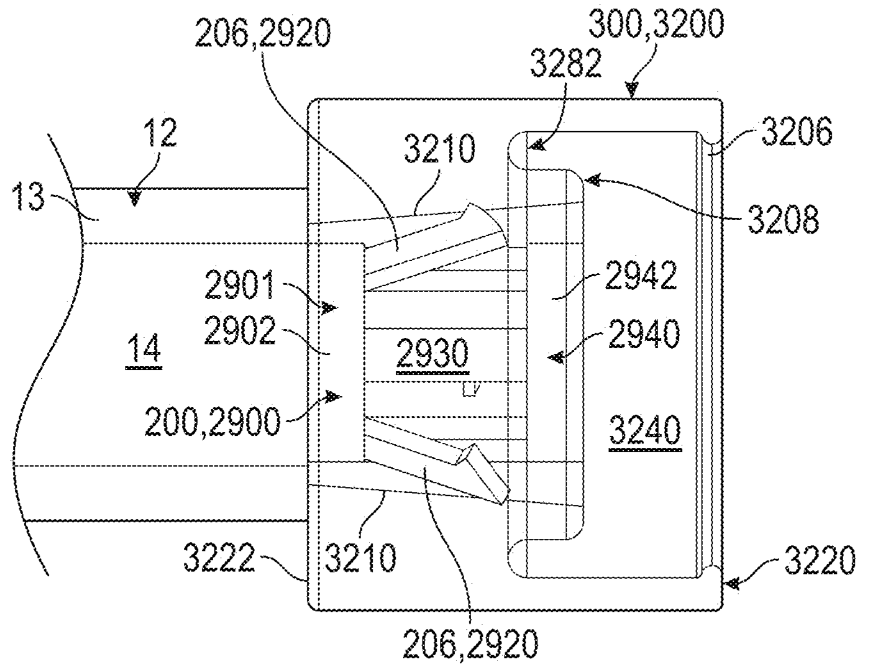
FIG. 32A illustrates the cartridge coupling a female ring with a tubular structure.

The male ring 3100 can include a front end 3120 and a rear end 3122 opposite the front end 3120. The front end 3120 can be operable to be inserted into and/or received by a female ring 3200 (as illustrated in FIGS. 32A-33). The male ring 3100 can include a projection 3106 that extends from the body 3102. In at least one example, the projection 3106 extends around the entire circumference of the body 312. In at least one example, the projection 3106 can have a radius 3106R about 0.1 millimeters.

The size of the male ring 3100 and the lumen 3104 of the male ring 3100 can vary based on the application and the size of the tubular structure 12. For example, the diameter of the lumen 3104 can range from about 0.5 millimeters (mm) (for example for lymphatic connections) to about 60 millimeters (for example for gastrointestinal connections). Due to the range of diameters for the male ring 3100, and the range of diameters for the tubular structure 12, the appropriate male ring 3100 can be selected by measuring the internal diameter of the tubular structure 12. This can be accomplished, for example, with an intraluminal measurement guide/device. If there is a significant size mismatch (1 mm or greater) between the tubular structure 12 and the male ring 3100, then a short, cylindrical tube connector with a corresponding male and female end can be used to allow for gradual transition in size in any direction to accommodate the size difference. For example, a cylindric tube can be provided that tapers in size such that one end is 1 mm-2 mm larger/smaller than the other end, which would enable a connection of a 1 mm vessel to a 2.5 mm-3.5 mm vessel during microsurgical procedures without problem and vice versa.

The male ring 3100 can include a male receiving portion 3108 formed as a portion of the lumen 3104. In at least one example, the male receiving portion 3108 can be formed adjacent to the front end 3120 of the body 3102. The male receiving portion 318 can be in the form of a notch or a recess. The male receiving portion 318 can have a width 3108W between about 0.3 millimeters and about 1.0 millimeters. In some examples, the width 3108W can be between about 0.4 millimeters and about 0.7 millimeters. In some examples, the width 3108W can be about 0.5 millimeters. The width 3108W can be scaled based on the size of the male ring 3100 which corresponds with the size of the tubular structure 12. The lumen 3104, as illustrated in FIGS. 31A-C can have walls 3110 that taper at an angle such that a diameter of the lumen 3104 decreases from a front diameter 3140D at the end of the male receiving portion 3108 near the front end 3120 of the body 3102 to a rear diameter 3142D at the rear end 3122 of the body 3102.

The walls 3110 of the lumen 3104 can taper at an angle 3110A between about 2 degrees and about 8 degrees. In some examples, the walls 3110 can taper at an angle 3110A between about 3 degrees and about 6 degrees. In some examples, the walls 131 can taper at an angle 3110A between about 4 degrees and about 5 degrees. In some examples, the walls 131 can taper at an angle 3110A about 4.46 degrees. The angle 3110A can vary based on the size and shape of the tubular structure 12 and the angle 2920A of the fasteners 2920. The taper can create a seal with the tubular structure 12 and provide tensile strength.

In at least one example, the walls 3110 are operable to compress the fasteners 2920 extending from the tubular structure 12 against the external side of the walls 13 of the tubular structure 12. For example, the fasteners 2920 can puncture the walls 13 of the tubular structure 12 at the angle 2920A of the fasteners 2920 (for example, about 45 degrees). The male ring 3100 can be slid along the tubular structure 12 to be positioned over the cartridge 2900 such that the walls 3110 of the male ring 3100 abut against and compress the fasteners 2920. The angle 3110A of the walls 3110 of the male ring 3100 corresponding to the angle 2920A of the fasteners 2900 can provide desired coupling of the cartridge 2900 and the male ring 3100 with the tubular structure 12 as well as the desired tensile strength. In at least one example, the fasteners 2920 may not puncture the walls 3110 of the male ring 3100. In some examples, the fasteners 2920 may puncture the walls 3110 of the male ring 3100.

The annulus 14 of the tubular structure 12 can be aligned and/or in fluid communication with the annulus 3104 of the male ring 3100 such that fluid can flow between the annulus 14 of the tubular structure 12 and the annulus 3104 of the male ring 3100.

The male ring 3100 and/or the cartridge 2900 can be made from mechanically suitable materials that are approved, and have sufficient strength, for use in the human or animal body. For example, the following materials, alone or in any combination, can be used: metals, in particular titanium or stainless steel, including the special alloys used for implants and medical instruments, nitinol, carbon materials, including carbon fiber meshes, soft plastic, for example silicone, hard plastic, for example Teflon, ceramic material, and/or bioresorbable material. The male ring 3100 and/or the fastener 20 can be provided entirely or partially with a coating and/or structure that prevents or at least reduces the adherence of blood constituents. Such a coating can be composed of a material that smooths the surface. In at least one example, the coating can also contain anti-thrombotic medicaments (e.g. heparin, hydrophilic coating, etc.).

Figure 32B:
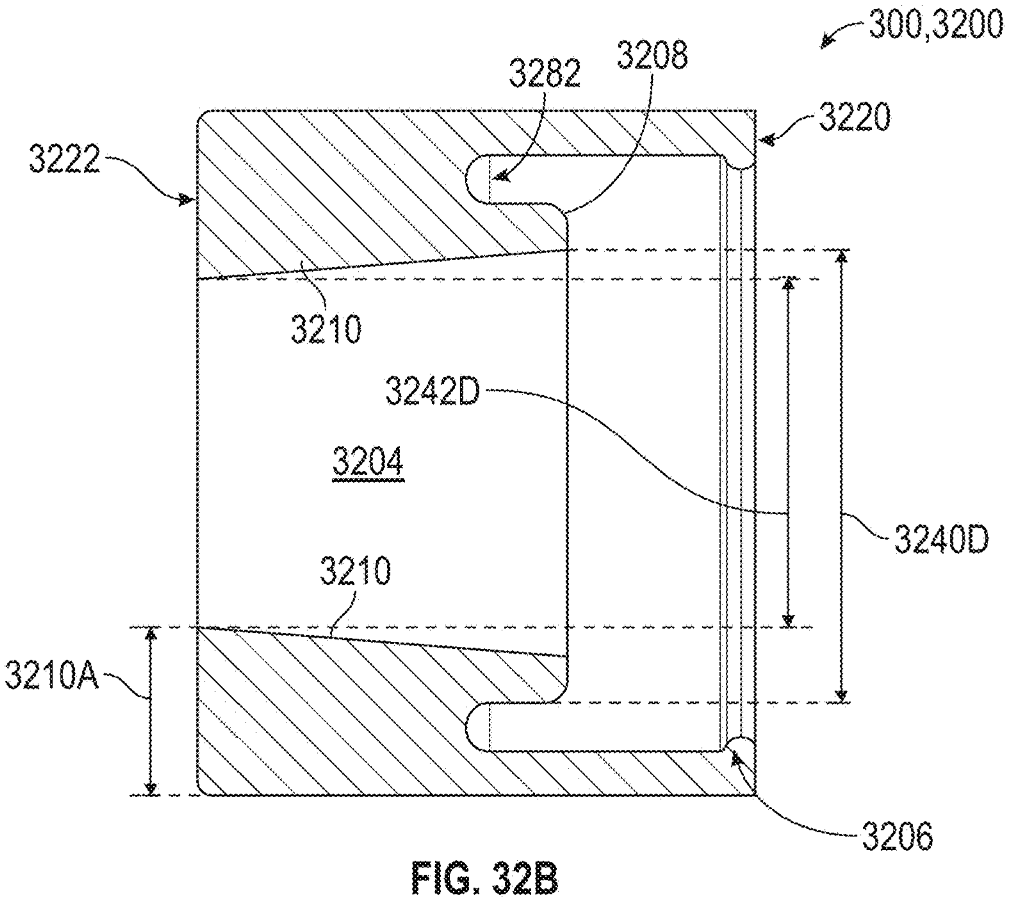
FIG. 32B illustrates the female ring.
Figure 33:
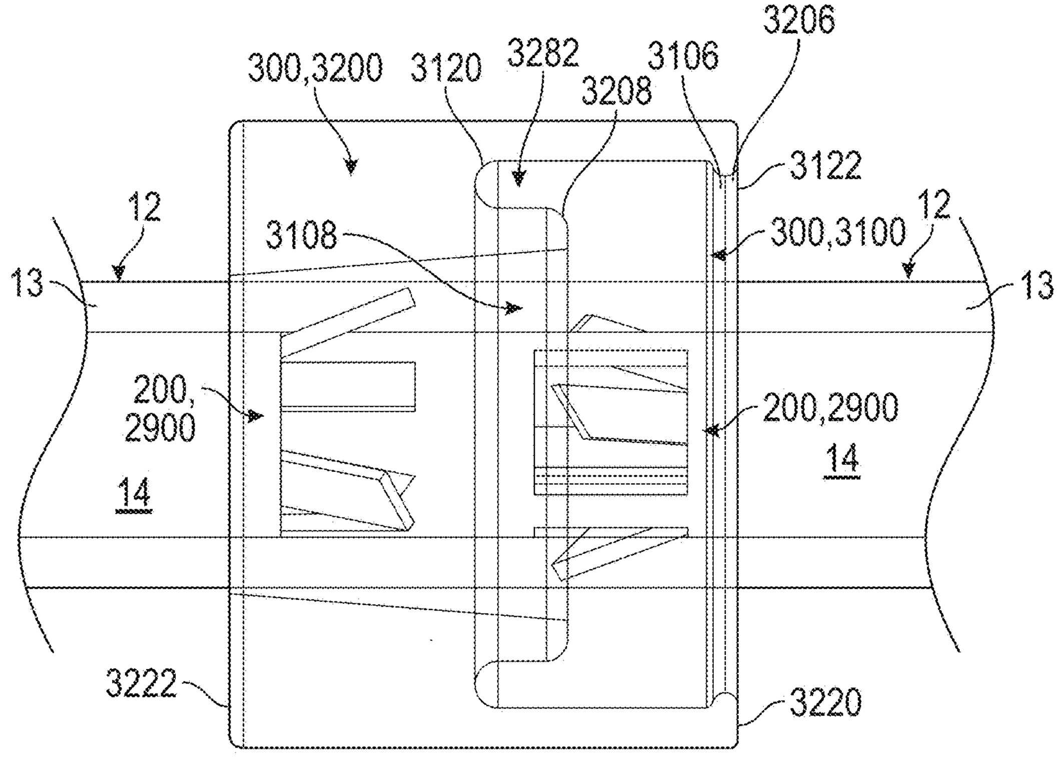
FIG. 33 illustrates the male ring coupled with the female ring to couple the two tubular structures together.

FIGS. 32A and 32B illustrate the cartridge 200, 2900 deployed in the tubular structure 12 and coupled with a female ring 300, 3200.

The female ring 3200 includes a body 3202 that forms an aperture 3204. The female ring 320 is operable to receive a tubular structure 12 through the aperture 3204. While the female ring 3200 as illustrated in FIG. 1A has a substantially circular shape, the female ring 3200 can have any suitable shape such as rectangular, triangular, octagonal, hexagonal, and/or oval. Additionally, the female ring 3200 as illustrated in FIG. 1A is a singular solid piece, in some examples, for ease of application or manufacturing purposes, the female ring 3200 can include two semi-circular or arc-type pieces that are joined together around the tubular structure 12.

The female ring 3200 can include a front end 3220 and a rear end 3222 opposite the front end 3220. The front end 3220 can be operable to be receive a male ring 3100 (as illustrated in FIG. 33).

The size of the female ring 3200 and the lumen 3204 of the female ring 3200 can vary based on the application and the size of the tubular structure 12. For example, the diameter of the lumen 3204 can range from about 0.5 millimeters (mm) (for example for lymphatic connections) to about 60 millimeters (for example for gastrointestinal connections). Due to the range of diameters for the female ring 3200, and the range of diameters for the tubular structure 12, the appropriate female ring 3200 can be selected by measuring the internal diameter of the tubular structure 12. This can be accomplished, for example, with an intraluminal measurement guide/device. If there is a significant size mismatch (1 mm or greater) between the tubular structure 12 and the female ring 3200, then a short, cylindrical tube connector with a corresponding male and female end can be used to allow for gradual transition in size in any direction to accommodate the size difference. For example, a cylindric tube can be provided that tapers in size such that one end is 1 mm-2 mm larger/smaller than the other end, which would enable a connection of a 1 mm vessel to a 2.5 mm-3.5 mm vessel during microsurgical procedures without problem and vice versa.

The female ring 3200 can include a female receiving portion 3240 formed as a portion of the lumen 3204. In at least one example, the female receiving portion 3240 can be formed adjacent to the front end 3220 of the body 3202. The female receiving portion 3240 can be in the form of a notch or a recess. The female receiving portion 3240 can have a lip 3206 that extends into the female receiving portion 3240. As illustrated in FIG. 33, the lip 3206 can correspond with the protrusion 3106 such that when the male ring 3100 is received in the female receiving portion 3240, the protrusion 3106 extends into and past the lip 3206. Once the protrusion 3106 is inserted past the lip 3206, the abutment between the protrusion 3106 and the lip 3206 couple the male ring 3100 with the female ring 3200. Accordingly, the lip 3206 and the protrusion 3106 provide a snap fit between the male ring 3100 and the female ring 3200.

The female receiving portion 3240 also includes a recess 3282 that is operable to receive the front end 3120 of the male ring 3100. As illustrated in FIG. 33, an abutment 3208 adjacent to the recess 3282 is operable to be received in the male receiving portion 3108. With the recess 3282 and the abutment 308 corresponding with the front end 3120 and the male receiving portion 3108, the male ring 3100 and the female ring 3200 are aligned and coupled with one another. With the recess 3282 and the abutment 3208 corresponding with the front end 3120 and the male receiving portion 3108, the male ring 3100 and the female ring 3200 are operable to create a seal such that fluid does not leak out of the anastomotic coupler. The male ring 3100 and the female ring 3200 are operable to join together with compression to create a seal and prevent leakage.

The walls 3210 of the lumen 3204 can taper at an angle 3210A between about 2 degrees and about 8 degrees. In some examples, the walls 3210 can taper at an angle 3210A between about 3 degrees and about 6 degrees. In some examples, the walls 132 can taper at an angle 3210A between about 4 degrees and about 5 degrees. In some examples, the walls 132 can taper at an angle 3210A about 4.46 degrees. The angle 3210A of the taper can vary based on the size and/or shape of the tubular structure 12 and/or the angle 2920A of the fasteners 2920. The taper can create a seal with the tubular structure 12 and provide tensile strength.

In at least one example, the walls 3210 are operable to compress the fasteners 2920 extending from the tubular structure 12 against the external side of the walls 13 of the tubular structure 12. For example, the fasteners 2920 can puncture the walls 13 of the tubular structure 12 at the angle 2920A of the fasteners 2920 (for example, about 45 degrees). The female ring 3200 can be slid along the tubular structure 12 to be positioned over the cartridge 2900 such that the walls 3210 of the female ring 3200 abut against and compress the fasteners 2920. The angle 3210A of the walls 3210 of the female ring 3200 corresponding to the angle 2920A of the fasteners 2900 can provide desired coupling of the cartridge 2900 and the female ring 3200 with the tubular structure 12 as well as the desired tensile strength. In at least one example, the fasteners 2920 may not puncture the walls 3210 of the female ring 3200. In some examples, the fasteners 2920 may puncture the walls 3210 of the female ring 3200.

The annulus 14 of the tubular structure 12 can be aligned and/or in fluid communication with the annulus 3204 of the female ring 3200 such that fluid can flow between the annulus 14 of the tubular structure 12 and the annulus 3204 of the female ring 3200.

The female ring 3200 and/or the cartridge 2900 can be made from mechanically suitable materials that are approved, and have sufficient strength, for use in the human or animal body. For example, the following materials, alone or in any combination, can be used: metals, in particular titanium or stainless steel, including the special alloys used for implants and medical instruments, nitinol, carbon materials, including carbon fiber meshes, soft plastic, for example silicone, hard plastic, for example Teflon, ceramic material, and/or bioresorbable material. The female ring 3200 and/or the fastener 20 can be provided entirely or partially with a coating and/or structure that prevents or at least reduces the adherence of blood constituents. Such a coating can be composed of a material that smooths the surface. In at least one example, the coating can also contain anti-thrombotic medicaments (e.g. heparin, hydrophilic coating, etc.).

As illustrated in FIG. 33, when the rings 3100, 3200 are coupled with one another, the lumens 14 of the two tubular structures 12 are aligned in fluid communication with one another. In at least one example, the rings 3100, 3200 can create a seal to prevent fluid leakage. Accordingly, the anastomotic coupler 10 provides a more reliable, faster, more secure anastomotic coupling device to create a sealed, leak-proof, open connection between the ends of the tubular structures 12 and allow for "stented" unobstructed flow of luminal contents through the connection/anastomosis (e.g. blood, lymph, fluid, stool contents, gastric contents, etc.). This connection can be strong enough to withstand tension, traction, and high flow pressure, which may occur with distal obstruction.

While the disclosure discusses two separate anchors 200, 2800, 2900, 3000 to correspond with the male ring 3100 and the female ring 3200, in some examples, one single anchor 2900 with a body 2901, a support 2940, and one or more columns 2930 can be utilized to couple both the male ring 3100 and the female ring 3200. The anchor 2920 can include two sets of fasteners 2920 that extend at the angle 2920A such that each set of fasteners 2920 face opposing directions. For example, the first set of fasteners 2920 can extend from the axial face 2904 of the body 2901 while the second set of fasteners 2920 can extend from the support axial face 2944 of the support 2940.

Figure 34A:
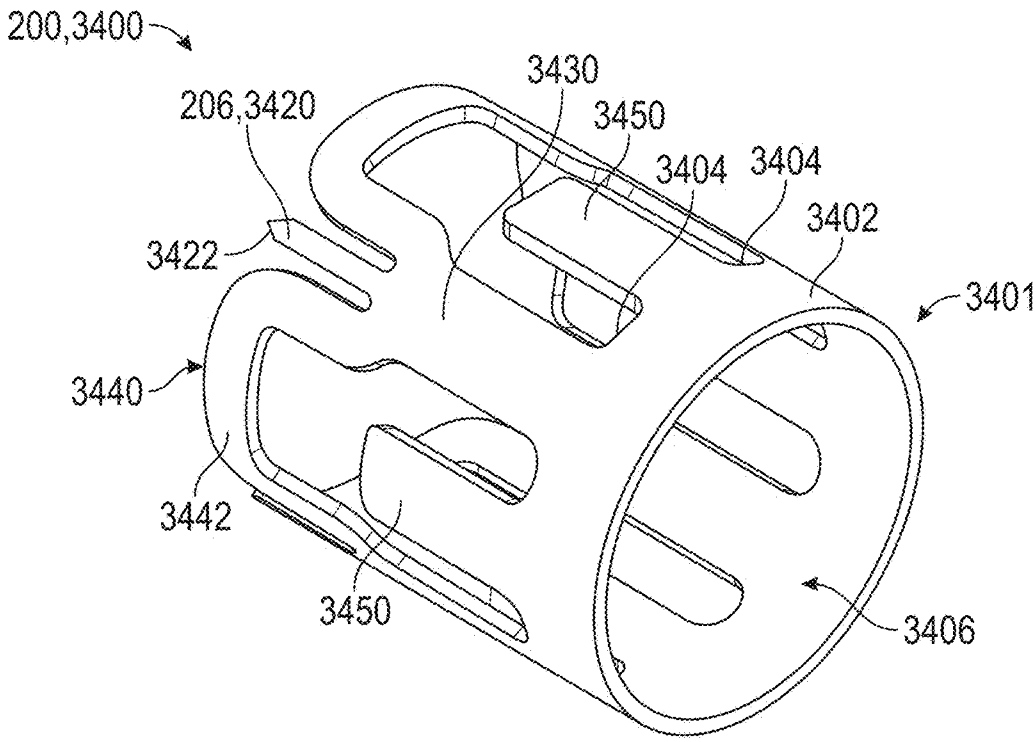
FIGS. 34A, 34B, and 34C illustrate an exemplary cartridge.
Figure 34B:
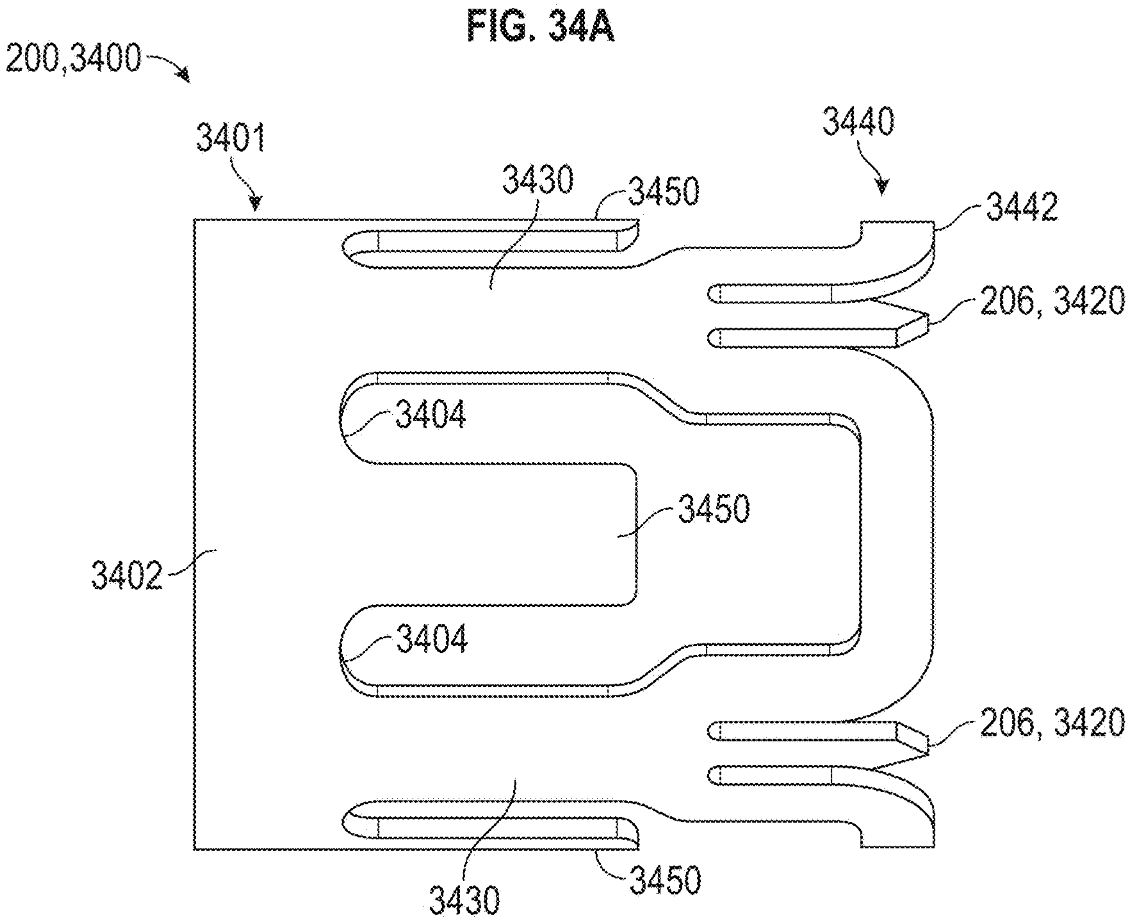
Figure 34C:
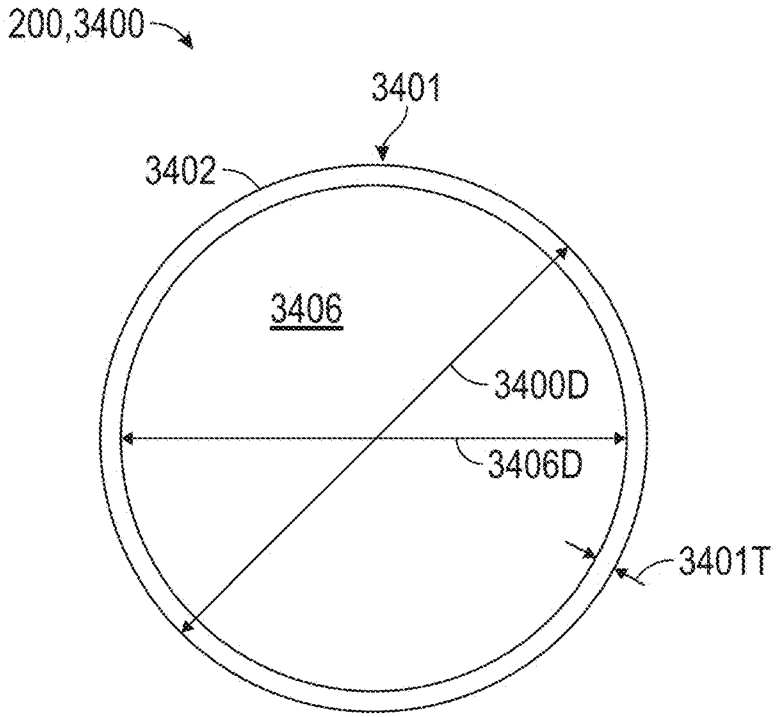
Figure 35A:
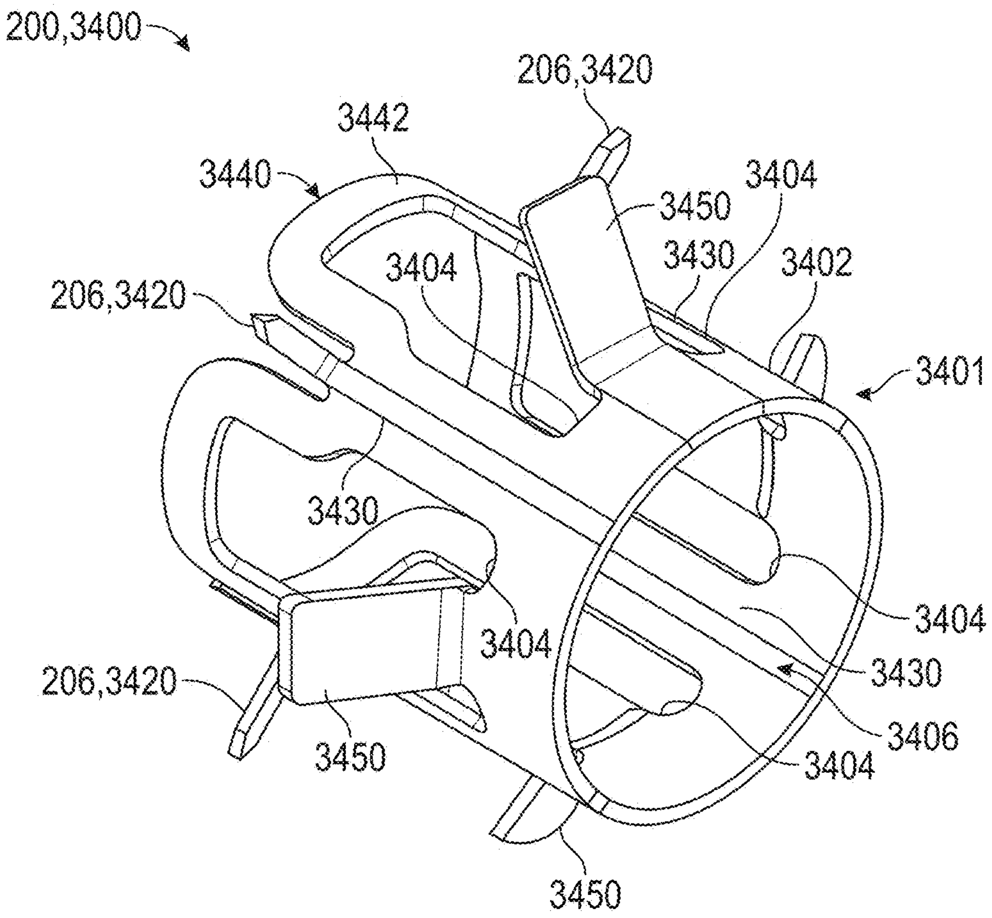
FIGS. 35A, 35B, 35C, and 35D illustrate the cartridge with the arms and the friction component extended at corresponding angles.
Figure 35B:
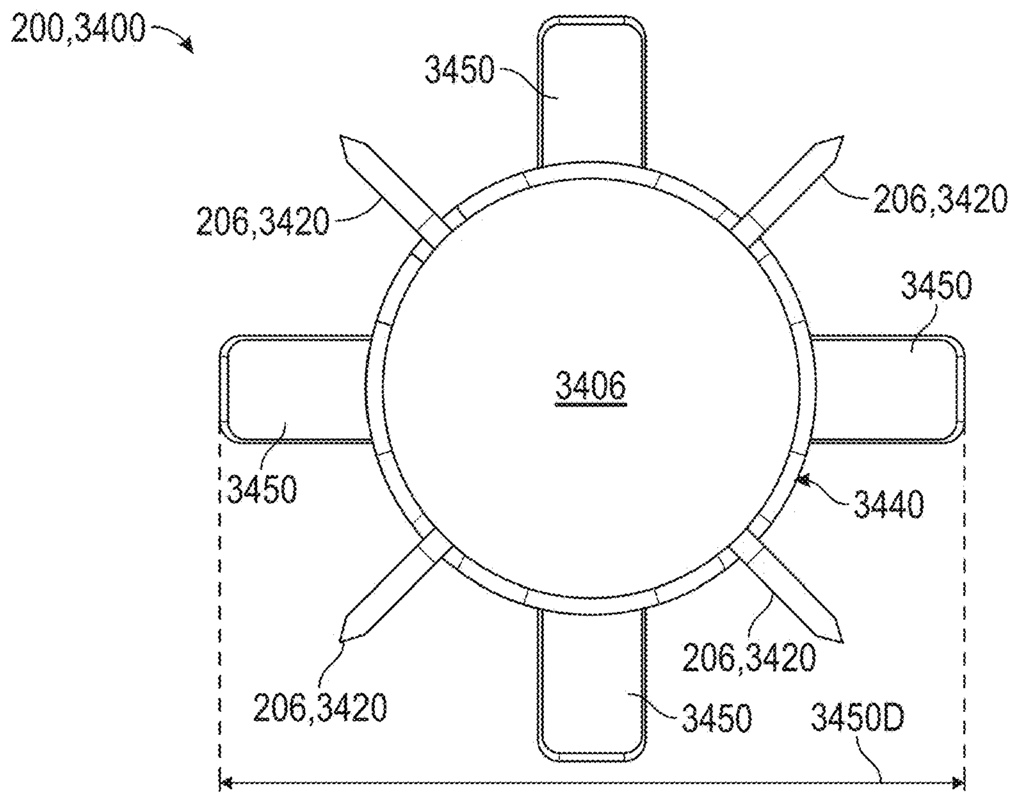
Figure 35C:
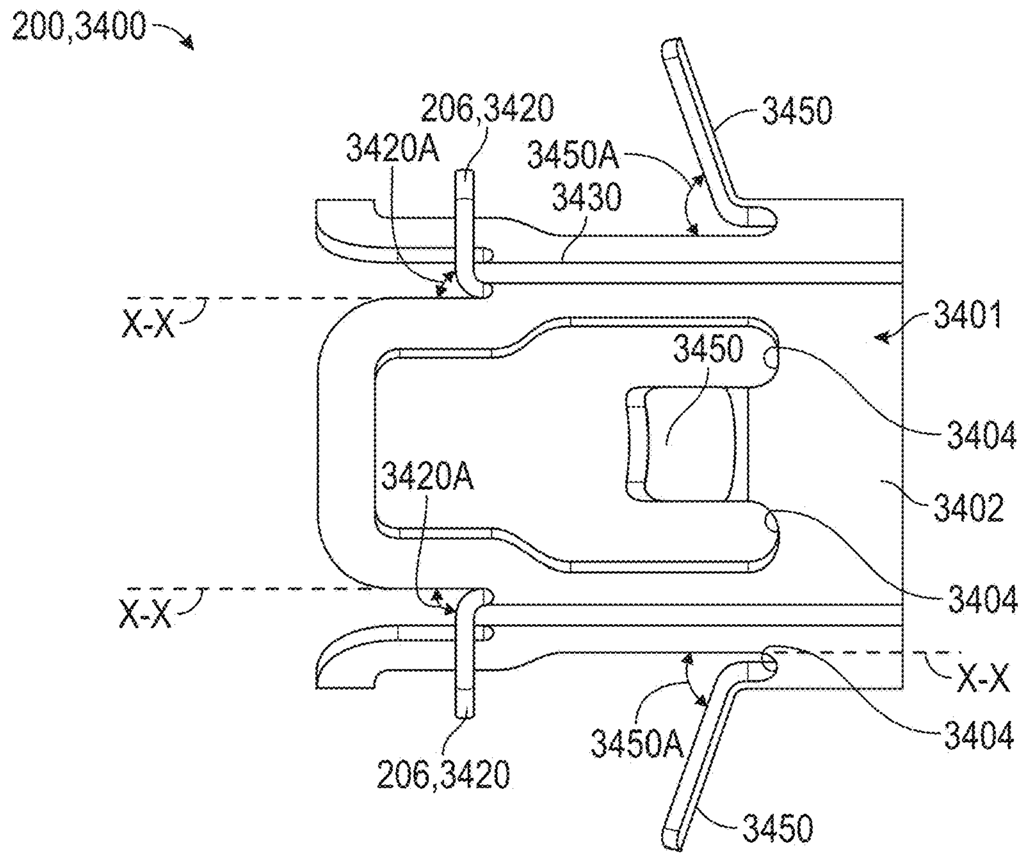
Figure 35D:
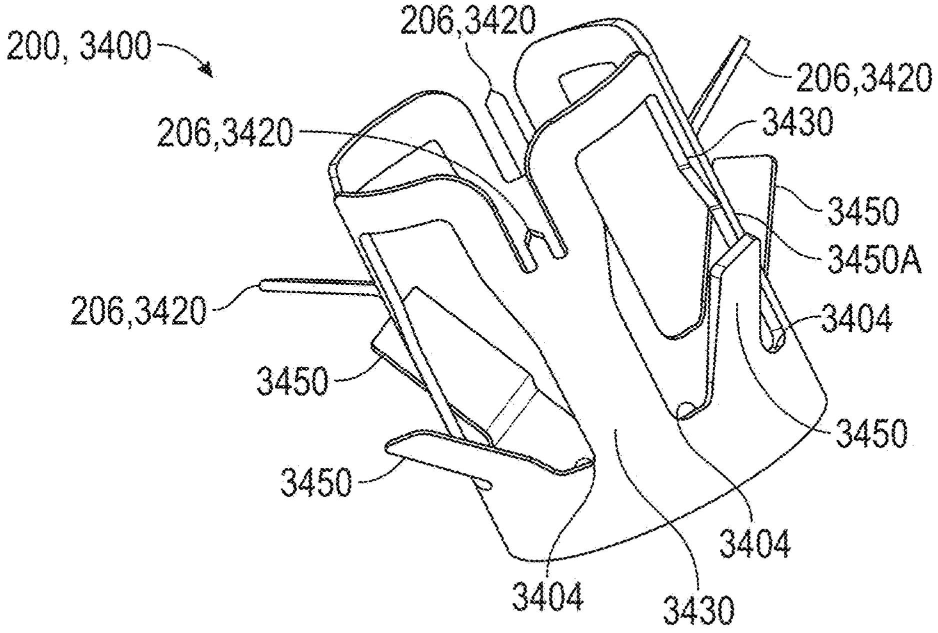

FIGS. 34A-34C illustrate a cartridge 200, 3400 for an anastomotic coupler 10. The cartridge 200, 3400 can include any combination of features that are described in any previous disclosure herein. Similarly, any of the previous disclosures can include any of the features described herein for cartridge 200, 3400.

As illustrated in FIGS. 34A-34C, the cartridge 3400 can include a body 3401 which is operable to be received in a tubular structure 12. The body 3401 can have an outer radial surface 3402 and an axial surface 3404. As will be shown below, the outer radial surface 3402 can be operable to abut against and/or be substantially parallel to a wall 13 of the tubular structure 12. In at least one example, the outer radial surface 3402 can be substantially perpendicular to the radial direction away from the center of the cartridge 3400. In at least one example, the outer radial surface 3402 can extend substantially parallel to the longitudinal axis X-X. The axial surface 3404 can extend at an angle from the outer radial surface 3402. In at least one example, the axial surface 3404 can extend substantially perpendicular to the longitudinal axis X-X. In at least one example, the axial surface 3404 can extend substantially parallel to the radial direction away from the center of the cartridge 3400. In at least one example, when the outer radial surface 3402 is abutting the wall 13 of the tubular structure 12, the axial surface 3404 can extend at an angle in relation to the wall 13 of the tubular structure 12.

The body 3401 of the cartridge 3400 can form a body lumen 3406 to permit fluid to flow across the body 3401. When the cartridge 3400 is positioned within the tubular structure 12, fluid can flow through the lumen 14 of the tubular structure 12 as well as through the body lumen 3406 of the cartridge 3400. Accordingly, the cartridge 3400, when positioned in the tubular structure 12, does not obstruct the flow of the fluid through the tubular structure 12.

The cartridge 3400 can also include a support 3440 and one or more columns 3430 that extend between the body 3401 (for example extending from the axial surface 3404) and the support 3440. As illustrated in FIGS. 34A-34C, the cartridge 3400 can include four columns 3430. In some examples, the cartridge 3400 can include one, two, three, or more than four columns without deviating from the scope of the disclosure.

In at least one example, the support 3440 has substantially the same shape and/or size as the body 3401. The support 3440 can have a support outer radial surface 3442 and a support axial surface 3444. In at least one example, the support axial surface 3444 can substantially face the axial surface 3404. The support outer radial surface 3442 can be operable to abut against and/or be substantially parallel to a wall 13 of the tubular structure 12. In at least one example, the support outer radial surface 3442 can be substantially perpendicular to the radial direction away from the center of the cartridge 3400. In at least one example, the support outer radial surface 3442 can extend substantially parallel to the longitudinal axis X-X. The support axial surface 3444 can extend at an angle from the support outer radial surface 3442. In at least one example, the support axial surface 3444 can extend substantially perpendicular to the longitudinal axis X-X. In at least one example, the support axial surface 3444 can extend substantially parallel to the radial direction away from the center of the cartridge 3400. In at least one example, when the support outer radial surface 3442 is abutting the wall 13 of the tubular structure 12, the support axial surface 3444 can extend at an angle in relation to the wall 13 of the tubular structure 12.

The support 3440 of the cartridge 3400 can form a support lumen 3446 to permit fluid to flow across the support 3440. The support lumen 3446 can be in fluid communication with the body lumen 3406 such that fluid can flow across the entire cartridge 3400. When the cartridge 3400 is positioned within the tubular structure 12, fluid can flow through the lumen 14 of the tubular structure 12 as well as through the body lumen 3406 and the support lumen 3446 of the cartridge 3400. Accordingly, the cartridge 3400, when positioned in the tubular structure 12, does not obstruct the flow of the fluid through the tubular structure 12. The support 3440 can provide additional support to the tubular structure 12 in addition to the body 3401.

One or more fasteners 206, 3420 and one or more frictional elements 3450 can extend radially outward from the cartridge 3400, as shown in FIGS. 35A-37. The fasteners 3420 can be operable to at least partially puncture the wall 13 of the tubular structure 12, coupling the cartridge 3400 to the tubular structure 12. The frictional elements 3450 can be operable to abut against the wall 13 of the tubular structure 12 without puncturing the wall 13. The frictional elements 3450 can be operable to assist with securing the tubular structure 12 to a ring 300 through radial compression, without the need to pierce the tissue of the tubular structure 12.

As illustrated in FIGS. 34A-37, in at least one example, the fasteners 206, 3420 can extend from the columns 3430. While FIGS. 34A-37 illustrate the fasteners 206, 3420 extending from the columns 3430, the fasteners 206, 3420 can extend from other portions of the cartridge 200, for example from the axial surface 3404 and/or the support surface 3440, or any configuration as discussed herein, without deviating from the scope of the disclosure.

The fasteners 206, 3420, as illustrated in FIGS. 34A-34C, are not extended at an angle from the cartridge 200, 3400. The fasteners 206, 3420 extend along the longitudinal axis X-X. In at least one example, the fasteners 206, 3420 can be initially manufactured, shipped, and/or stored with the fasteners 206, 3420 extending along the longitudinal axis X-X for ease of transport. The fasteners 206, 3420, when implemented, can be bent to extend from the cartridge 200, 3400 (e.g., the columns 3430) at an angle 3420A, as shown in FIGS. 35A-37.

In at least one example, the fasteners 206, 3420 can be shipped, stored, and/or implemented with the fasteners 206, 3420 extended at an angle 3420A from the cartridge 200, 3400 (for example, at an angle 3420A in relation to the longitudinal axis X-X). When the fasteners 206, 3420 are received in the tubular structure 12, the fasteners 206, 3420 can be transitioned to extend from the cartridge 200, 3400 (e.g., the columns 3430) at an angle 3420A to at least partially puncture the walls 13 of the tubular structure 12. For example, the cartridge 200, 3400 can be shipped and/or stored in a sheath that holds the fasteners 206, 3420 in and not expanded at the angle 3420A. For implementation, the sheath may be removed and/or the fasteners 206, 3420 released to extend at the angle 3420A.

As illustrated in FIGS. 35A-37, the angle 3420A formed between the fasteners 206, 3420 and the longitudinal axis X-X can be between about 1 degree and about 90 degrees. In some examples, the angle 3420A can be between about 30 degrees and about 90 degrees. In some examples, the angle 3420A can be between about 45 degrees and about 90 degrees. In some examples, the angle 3420A can be between about 60 degrees and about 90 degrees. In some examples, the angle 3420A can be about 65 degrees and about 80 degrees.

As illustrated in FIGS. 34A-37, an end 3422 of the fasteners 3420 can be pointed so that the fasteners 3420 can at least partially puncture the wall 13 of the tubular structure 12. For example, the fasteners 3420 may not pierce the full thickness of the wall 13 of the tubular structure 12, but can still hold the tubular structure 12 onto the cartridge 200, 3400. In some examples, the fasteners 3420 can be operable to puncture both the wall 13 of the tubular structure 12 and at least partially puncture a portion of the ring 300. In some examples, the end 3422 of the fasteners 3420 can be barbed to include a barb. In some examples, the end 3422 of the fasteners 3420 can be barbed to include two barbs extending in opposite directions. In some examples, the end 3422 of each of the fasteners 3420 can be substantially linear. In some examples, the end 3422 of the fasteners 3420 can be bent. The ends 3422 of the fasteners 3420 can all be the same or different. For example, the fasteners 3420 can each have an end 3422 that is barbed, linear, curved, bent, and/or hooked. The fasteners 3420 can each have an end 3422 that has other shapes and configurations without deviating from the scope of the disclosure so long as the fasteners 3420 can puncture the wall 13 of the tubular structure 12 and maintain coupling with the wall 13.

While FIGS. 34A-37 illustrate a cartridge 3400 with four fasteners 3420, one, two, three, or more than four fasteners 3420 can be provided without deviating from the scope of the disclosure. While FIGS. 34A-37 illustrate a cartridge 3400 with fasteners 3420 all having the same lengths, in some examples, the lengths of the fasteners 3420 can vary. Additionally, in some examples, the angles 3420A of the fasteners 3420 can vary between fasteners 3420.

As illustrated in FIGS. 34A-37, in at least one example, the frictional elements 3450 can extend from the axial surface 3404. In some examples, the frictional elements 3450 can extend from the body 3401 between the columns 3430. While FIGS. 34A-37 illustrate the frictional elements 3450 extending from the axial surface 3404 between the columns 3430, the frictional elements 3450 can extend from other portions of the cartridge 200, for example from the columns 3430 and/or the support surface 3440, or any configuration as discussed herein, without deviating from the scope of the disclosure.

The frictional elements 3450, as illustrated in FIGS. 34A-34C, are not extended at an angle from the cartridge 200, 3400. The frictional elements 3450 extend along the longitudinal axis X-X. In at least one example, the frictional elements 3450 can be initially manufactured, shipped, and/or stored with the frictional elements 3450 extending along the longitudinal axis X-X for ease of transport. The frictional elements 3450, when implemented, can be bent to extend from the cartridge 200, 3400 (e.g., the columns 3430) at an angle 3450A, as shown in FIGS. 35A-37.

In at least one example, the frictional elements 3450 can be shipped, stored, and/or implemented with the frictional elements 3450 extended at an angle 3450A from the cartridge 200, 3400 (for example, at an angle 3450A in relation to the longitudinal axis X-X). When the frictional elements 3450 are received in the tubular structure 12, the fasteners 206, 3420 can be transitioned to extend from the cartridge 200, 3400 (e.g., the axial surface 3404) at an angle 3450A to abut against the walls 13 of the tubular structure 12. For example, the cartridge 200, 3400 can be shipped and/or stored in a sheath that holds the frictional elements 3450 in and not expanded at the angle 3450A. For implementation, the sheath may be removed and/or the frictional elements 3450 released to extend at the angle 3450A.

As illustrated in FIGS. 35A-37, the angle 3450A formed between the frictional elements 3450 and the longitudinal axis X-X can be between about 1 degree and about 90 degrees. In some examples, the angle 3420A can be between about 30 degrees and about 90 degrees. In some examples, the angle 3420A can be between about 45 degrees and about 90 degrees. In some examples, the angle 3420A can be between about 60 degrees and about 90 degrees.

As illustrated in FIGS. 34A-37, the frictional elements 3450 can have a blunted (e.g., not sharp) end so that the fasteners 3420 can abut against the walls 13 of the tubular structure 12 without puncturing the wall 13. For example, the frictional elements 3450 can include a tab shape, with a substantially flat end. In some examples, the frictional elements 3450 can include a rounded end. In some examples, the frictional elements 3450 can include a bump, barb, ridge, or any other suitable frictional element to interact with the inner diameter of the ring 300 to help secure the cartridge 200, 3400 within the ring 300. For example, the frictional elements 3450 may abut against the wall 13 of the tubular structure 12 such that the frictional elements 3450 provide radial compression, key fit, and/or other mechanisms. Accordingly, the frictional elements 3450 can push the wall 13 of the tubular structure 12 against the ring 300 to help secure the coupling of the tubular structure 12 with the ring 300. The frictional elements 3450 can each have an end that has other shapes and configurations without deviating from the scope of the disclosure so long as the frictional elements 3450 can provide radial compression between the wall 13 of the tubular structure 12 and maintain coupling with the wall 13 and the ring 300.

While FIGS. 34A-37 illustrate a cartridge 3400 with four frictional elements 3450, one, two, three, or more than four frictional elements 3450 can be provided without deviating from the scope of the disclosure. While FIGS. 34A-37 illustrate a cartridge 3400 with frictional elements 3450 all having the same lengths, in some examples, the lengths of the frictional elements 3450 can vary. Additionally, in some examples, the angles 3450A of the frictional elements 3450 can vary between frictional elements 3450.

While FIGS. 34A-37 illustrate the cartridge 3400 with the frictional elements 3450 that may be received by the ring 300 through the tubular structure 12, in some examples, the ring 300 may include a frictional element that is received by the cartridge 3400 for a keyed fit.

In at least one example, any portion of the cartridge (e.g., the fasteners 206, 3430, the body 3401, the support 3440, the frictional elements 3450, and/or the columns 3430) can be made of a suitable biocompatible material. For example, the cartridge 200, 3400 can include stainless steel. In some examples, the cartridge 200, 3400 can include other biocompatible materials, but is not limited to: nitinol, bioresorbable materials, etc. In some examples, any portion of the cartridge 200, 3400 can include a surface coating that can minimize the risk of thrombosis, intimal hyperplasia, inflammation, scarring, etc.

Figure 36:
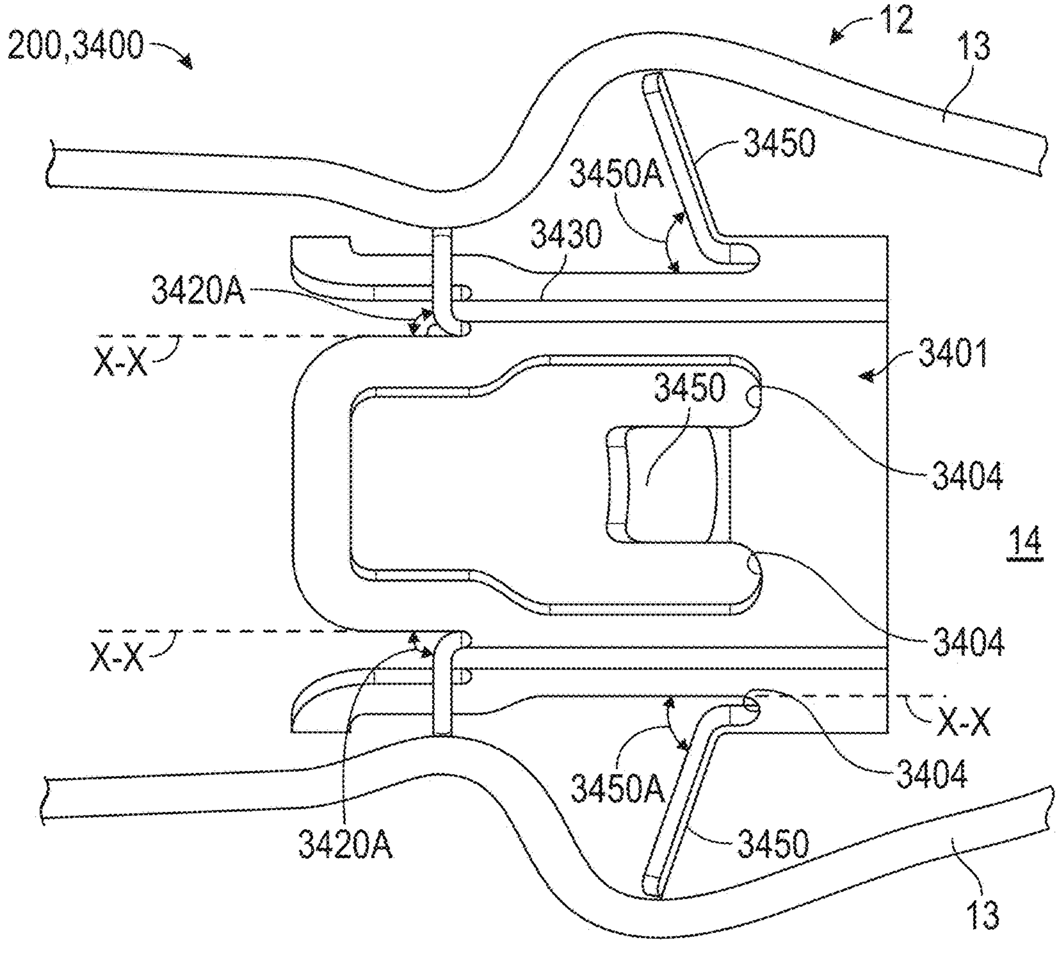
FIG. 36 illustrates the cartridge coupled with a tubular structure.
Figure 37:
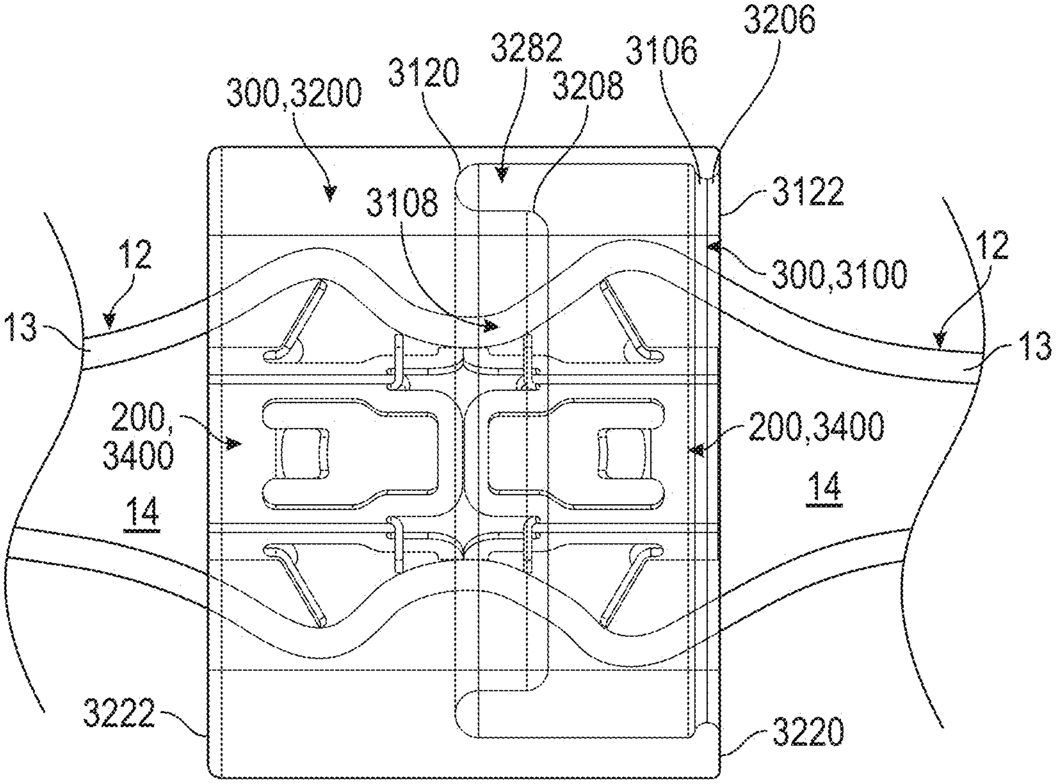
FIG. 37 illustrates a male ring coupled with a female ring to couple the two tubular structures together.

For implementation of the cartridge 200, 3400, as illustrated in FIGS. 36 and 37, the tubular structure 12 can be drawn over the cartridge 200, 3400. For example, the tubular structure 12 can be drawn over the fasteners 206, 3420 and the frictional elements 3450. The fasteners 206, 3420 can at least partially pierce the wall 13 of the tubular structure 12 through elastic recoil of the tubular structure 12 with gentle traction on the cartridge 200, 3400, and/or through manual means by the operator.

As illustrated in FIG. 37, when the rings 3100, 3200 are coupled with one another, the lumens 14 of the two tubular structures 12 are aligned in fluid communication with one another. In at least one example, the rings 3100, 3200 can create a seal to prevent fluid leakage. Accordingly, the anastomotic coupler 10 provides a more reliable, faster, more secure anastomotic coupling device to create a sealed, leak-proof, open connection between the ends of the tubular structures 12 and allow for "stented" unobstructed flow of luminal contents through the connection/anastomosis (e.g. blood, lymph, fluid, stool contents, gastric contents, etc.). This connection can be strong enough to withstand tension, traction, and high flow pressure, which may occur with distal obstruction.

The disclosures shown and described above are only examples. Even though numerous properties and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

The invention claimed is:

1. A cartridge for an anastomotic coupler, the cartridge comprising:

a frame extending along a longitudinal axis;

one or more fasteners extending from the frame at an oblique angle from the longitudinal axis, the one or more fasteners operable to at least partially puncture a wall of a tubular structure to secure the tubular structure to a ring positioned external of the tubular structure; and one or more frictional elements extending from the frame at an oblique angle from the longitudinal axis, the one or more frictional elements operable to assist with securing the tubular structure to the ring through outward radial compression against the wall of the tubular structure without puncturing the wall.

2. The cartridge of claim 1, wherein the one or more fasteners each have an end that is linear, curved, bent, and/or hooked.

3. The cartridge of claim 1, wherein the frame includes a body that has a diameter substantially the same as a diameter of a lumen of the tubular structure so that a body outer radial surface abuts against the wall of the tubular structure to maintain the shape of the tubular structure.

4. The cartridge of claim 3, wherein the body forms a lumen to permit fluid to flow across the frame.

5. The cartridge of claim 3, wherein at least one of the one or more frictional elements extends from the body.

6. The cartridge of claim 3, wherein the frame includes one or more columns that extend from the body along the longitudinal axis.

7. The cartridge of claim 6, wherein at least one of the one or more fasteners extends from the one or more columns.

8. The cartridge of claim 1, wherein the angle that the one or more fasteners extend from the longitudinal axis is between about 1 degree and about 90 degrees.

9. The cartridge of claim 1, wherein the angle that the one or more fasteners extend from the longitudinal axis is between about 65 degrees and about 80 degrees.

10. The cartridge of claim 1, wherein the angle that the one or more frictional elements extend from the longitudinal axis is between about 1 degree and about 90 degrees.

11. An anastomotic coupler comprising:

a ring operable to receive a tubular structure extending along a longitudinal axis; and a cartridge operable to be received in the tubular structure, the cartridge including:

a frame extending along a longitudinal axis;

one or more fasteners extending from the frame at an oblique angle from the longitudinal axis, the one or more fasteners operable to at least partially puncture a wall of a tubular structure to secure the tubular structure to a ring positioned external of the tubular structure; and one or more frictional elements extending from the frame at an oblique angle from the longitudinal axis, the one or more frictional elements operable to assist with securing the tubular structure to the ring through outward radial compression against the wall of the tubular structure without puncturing the wall, wherein the cartridge assists in coupling the ring with the tubular structure as the one or more fasteners and the one or more frictional elements engage the tubular structure.

12. The anastomotic coupler of claim 11, wherein the one or more fasteners each have an end that is linear, curved, bent, and/or hooked.

13. The anastomotic coupler of claim 11, wherein the frame includes a body that has a diameter substantially the same as a diameter of a lumen of the tubular structure so that a body outer radial surface abuts against the wall of the tubular structure to maintain the shape of the tubular structure.

14. The anastomotic coupler of claim 13, wherein the body forms a lumen to permit fluid to flow across the frame.

15. The anastomotic coupler of claim 13, wherein at least one of the one or more frictional elements extends from the body.

16. The anastomotic coupler of claim 13, wherein the frame includes one or more columns that extend from the body along the longitudinal axis.

17. The anastomotic coupler of claim 16, wherein at least one of the one or more fasteners extends from the one or more columns.

18. The anastomotic coupler of claim 11, wherein the angle that the one or more fasteners extend from the longitudinal axis is between about 1 degree and about 90 degrees.

19. The anastomotic coupler of claim 11, wherein the angle that the one or more fasteners extend from the longitudinal axis is between about 65 degrees and about 80 degrees.

20. The anastomotic coupler of claim 11, wherein the angle that the one or more frictional elements extend from the longitudinal axis is between about 1 degree and about 90 degrees.

* * * * *